United States Patent
Shimizu et al.

(10) Patent No.: US 9,962,215 B2
(45) Date of Patent: *May 8, 2018

(54) TREATMENT DEVICE

(71) Applicant: TERUMO KABUSHIKI KAISHA, Shibuya-ku, Tokyo (JP)

(72) Inventors: Katsuhiko Shimizu, Fujinomiya (JP); Youichirou Kuwano, Atsugi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 376 days.

This patent is subject to a terminal disclaimer.

(21) Appl. No.: 14/663,047

(22) Filed: Mar. 19, 2015

(65) Prior Publication Data

US 2015/0265332 A1     Sep. 24, 2015

(30) Foreign Application Priority Data

Mar. 24, 2014   (JP) .................. 2014-060706

(51) Int. Cl.
| | |
|---|---|
| *A61B 18/14* | (2006.01) |
| *A61B 18/08* | (2006.01) |
| *A61B 18/00* | (2006.01) |
| *A61B 18/24* | (2006.01) |
| *A61B 90/00* | (2016.01) |

(52) U.S. Cl.
CPC ........ *A61B 18/082* (2013.01); *A61B 18/1492* (2013.01); *A61B 18/24* (2013.01); *A61B 2018/00214* (2013.01); *A61B 2018/00404* (2013.01); *A61B 2018/00577* (2013.01); *A61B 2018/00589* (2013.01); *A61B 2018/1465* (2013.01); *A61B 2090/0811* (2016.02)

(58) Field of Classification Search
CPC ... A61B 18/082; A61B 18/1492; A61B 18/24; A61B 2018/00214; A61B 2018/00404; A61B 2018/00577; A61B 2018/00589; A61B 2018/1465

See application file for complete search history.

(56) References Cited

U.S. PATENT DOCUMENTS

| | | | | |
|---|---|---|---|---|
| 5,354,296 A | * | 10/1994 | Turkel | A61B 18/1485 606/40 |
| 5,437,665 A | * | 8/1995 | Munro | A61B 18/14 606/41 |
| 5,507,744 A | * | 4/1996 | Tay | A61B 17/0057 606/41 |
| 5,709,224 A | * | 1/1998 | Behl | A61B 18/1492 128/898 |

(Continued)

*Primary Examiner* — Michael Peffley
(74) *Attorney, Agent, or Firm* — Buchanan Ingersoll & Rooney PC

(57) ABSTRACT

Disclosed is a treatment device for occluding a body lumen, including: a hollow shaft which can be inserted into the body lumen; a flat portion forming section which has a pair of arms inserted in the shaft, the arms capable of being protruded from and retracted into a distal end opening of the shaft and expandable widthwise, and which deforms the body lumen into a form having a flat portion as the pair of arms is expanded within the body lumen; and a heating section which is extendable and contractible in a width direction of the flat portion forming section, is extended as the pair of arms is expanded within the body lumen, and heats the flat portion.

9 Claims, 42 Drawing Sheets

(56) References Cited

U.S. PATENT DOCUMENTS

| | | | | |
|---|---|---|---|---|
| 6,165,172 | A  * | 12/2000 | Farley | ............... A61B 18/1492 604/48 |
| 6,306,133 | B1 * | 10/2001 | Tu | ..................... A61B 18/1492 606/41 |
| 7,396,355 | B2 | 7/2008 | Goldman et al. | |
| 7,837,681 | B2 * | 11/2010 | Whayne | ............ A61B 18/1492 606/41 |
| 8,057,469 | B2 * | 11/2011 | Deem | ............... A61B 18/1492 606/215 |

\* cited by examiner

FIG. 11A
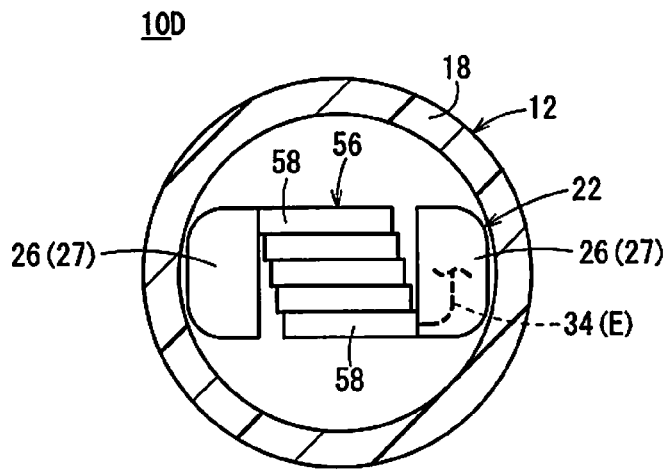
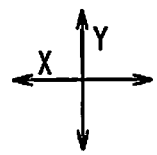
FIG. 11B
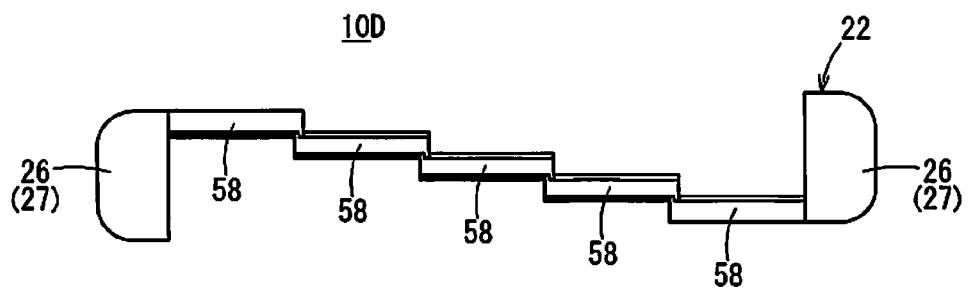
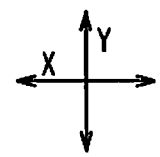

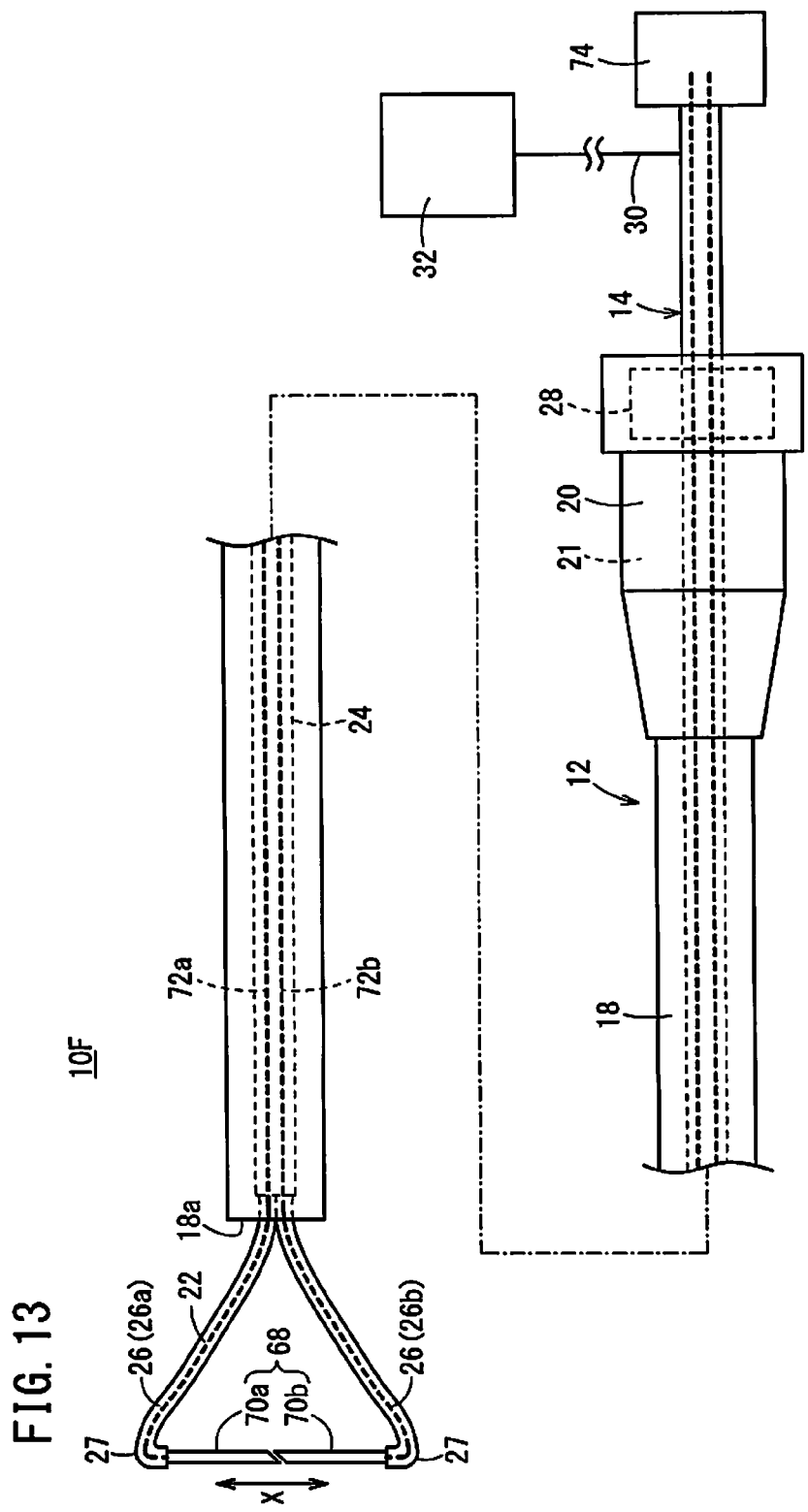

TREATMENT DEVICE

CROSS-REFERENCE TO RELATED APPLICATION

This application claims priority to Japanese Application No. 2014-060706 filed on Mar. 24, 2014, the entire content of which is incorporated herein by reference.

TECHNICAL FIELD

The present disclosure relates to a treatment device for occluding a body lumen such as a blood vessel.

BACKGROUND DISCUSSION

Varicose veins are an example of a disease which can occur in a lumen of a living body. Veins in a living body have venous valves for returning blood to the heart against the effects of gravity. When a venous valve fails, a blood backflow occurs to raise the venous pressure and to expand the vein, resulting in onset of varicose veins.

There are various methods for treatment of varicose veins. Examples of such treatment methods include: (1) compression therapy in which the varicose vein is compressed with elastic bondage or the like to improve stagnation of blood, (2) sclerotherapy in which a sclerosing agent is injected into the vein to induce a trauma in the blood vessel wall, thereby clogging up the blood vessel lumen, (3) vein stripping, i.e., stripping in which the vein is extracted, (4) laser therapy in which the vein is thermally occluded by laser irradiation, and (5) radiofrequency (RF) therapy in which the vein is occluded by heat generated by passing an RF current from an electrode.

U.S. Pat. No. 7,396,355 discloses a treating method in which after injection of a tumescent local anesthesia (TLA) fluid from a syringe into the tissue surrounding a blood vessel to be treated, a catheter provided with electrodes at its distal end is inserted into the blood vessel, and an RF current is passed via the electrodes put in contact with the blood vessel wall to ablate the blood vessel tissue, thereby occluding the blood vessel. In this case, the TLA is used to restrain the pain, to prevent burn of the skin, and to reduce the blood vessel diameter.

SUMMARY

When using the method disclosed in U.S. Pat. No. 7,396,355, it is difficult to inject the TLA fluid uniformly into the periphery of the blood vessel to be treated. If the TLA fluid is injected unevenly, the contraction of the blood vessel will occur unevenly, or will vary from place to place. In such a case, it is impossible or very difficult to achieve sufficient contraction of the blood vessel. Therefore, ablation based on heating by passing an RF current cannot be sufficiently performed, and recanalization of the occluded part of the blood vessel may occur after the treatment.

Disclosed herein is a treatment device with which a treatment for occluding a body lumen can be carried out efficiently.

In one aspect, a treatment device for occluding a body lumen includes: a hollow shaft which can be inserted into the body lumen; a flat portion forming section which has a pair of arms inserted in the shaft, the arms capable of being protruded from and retracted into a distal end opening of the shaft and expandable widthwise, and which deforms the body lumen into a form having a flat portion as the pair of arms is expanded within the body lumen; and a heating section which is extendable and contractible in a width direction of the flat portion forming section, is extended as the pair of arms is expanded within the body lumen, and heats the flat portion.

By applying the flat portion forming section within a body lumen, it is possible to form the body lumen with a flat portion, and, by applying the heating section to the thus formed flat portion, it is possible to effectively occlude the flat portion. In addition, the heating section is compactly stored in a contracted state when inside the shaft, and the heating section can be extended upon the expansion of the pair of arms when outside the shaft. Therefore, the heating section can gain a larger energy releasing area, and can therefore treat the flat portion efficiently, while permitting storage thereof in the shaft.

In the treatment device as above, a configuration may be adopted wherein: the flat portion forming section is expandable widthwise on a more distal side than the shaft, and forms the body lumen with the flat portion at a distal portion of the flat portion forming section upon an expansion of the flat portion forming section within the body lumen; and the heating section is supported by the distal portion of the flat portion forming section. This ensures that when the treatment device is retracted after the formation of the flat portion, the distal end of the device would not be caught on the flat portion. Therefore, the flat portion can be prevented from being opened upon the retracting movement of the treatment device.

In the treatment device, preferably, each arm of the pair of arms is elastically deformable, the pair of arms is expanded widthwise by an elastic restoring force upon protrusion thereof from the distal end opening of the shaft, and the heating section is positioned inside the flat portion of the body lumen as the pair of arms is expanded. According to this configuration, the expanding motion of the pair of arms can be affected easily and reliably by only putting the arms and the shaft into a relative movement in the axial direction.

In the treatment device, the heating section may include a plurality of component members which are capable of relative displacement in the width direction of the flat portion forming section. When this configuration is adopted, a heating section which can have an enlarged energy releasing area when outside the shaft can be realized with a simple configuration.

In the treatment device, the plurality of component members may be a plurality of tubular members constituting a telescopic structure. In this configuration, the heating section has no gap in the width direction of the flat portion forming section when in the extended state. By the heating section, therefore, a more effective heating treatment of the flat portion can be achieved.

In the treatment device, a configuration may be adopted wherein the plurality of component members are stacked in a predetermined direction, with adjacent ones of the component members being slidable in the width direction of the flat portion forming section. In this configuration, the heating section has no gap in the width direction of the flat portion forming section when in the extended state. By the heating section, therefore, a more effective heating treatment of the flat portion can be performed. By this configuration, in addition, the quantities of energy released from the component members can be made even.

In the treatment device, the plurality of component members may be stacked in a longitudinal direction of the pair of arms. This enables the heating treatment of the flat portion to be performed uniformly in the width direction.

A method of occluding a body lumen by use of the treatment device as above includes: an insertion step of inserting the treatment device into the body lumen so as to deliver a distal portion of the treatment device to a treatment site; a flattening step of protruding the pair of arms constituting the flat portion forming section from the hollow shaft of the treatment device, and, upon this, expanding the arms so as to form the body lumen with a flat portion and extending the heating section provided to be extendable and contractible in a width direction of the pair of arms; and a heating step of heating the flat portion by the heating section disposed in an extended state inside the flat portion.

In the flattening step, the formation of the body lumen with the flat portion may be performed at a distal portion of the flat portion forming section.

In the heating step, preferably, the flat portion is heated by the heating section provided at the distal portion of the flat portion forming section.

In the flattening step, the pair of arms may be expanded widthwise by an elastic restoring force upon protrusion thereof from the distal end opening of the shaft.

In extending the heating section, a plurality of component members possessed by the heating section may be put into relative displacement in a width direction of the flat portion forming section.

In extending the heating section, the plurality of component members may be slid in the width direction of the flat portion forming section.

In extending the heating section, the plurality of component members stacked in a longitudinal direction of the pair of arms may be slid in the width direction of the flat portion forming section.

In extending the heating section, a plurality of tubular members possessed by the heating section may be put into relative displacement in the width direction of the flat portion forming section.

With the treatment device according to the described aspect, a treatment for occluding a body lumen can be carried out efficiently.

BRIEF DESCRIPTION OF THE DRAWINGS

FIG. 11A is a partially sectional view of a distal portion of a treatment device including an extendable electrode section according to a third configuration example, and FIG. 11B is a view showing a state where a pair of arms of the treatment device of FIG. 11A is expanded;

FIG. 13 is a partially omitted schematic view of yet another treatment device;

DETAILED DESCRIPTION

Figure 1:
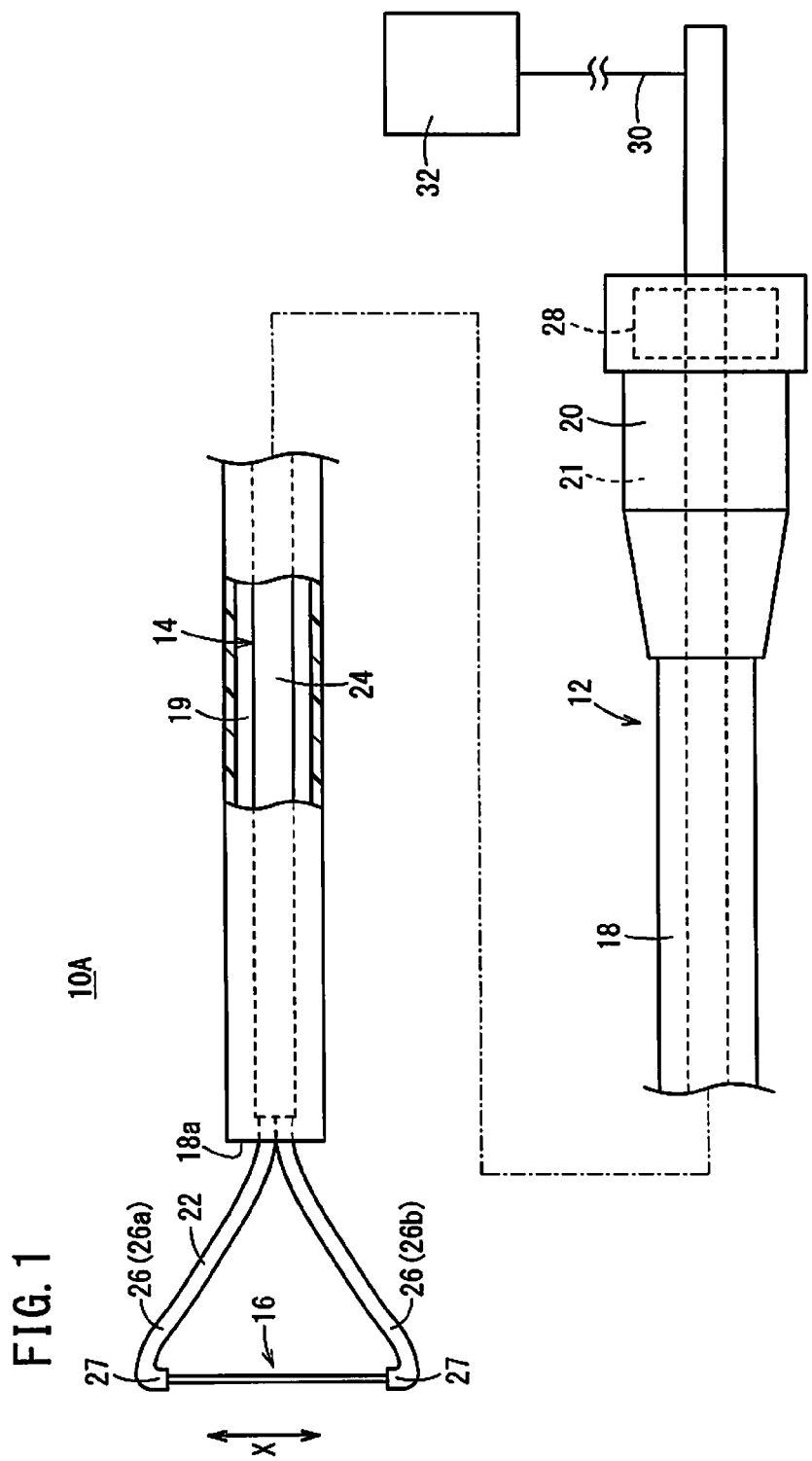
FIG. 1 is a partially omitted schematic view showing a configuration of a treatment device.

FIG. 1 is a partially omitted schematic view showing a configuration of a treatment device 10A. This treatment device 10A is used for occlusion of a body lumen such as a blood vessel. The treatment device 10A includes: a catheter 12 which can be inserted into and passed through a body lumen; an internal device 14 which is inserted in the catheter 12 so as to be slidable in a longitudinal direction; and an electrode section 16 provided at a distal end of the internal device 14 to function as a heating section.

The catheter 12 includes a flexible, hollow-structured shaft 18 (elongated body) constituting a catheter main body, and a hub 20 connected to a proximal portion of the shaft 18. The shaft 18 has a lumen 19 extending from a distal end to a proximal end of the shaft 18. The length of the shaft 18 varies depending on an object of treatment by the treatment device 10A. For instance, in the case where the object of treatment is a varicose vein generated in a lower limb, the length of the shaft 18 is set to be about 500 mm to 4,000 mm, for example.

The material forming the shaft 18 is not specifically restricted. Examples of the material include polymeric materials such as polyolefins (for example, polyethylene, polypropylene, polybutene, ethylene-propylene copolymer, ethylene-vinyl acetate copolymer, ionomers, or mixtures of two or more of these polymers), polyvinyl chloride, polyamides, polyamide elastomers, polyurethane, polyurethane elastomers, polyimides, fluoro-resins, etc., and multi-layer tubes formed from two or more of these polymeric materials.

The hub 20 connected to the proximal portion of the shaft 18 is a part to be grasped by an operator, who uses the treatment device 10A, so as to operate the catheter 12. The hub 20 may be formed, for example, of a rigid resin or the like. The hub 20 has a hollow structure; specifically, the hub 20 has a lumen 21 penetrating the hub 20 in the axial direction. The lumen 21 of the hub 20 communicates with the lumen 19 of the shaft 18.

The internal device 14 includes a flat portion forming section 22 configured to deform a body lumen into a form having a flat portion F (see FIG. 5), and an elongated support 24 supporting the flat portion forming section 22. The flat portion forming section 22 is expandable widthwise (in outward directions) on a more distal side than the shaft 18, and has a function of deforming a body lumen (e.g., vein), at a roughly distalmost position of the treatment device 10A, into a form having a flat portion F upon the expansion of the flat portion forming section 22 within the body lumen.

Specifically, the flat portion forming section 22 has a pair of oppositely extending arms 26 (26a, 26b) which can be protruded from and retracted into a distal end opening 18a of the shaft 18 and can be expanded widthwise (in an X direction in FIG. 1). In the embodiment, the arms 26 are each elastically deformable.

In the embodiment, the shaft 18 has an inside diameter of 1.0 mm to 2.5 mm, and the arms 26 each have an outside diameter of 0.3 mm to 1.0 mm. Furthermore, a normal vein has an inside diameter of 2.0 mm to 20.0 mm (with the inside diameter of the vein after the formation of the flat portion therefore being approximately 27 mm to 207 mm). Therefore, the pair of arms 26 has a width in their stored state of 0.6 mm to 2.0 mm, and the arms 26 are expanded to a width of 27 mm to 207 mm when displaced in opposite directions.

Figure 2:
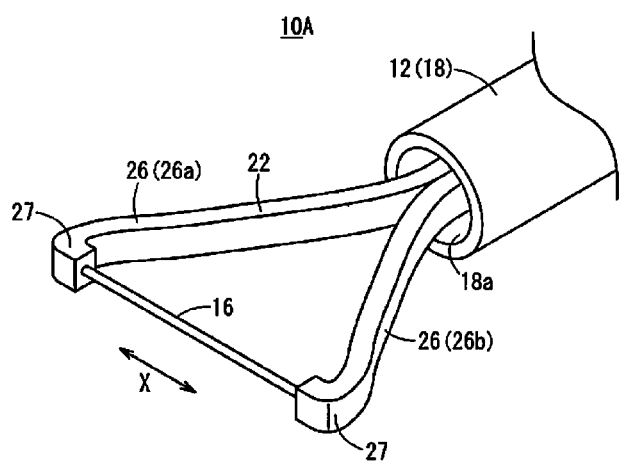
FIG. 2 is a perspective view of a distal portion of the treatment device shown in FIG. 1.
Figure 3A:
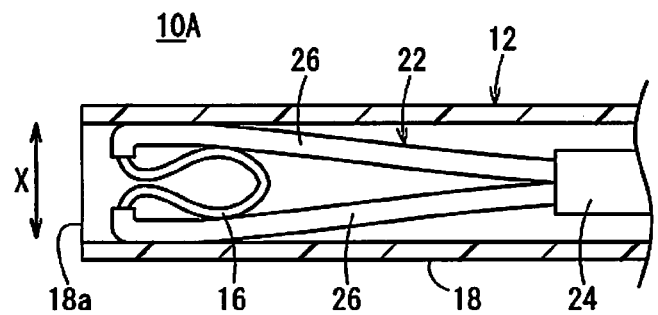
FIG. 3A is a partially sectional view showing a state where a pair of arms of the treatment device of FIG. 1 is stored in a shaft.
Figure 3B:
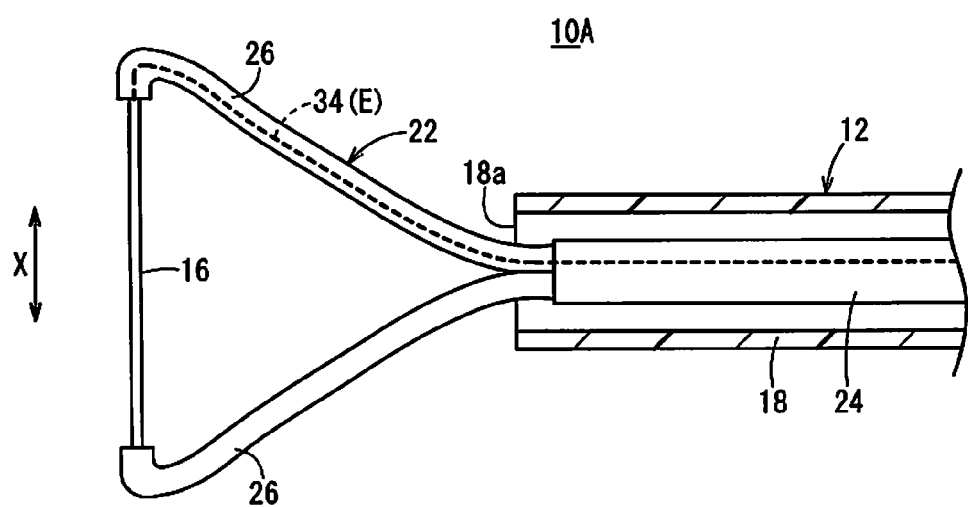
FIG. 3B is a partially sectional view showing a state where the pair of arms of the treatment device of FIG. 1 is expanded.

In FIG. 3A, the pair of arms 26 is in a contracted state (a state where the pair of arms 26 is closed) as they are stored in the shaft 18 and their expansion is restricted by an inner surface of the tube. When the pair of arms 26 is protruded from the distal end opening 18a of the shaft 18 as shown in FIGS. 1, 2, and 3B, the pair of arms 26 is expanded widthwise by elastic restoring forces. When the pair of arms 26 is in the expanded state, the spacing between their outer ends is maximum at their free end portions (distal end portions 27).

The free end portion (distal end portion 27) of each arm 26 is bent toward an inner side (inner side in the width direction of the flat portion forming section 22), whereby a distal end outer surface of the arm 26 is formed in a rounded shape. This ensures that the distal end portion 27 of each arm 26 can be prevented from injuring an inner wall of a body lumen upon contacting the inner wall, and can be prevented from penetrating a blood vessel.

As the material forming the arms 26, there can be used a metal or resin that has an elasticity sufficient for the arms 26 to expand widthwise by their elastic restoring forces. Examples of such a metal include metals of ordinary elasticity such as stainless steel, tantalum, cobalt alloys, copper alloys, etc. and superelastic alloys. Especially, superelastic alloys are preferable for use as the material of the arms 26, since a sufficient elastic restoring force can be obtained thereby. Examples of the superelastic alloys include Ni—Ti alloys, Ti—Ni—Fe alloys, Cu—Zn alloys, Cu—Zn—Al alloys, Cu—Al—Ni alloys, Cu—Au—Zn alloys, Cu—Sn alloys, Ni—Al alloys, Ag—Cd alloys, Au—Cd alloys, In—Ti alloys, and In—Cd alloys.

The elongated support 24 supporting the pair of arms 26 is a flexible member which is inserted in the catheter 12 so as to be slidable in the longitudinal direction. In a state where the pair of arms 26 is protruded from the distal end opening 18a of the shaft 18 and expanded, the support 24 is protruded (exposed) to the proximal side of the proximal end of the catheter 12 (the proximal end of the hub 20). The operator who uses the treatment device 10A can grasp the support 24 protruded from the proximal end of the catheter 12. The material forming the support 24 can be selected from those materials which have been mentioned as examples of the material forming the shaft 18 of the catheter 12. Note that the support 24 is not limited to the one that is configured as a member separate from the arms 26, but may be configured by extending the arms 26 proximally to protrude from the proximal end of the hub 20. In other words, the arms 26 and the support 24 may be integrally formed in a continuous form.

On the inside of the proximal end of the hub 20, there is provided a seal member 28 for liquid-tight sealing between the hub 20 and the support 24, in order that a liquid such as blood will not leak out via the proximal end of the hub 20 to the exterior of the treatment device 10A.

In the treatment device 10A, the electrode section 16 passes a current (e.g., an RF current) through the flat portion F, formed in the body lumen by the flat portion forming section 22, so as to heat the flat portion F, thereby ablating the flat portion F. Thus, the electrode section 16 functions as an administering section which administers toward the flat portion F a treatment which acts to occlude the flat portion F formed by the flat portion forming section 22 (in this case, electrical energy). The electrode section 16 is formed of a conductive material, is flexible, and is connected at both ends thereof to the respective distal end portions 27 of the pair of arms 26.

In a condition where the pair of arms 26 is stored in the shaft 18, as shown in FIG. 3A, the electrode section 16 is in a bent state inside the shaft 18. In a condition where the pair of arms 26 is protruded from the distal end opening 18a of the shaft 18 and are expanded, as shown in FIG. 3B, the electrode section 16 is pulled by the pair of arms 26 (or is elastically restored by itself) so as to extend in the width direction of the flat portion forming section 22 (in the X direction) between the distal end portions 27 of the pair of arms 26 which is in the expanded state. In FIG. 3B, the electrode section 16 is in a rectilinear shape between the distal end portions 27 of the pair of arms 26 which is in the expanded state.

As shown in FIG. 1, an RF power supply device 32 is connected to a proximal portion of the support 24 (that portion of the support 24 which is protruded from the proximal end of the hub 20) through an electric cable 30. The arm 26 on one side and the support 24 are provided with a wiring 34 that forms an electric path E between the electric cable 30 and the electrode section 16. Specifically, the wiring 34 is connected to one end of the electrode section 16 on the distal side, and is laid along the arm 26 on one side and the support 24 (see FIG. 3B). In addition, the wiring 34 is connected to the electric cable 30 on the proximal side.

The electrode section 16 and the pair of arms 26 are, the pair of arms 26 and the wiring 34 are, and the support 24 and the wiring 34 are, electrically insulated from each other. Such an insulating structure may be built up, for example, by forming the pair of arms 26 and the support 24 from an insulating material or materials. Alternatively, in the case where the pair of arms 26 and the support 24 are formed of a conductive material or materials, the insulating structure may be realized by a configuration wherein an insulating member is interposed between the electrode section 16 and each of the pair of arms 26 and wherein the periphery of the wiring 34 is covered with an insulating coating or covering material.

Now, a treatment method (body lumen occlusion method) by use of the treatment device 10A will be described below, while taking up treatment of a varicose vein as an example.

Figure 4A:
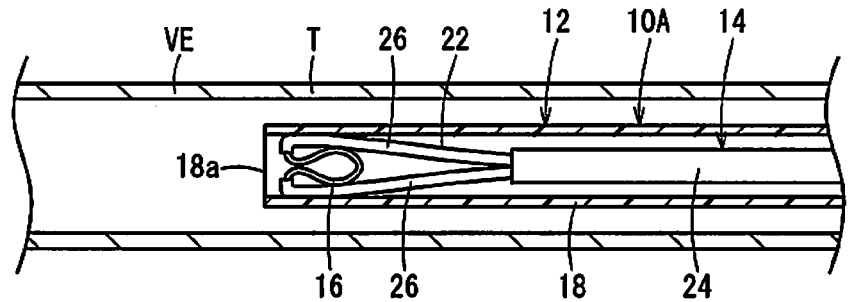
FIG. 4A is a first view for explaining a method of using the treatment device of FIG. 1.

First, the treatment device 10A with the pair of arms 26 and the electrode section 16 stored in the shaft 18 is provided (see FIG. 3A). Next, an insertion step is conducted in which the treatment device 10A is inserted into a vein VE so as to deliver a distal portion of the treatment device 10A to a treatment site T (target site). In the insertion step, specifically, an introducer sheath is made to puncture a patient, and, through the introducer sheath, the treatment device 10A is gradually inserted into the vein VE in which an onset of varicose vein has occurred. In this case, it is preferable to insert the treatment device 10A while checking the position of the distal end of the treatment device 10A under ultrasound guidance. Then, as shown in FIG. 4A, the distal portion of the treatment device 10A is delivered to the treatment site T of the vein VE.

Figure 4B:
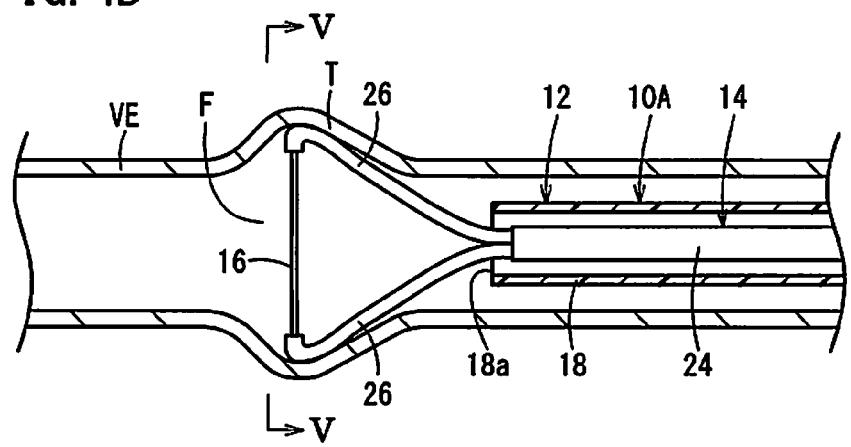
FIG. 4B is a second view for explaining the method of using the treatment device of FIG. 1.

Subsequently, a flattening step is performed in which the vein VE is deformed into a form having a flat portion F. In the flattening step, specifically, the catheter 12 is moved a predetermined distance proximally, with the position of the internal device 14 kept fixed, as shown in FIG. 4B. As a result, the pair of arms 26, upon their protrusion from the distal end opening 18a of the shaft 18, is displaced in such directions that their distal end portions 27 are spaced apart from each other in one plane by their elastic restoring forces, so that the pair of arms 26 is expanded (spread apart) widthwise. Due to the expansion of the pair of arms 26, a wall of the vein VE located outside of each of the arms 26 is forced open radially outward, to bulge outward.

Figure 5:
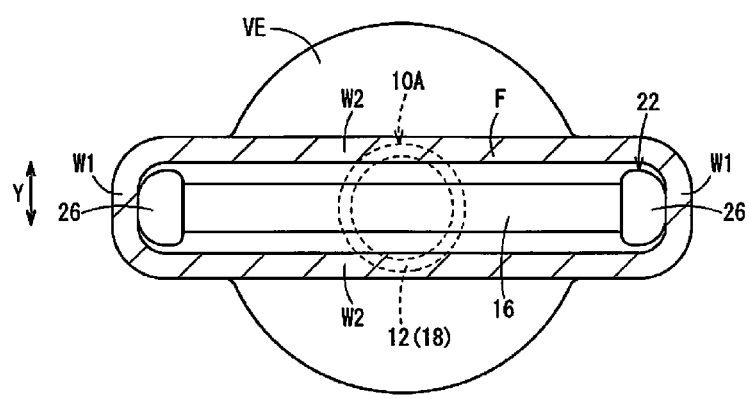
FIG. 5 is a sectional view taken along line V-V of FIG. 4B.

Consequently, as shown in FIG. 5 (a sectional view taken along line V-V of FIG. 4B), the vein VE receiving forces from the pair of arms 26 is deformed to be flat in sectional shape. Specifically, the spacing between walls W1 of the vein VE at the portions pushed by the pair of arms 26 is enlarged, whereby the spacing between walls W2 of the vein VE facing the direction orthogonal to the separating direction of the pair of arms 26 is reduced, so that the vein VE is deformed to assume a flat cross-sectional shape.

Next, a heating step is carried out in which the flat portion F is heated by the electrode section 16. In the heating step, specifically, in order to apply an occluding treatment to the flat portion F of the vein VE by the electrode section 16, a current (RF current) generated by the RF power supply device 32 is supplied to the electrode section 16 via the electric cable 30 and the electric path E (wiring 34). The current thus supplied flows through the flat portion F of the vein VE to heat the flat portion F, whereby the flat portion F is ablated. This heating step can be said to be an administering step in which a treatment which acts to occlude the flat portion F (in this case, electrical energy) is administered toward the flat portion F. Note that during the heating step the electrode section 16 may not necessarily be in contact with the inner wall of the flat portion F of the vein VE, since in this case, also, the current can be passed through the flat portion F by way of blood, which is conductive.

Figure 4C:
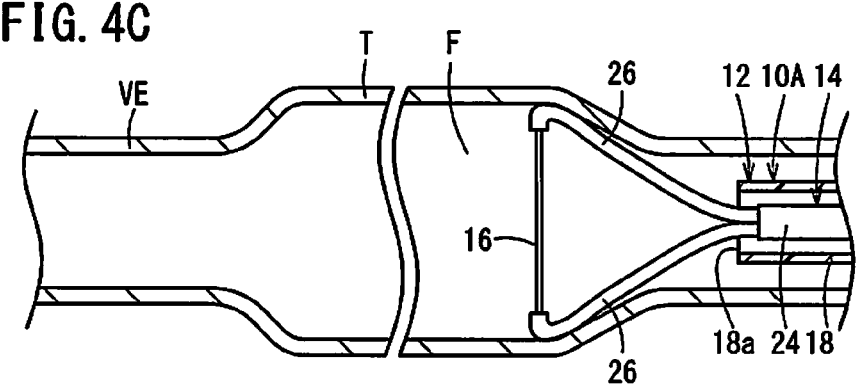
FIG. 4C is a third view for explaining the method of using the treatment device of FIG. 1.

In addition, concurrently with the heating step, a moving step is conducted in which the pair of arms 26 is moved proximally while kept in the expanded state. Specifically, as shown in FIG. 4C, the treatment device 10A with the pair of arms 26 in the expanded state is, as a whole, gradually moved proximally. By this operation, the formation of the flat portion F and the ablation thereof are performed continuously along the vein VE. By the ablation, a tissue at the flat portion F is coagulated and denatured.

After such ablation is applied to a desired range of the vein VE, the pair of arms 26 and the electrode section 16 are re-stored into the shaft 18 (storing step), and the treatment device 10A is drawn out of the living body (the vein VE) (drawing out or extraction step). Note that in re-storing the pair of arms 26 and the electrode section 16 into the shaft 18, the catheter 12 may be moved distally with the position of the internal device 14 kept stationary, or the internal device 14 may be moved proximally with the position of the catheter 12 kept fixed.

Thus, according to the treatment device 10A, the body lumen is formed with the flat portion F by operating the flat portion forming section 22 inside the body lumen, and, thereafter, the treatment for occlusion is applied to the thus formed flat portion F. Therefore, the flat portion F can be occluded efficiently. In addition, the flat portion forming section 22 forms the body lumen with the flat portion F at a substantially distalmost position of the treatment device 10A. This prevents the distal end of the treatment device 10A from being caught on the flat portion F at the time of the retracting movement of the treatment device 10A after the formation of the flat portion F. Consequently, opening (recanalization) of the flat portion F can be prevented from occurring upon the retracting movement of the treatment device 10A.

In the case of the treatment device 10A, besides, the flat portion forming section 22 has the pair of arms 26 which can protrude and retract with reference to the distal end opening 18a of the shaft 18 and can be expanded widthwise, and the spacing between the outer ends of the pair of arms 26 becomes maximum at the distal end portions 27 of the pair of arms 26 in the expanded state. According to this configuration, a body lumen can be formed with a flat portion F easily and reliably at a substantially distalmost portion of the treatment device 10A.

In the case of the treatment device 10A, furthermore, the pair of arms 26 being elastically deformable is expanded widthwise by their elastic restoring forces upon their protrusion from the distal end opening 18a of the shaft 18. Therefore, the expanding motion of the pair of arms 26 can be performed easily and assuredly, by only relatively moving the pair of arms 26 and the shaft 18 in the axial direction.

In the case of the treatment device 10A, a heating treatment (ablation) is applied to a body lumen by administering electrical energy to the flat portion F of the body lumen. Therefore, the body lumen can be occluded in a favorable manner.

Figure 6A:
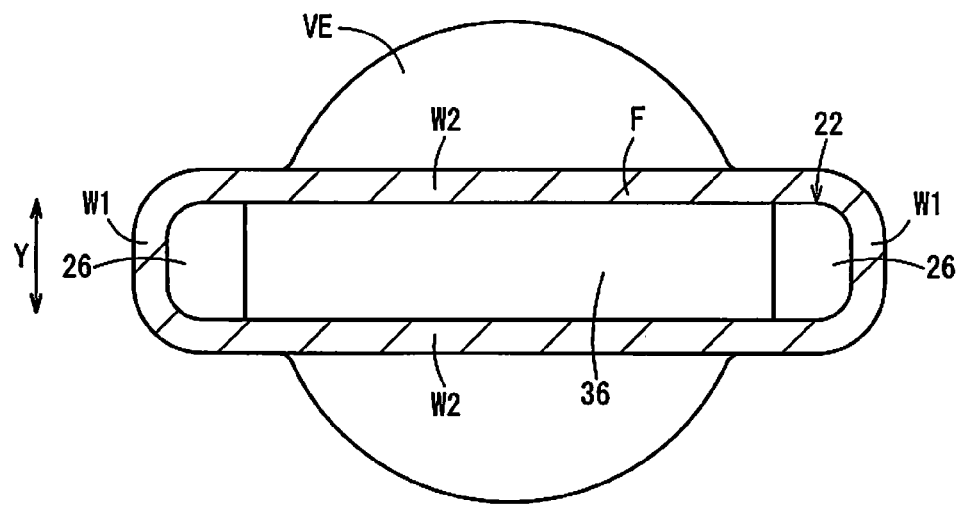
FIG. 6A is a view depicting another electrode section.

Note that in the treatment device 10A, the aforementioned electrode section 16 may be replaced by an electrode section 36 depicted in FIG. 6A. The thickness of the electrode section 36 is set to be equal to or greater than the thickness (the dimension in a Y direction) of the arm 26. Where such an electrode section 36 is applied, the electrode section 36 makes contact with inner surfaces of the walls W2 of the flat portion F when the body lumen is formed with the flat portion F by the expansion of the pair of arms 26. This configuration enables a current to be passed through the flat portion F efficiently. Accordingly, the flat portion F can be ablated effectively.

Figure 6B:
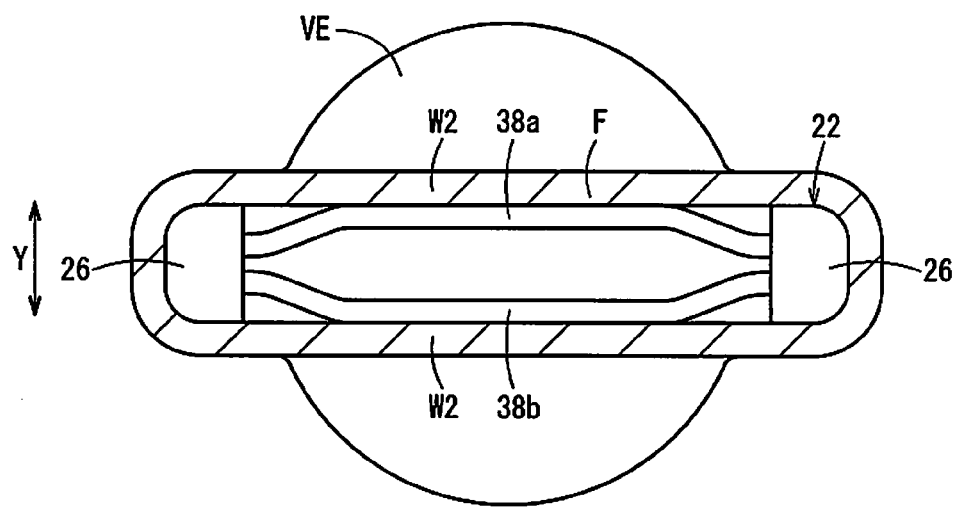
FIG. 6B is a view showing a further electrode section.

In the treatment device 10A, the aforementioned electrode section 16 may be substituted by electrode sections 38a and 38b shown in FIG. 6B. In FIG. 6B, specifically, two electrode sections 38a and 38b are provided, spaced apart in the thickness direction of the pair of arms 26 (in the Y direction). When the body lumen is formed with the flat portion F by the expansion of the pair of arms 26, the electrode section 38a on one side makes contact with the inner surface of the flat wall W2 on the one side which constitutes the flat portion F, and the electrode section 38b on the other side makes contact with the inner surface of the flat wall W2 on the other side which constitutes the flat portion F. With this configuration it is possible to pass a current through the flat portion F efficiently. Consequently, the flat portion F can be ablated effectively.

Now, description will be made of another treatment device including an electrode section which functions as a heating section for applying a heating treatment to a body lumen and which can be extended and contracted in a width direction of a flat portion forming section 22.

Figure 7A:
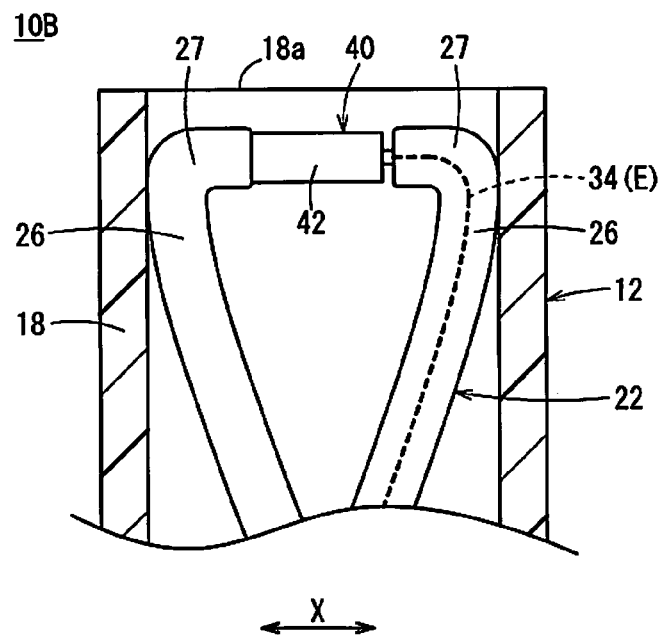
FIG. 7A is a partially sectional view of a distal portion of a treatment device including an extendable electrode section according to a first configuration example.
Figure 7B:
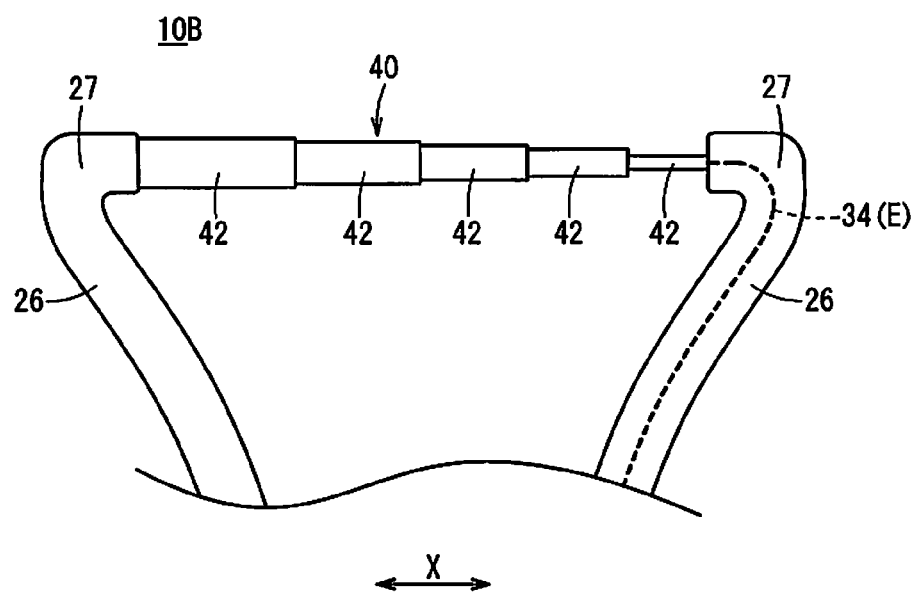
FIG. 7B is a view showing a state where a pair of arms of the treatment device of FIG. 7A is expanded.
Figure 8:
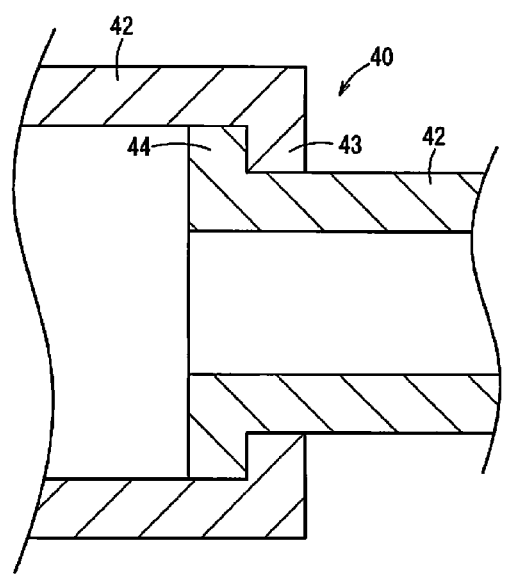
FIG. 8 is a sectional view depicting a slip-off preventive structure between component members of the electrode section of the treatment device shown in FIG. 7A.

FIG. 7A is a partially sectional view of a distal portion of a treatment device 10B including an extendable electrode section 40 according to a first configuration example. In FIG. 7A, the electrode section 40 is in a contracted state between a pair of arms 26 stored in a shaft 18. In FIG. 7B, on the other hand, the electrode section 40 is in an extended state between the pair of arms 26. The electrode section 40 is connected to an end portion of a wiring 34 laid along or within the arm 26.

The electrode section 40 functions as an administering section which administers toward a flat portion F, formed by the flat portion forming section 22, a treatment which acts to occlude the flat portion F (electrical energy). The electrode section 40 is provided at a distal portion of the flat portion forming section 22 (specifically, between distal end portions 27 of the pair of arms 26), and is extended upon the expansion of the pair of arms 26 in a body lumen.

The electrode section 40 includes a plurality of (in the illustrated example, five) component members 42 which are relatively displaceable in the width direction of the flat portion forming section 22 and which output a current. The adjacent ones of the component members 42 are slidable in the width direction of the flat portion forming section 22 (in an X direction). The plurality of component members 42 are a plurality of hollow tubular members which are different in thickness (diameter) and which all together constitute a telescopic structure.

As restriction means (slip-off preventive structure) for setting an extension limit between the adjacent component members 42, an inward locking projection 43 and an outward locking projection 44 are provided at end portions of each of the component members 42. When the component members 42 are relatively moved a predetermined distance in a direction for extending the electrode section 40, the inward locking projection 43 and the outward locking projection 44 possessed by the adjacent component members 42 contact each other, whereby a further relative displacement is restrained. In this way, separation of the component members 42 from one another is inhibited.

In the case of using the treatment device 10B, a treatment of a body lumen can be carried out by generally the same procedure (see FIGS. 4A to 4C) as in the case of the treatment device 10A shown in FIG. 1. Specifically, in the case of using the treatment device 10B, first, an insertion step is conducted in the same manner as in the case of using the treatment device 10A.

Next, a flattening step of deforming a body lumen into a form having a flat portion F is performed. Specifically, upon protrusion of the pair of arms 26 from the shaft 18, the pair of arms 26 is expanded to form the body lumen with the flat portion F, and, in addition, the heating section (electrode section 40) provided to be extendable in the width direction of the pair of arms 26 is extended. In this case, upon the protrusion of the pair of arms 26 from a distal end opening 18a of the shaft 18, the pair of arms 26 is expanded widthwise by their elastic restoring forces, and the plurality of component members 42 are relatively displaced in the width direction of the flat portion forming section 22. This causes the electrode section 40, composed essentially of the plurality of component members 42, to extend.

Subsequently, a heating step is carried out in which the flat portion F is heated by the heating section (electrode section 40) disposed in the extended state inside the flat portion F. This heating step can be said to be an administering step of administering toward the flat portion F a treatment which acts to occlude the flat portion F (in this case, electrical energy).

Besides, concurrently with the heating step, a moving step is conducted in which the treatment device 10B, with the pair of arms 26 in the expanded state, is as a whole moved proximally.

Thereafter, a storing step and a drawing-out step are carried out in the same manner as in the case of using the treatment device 10A.

According to the treatment device 10B configured as above, the electrode section 40 is compactly stored in the contracted state when located inside the shaft 18, and is extendable upon the expansion of the pair of arms 26 when located outside the shaft 18. Therefore, the electrode section 40 can gain a larger energy releasing area while permitting storage thereof in the shaft 18, whereby an efficient treatment can be applied to the flat portion F formed in the body lumen.

Besides, since the electrode section 40 has the plurality of component members 42 which are relatively displaceable in the width direction of the flat portion forming section 22 and which output energy, it is possible to enlarge the energy releasing area outside of the shaft 18 while adopting a simple configuration.

Furthermore, since the electrode section 40 has the telescopic structure composed essentially of the plurality of tubular members (component members 42), there is no gap in the width direction of the flat portion forming section 22 in the extended state of the electrode section 40. Accordingly, a heating treatment can be applied to the flat portion F in an effective manner.

Figure 9A:
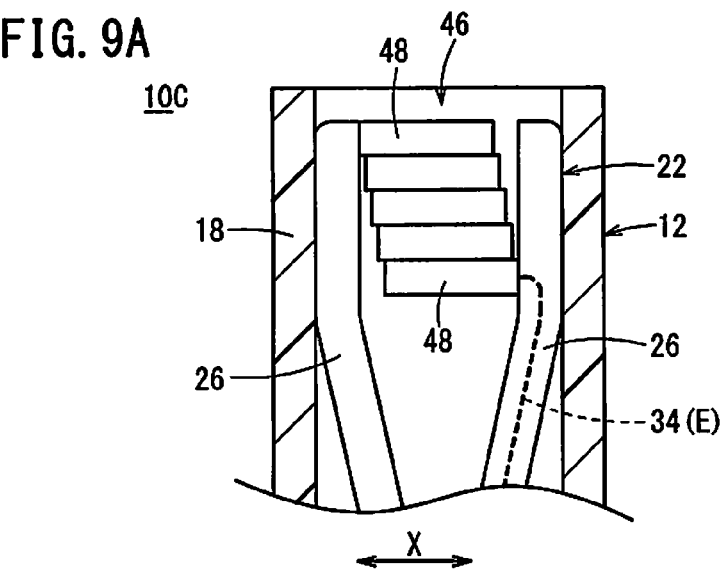
FIG. 9A is a partially sectional view depicting a configuration of a distal portion of a treatment device including an extendable electrode section according to a second configuration example.
Figure 9B:
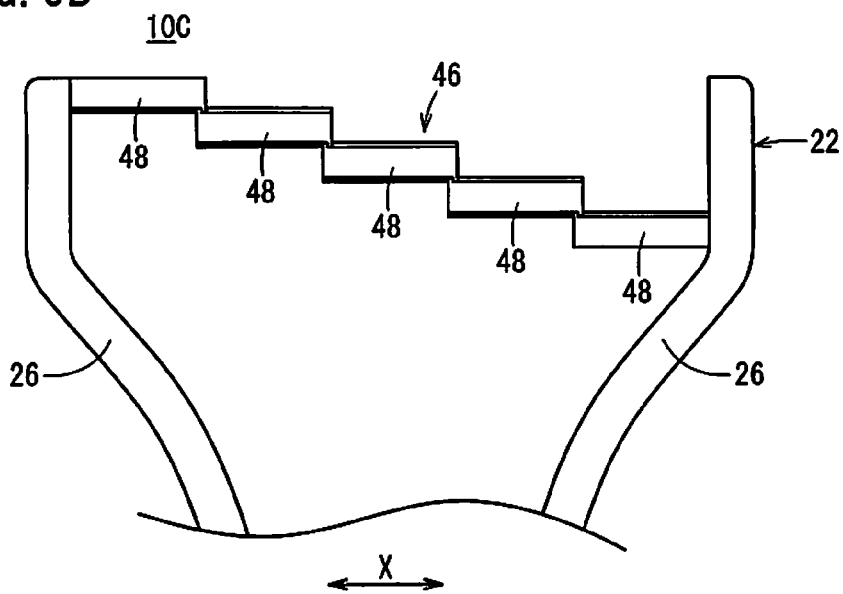
FIG. 9B is a view showing a state where a pair of arms of the treatment device of FIG. 9A is expanded.

FIGS. 9A and 9B are partially sectional views showing a configuration of a distal portion of a treatment device 10C including an extendable electrode section 46 according to a second configuration example. In FIG. 9A, the electrode section 46 is in a contracted state between a pair of arms 26 which are stored in a shaft 18. In FIG. 9B, on the other hand, the electrode section 46 is in an extended state between the pair of arms 26.

The electrode section 46 functions as an administering section for administering toward a flat portion F, formed by a flat portion forming section 22, a treatment which acts to occlude the flat portion F (electrical energy). The electrode section 46 is provided at a distal portion of the flat portion forming section 22, and is extended upon the expansion of the pair of arms 26 inside a body lumen.

The electrode section 46 includes a plurality of (in the illustrated example, five) component members 48 which are relatively displaceable in the width direction of the flat portion forming section 22 and which output a current. Specifically, the plurality of component members 48 is stacked in a predetermined direction (in the illustrated example, in a longitudinal direction of the flat portion forming section 22). Adjacent ones of the component members 48 are slidable in the width direction of the flat portion forming section 22 (in an X direction).

The plurality of component members 48 are set to be equal in width (dimension along the longitudinal direction of the flat portion forming section 22) and in length (dimension in the width direction of the flat portion forming section 22). Therefore, the component members 48 are equal in area in plan view, so that the quantity of energy released from the component members 48 is uniform over the overall area of the component members 48.

Figure 10A:
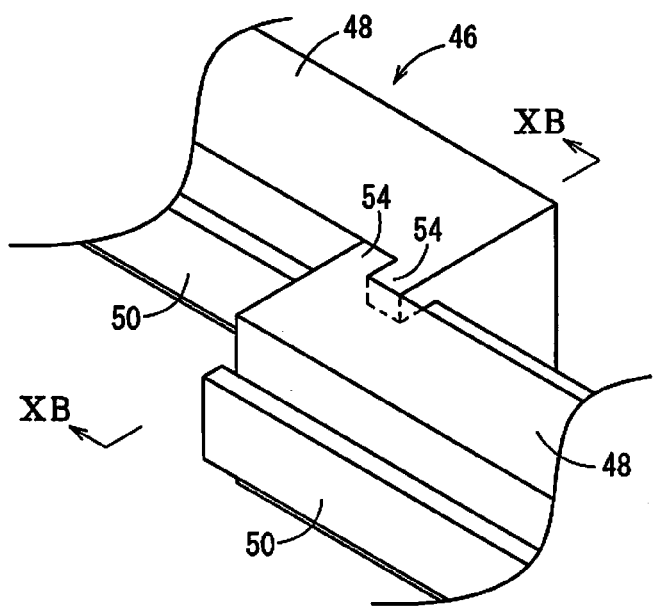
FIG. 10A is a perspective view of adjacent ones of a plurality of component members of the electrode section of the treatment device of FIG. 9A.
Figure 10B:
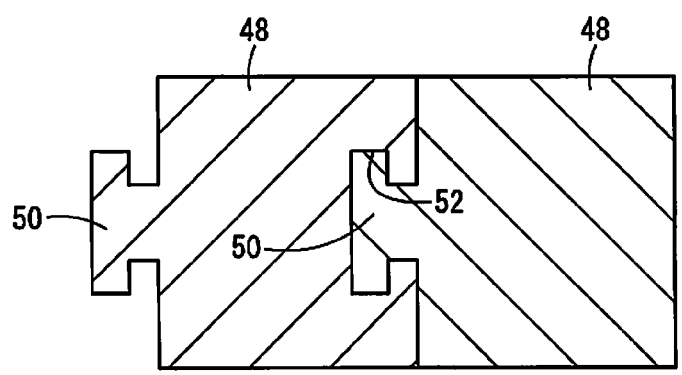
FIG. 10B is a sectional view taken along line XB-XB of FIG. 10A.

FIG. 10A is a perspective view of the adjacent component members 48. FIG. 10B is a sectional view taken along line XB-XB of FIG. 10A. As a guide structure for guiding the sliding of the adjacent component members 48 relative to each other, each of the component members 48 is provided with a guide rail 50 and a guide groove 52 corresponding to the shape of the guide rail 50, along the longitudinal direction of the component member 48. The guide rail 50 and the guide groove 52 engage with each other so that they are slidable relative to each other and that their relative displacement in any direction orthogonal to the sliding direction is restrained. The guide rail 50 and the guide groove 52 are formed in projected and recessed shapes that enable such an engagement.

As restriction means (slip-off preventive structure) for setting an extension limit between the adjacent component members 48, locking projections 54 are provided at end portions of each of the component members 48 as shown in FIG. 10A. When the component members 48 are relatively moved a predetermined distance in the direction for extending the electrode section 46, the locking projections 54 possessed by the adjacent component members 48 contact each other, whereby a further relative displacement is restrained. Consequently, the component members 48 are inhibited from separation from each other.

In the case of using the treatment device 10C, also, a treatment of a body lumen can be carried out by generally the same procedure (see FIGS. 4A to 4C) as in the method of using the treatment device 10A shown in FIG. 1. Specifically, in the case of using the treatment device 10C, first, an insertion step is conducted in the same manner as in the case of using the treatment device 10A.

Next, a flattening step of deforming the body lumen into a form having a flat portion F is performed. Specifically, upon protrusion of the pair of arms 26 from the shaft 18, the pair of arms 26 is expanded to form the body lumen with the flat portion F, and, in addition, the electrode section 46 is extended in the width direction of the arms 26. In this case, upon the protrusion of the pair of arms 26 from a distal end opening 18a of the shaft 18, the pair of arms 26 is expanded widthwise by their own elastic restoring forces, and the plurality of component members 48 are relatively displaced in the width direction of the flat portion forming section 22. This results in that the electrode section 46 composed essentially of the plurality of component members 48 is extended.

Subsequently, a heating step is carried out in which the flat portion F is heated by the electrode section 46 disposed in the extended state inside the flat portion F. This heating step can be said to be an administering step of administering toward the flat portion F a treatment which acts to occlude the flat portion F (in this case, electrical energy).

Besides, concurrently with the heating step, a moving step is conducted in which the treatment device 10C with the pair of arms 26 in the expanded state is as a whole moved proximally.

The electrode section 46 configured as above, also, can gain a larger energy releasing area while permitting the storage thereof in the shaft 18 and can apply an efficient treatment to the flat portion F, in the same manner as the electrode section 40. In addition, since the electrode section 46 includes the plurality of component members 48 relatively displaceable in the width direction of the flat portion forming section 22, the energy releasing area can be enlarged outside of the shaft 18 and the quantity of energy released from the component members 48 can be made to be uniform over the overall area of the component members 48, while adopting a simple configuration.

Figure 9C:
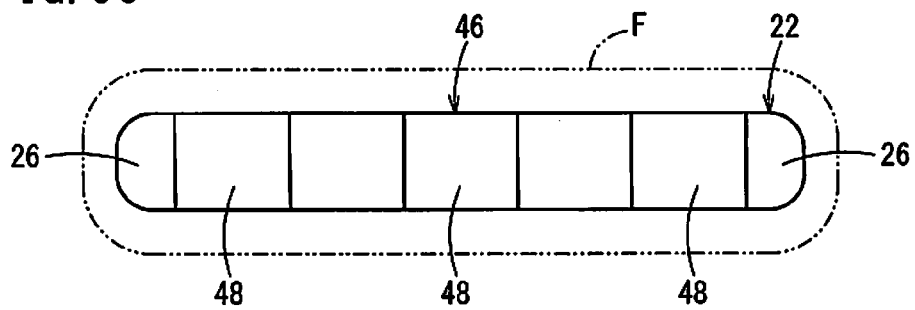
FIG. 9C is a view of the treatment device in the state of FIG. 9B as viewed from the front side.

Particularly in the case of the treatment device 10C, the plurality of component members 48 are stacked in the longitudinal direction of the pair of arms 26. Therefore, by adopting a configuration in which no step is formed in the thickness direction of the flat portion forming section 22 as shown in FIG. 9C, a heating treatment uniform in the width direction can be applied to the flat portion F formed in the body lumen by the expansion of the pair of arms 26.

FIGS. 11A and 11B are partially sectional views of a distal portion of a treatment device 10D including an extendable electrode section 56 (heating section) according to a third configuration example. In FIG. 11A, the electrode section 56 is in a contracted state between a pair of arms 26 stored in a shaft 18. In FIG. 11B, on the other hand, the electrode section 56 is in an extended state between the pair of arms 26.

The electrode section 56 is provided at a distal portion of a flat portion forming section 22 (specifically, between distal end portions 27 of the pair of arms 26), and is extended upon expansion of the pair of arms 26 inside a body lumen. Like the aforementioned electrode section 46, the electrode section 56 includes a plurality of component members 58 which are formed of a conductive material and are mutually slidable in a width direction of the flat portion forming section 22 (in an X direction), and the electrode section 56 can be extended and contracted. In the electrode section 56, the plurality of component members 58 are stacked in a thickness direction of the flat portion forming section 22 (in a Y direction).

Note that though not illustrated in detail, the plurality of component members 58 constituting the electrode section 56, also, include a guide structure and a slip-off preventive structure, like the plurality of component members 42 constituting the electrode section 40 described above.

In the case of using the treatment device 10D, also, a treatment of a body lumen can be performed by the same procedure as in the method of using the treatment device 10C shown in FIG. 9A, etc.

The electrode section 56 configured as above, also, can gain a larger energy releasing area while permitting storage thereof in the shaft 18 and can apply an efficient treatment to the flat portion F formed in the body lumen, like the electrode section 46 shown in FIG. 9A, etc.

Figure 12A:
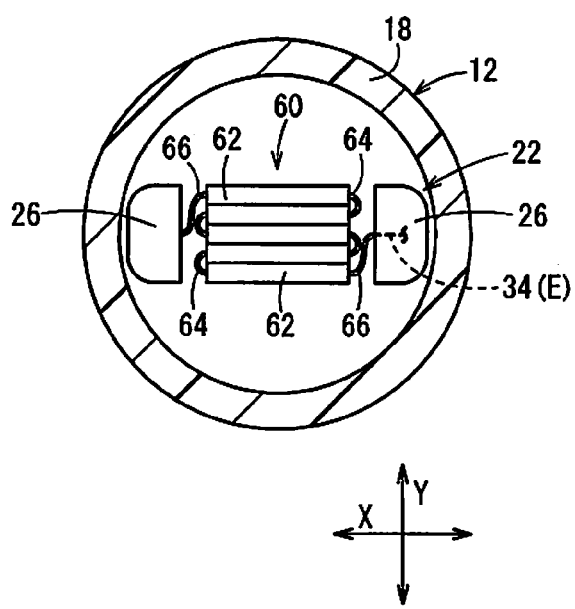
FIG. 12A is a partially sectional view of a distal portion of a treatment device including an extendable electrode section according to a fourth configuration example.
Figure 12B:
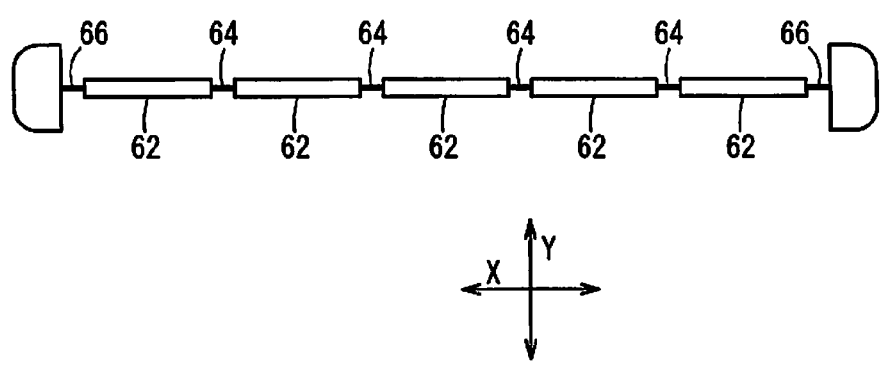
FIG. 12B is a view showing a state where a pair of arms of the treatment device of FIG. 12A is expanded.

FIGS. 12A and 12B are views showing a configuration of a distal portion of a treatment device 10E including an extendable electrode section 60 (heating section) according to a fourth configuration example. In FIG. 12A, the electrode section 60 is in a contracted state between a pair of arms 26 stored in a shaft 18. In FIG. 12B, on the other hand, the electrode section 60 is in an extended state between the pair of arms 26.

The electrode section 60 functions as an administering section adapted to administer toward a flat portion F, formed by a flat portion forming section 22, a treatment which acts to occlude the flat portion F (electrical energy). The electrode section 60 is provided at a distal portion of the flat portion forming section 22, includes a plurality of component members 62 which are formed of a conductive material, and is extended upon the expansion of the pair of arms 26 inside a body lumen.

Especially, this electrode section 60 includes bendable or foldable interlock portions 64 which each interconnect adjacent ones of the component members 62. The interlock portions 64 are electrically conductive, so that when a current is supplied via a wiring 34, the current is passed through all the component members 62. In the illustrated example, each of the interlock portions 64 is composed essentially of a flexible member, and connects end portions of the adjacent component members 62 to each other. The component members 62 constituting both end portions of the electrode section 60 are each connected to the arm 26 by way of a flexible and conductive interlock portion 66. The interlock portion 66 is fixed to a substantially central portion in the thickness direction (in the Y direction) of the arm 26.

In a state where the flat portion forming section 22 (the pair of arms 26) is stored in the shaft 18, as shown in FIG. 12A, the electrode section 60 is folded alternately reversely in the locations of the interlock portions 64, whereby the plurality of component members 62 are aligned in the thickness direction of the flat portion forming section 22. In other words, the electrode section 60 is folded so as to extend (lay itself) to and fro in the width direction of the flat portion forming section 22.

When the flat portion forming section 22 protrudes to the outside of the shaft 18, as shown in FIG. 12B, the interlock portions 64 are stretched straight, and the plurality of component members 62 are aligned substantially in a straight line along the width direction of the flat portion forming section 22 (in the X direction). As a result, the electrode section 60 is extended in the width direction of the flat portion forming section 22.

In the case of using the treatment device 10E, also, a treatment of a body lumen can be carried out by generally the same procedure as in the method of using the treatment device 10A shown in FIG. 1.

Specifically, in the case of using the treatment device 10E, first, an insertion step is carried out in the same manner as in the case of using the treatment device 10A.

Next, a flattening step of deforming a body lumen into a form having a flat portion F is conducted. Specifically, upon protrusion of the pair of arms 26 from the shaft 18, the pair of arms 26 is expanded to form the body lumen with the flat portion F, and, in addition, the electrode section 60 is extended in the width direction of the arms 26. In this case, as the pair of arms 26 protrude from a distal end opening 18a of the shaft 18, the pair of arms 26 is expanded widthwise by their own elastic restoring forces, whereby the plurality of component members 62 are aligned substantially in a straight line along the width direction of the flat portion forming section 22 (see FIG. 12B). As a result, the electrode section 60 composed essentially of the plurality of component members 62 is extended.

Subsequently, a heating step is conducted in which the flat portion F is heated by the electrode section 60 disposed in the extended state inside the flat portion F. This heating step can be said to be an administering step of administering toward the flat portion F a treatment which acts to occlude the flat portion F (in this case, electrical energy).

Besides, concurrently with the heating step, a moving step is carried out in which the treatment device 10E with the pair of arms 26 in the expanded state is as a whole moved proximally.

The electrode section 60 configured as above, also, can gain a larger energy releasing area while permitting storage thereof in the shaft 18 and can apply an efficient treatment to the flat portion F formed in the body lumen, like the other extendable electrode sections 40, 46, and 56 described above.

FIG. 13 is a partially omitted schematic view of yet another treatment device 10F. The treatment device 10F includes an electrode section 68 as a heating section movable relative to a flat portion forming section 22, wires 72a and 72b as flexible power transmission members connected to the electrode section 68, and an actuating section 74 adapted to actuate the wires 72a and 72b. A catheter 12, the flat portion forming section 22, a support 24, an electric cable 30, and an RF power supply device 32 in the treatment device 10F are configured in the same manner as those in the treatment device 10A shown in FIG. 1, etc.

The electrode section 68 includes a pair of flexible heating pieces 70a and 70b. The heating pieces 70a and 70b are each formed of an elastically deformable material. The heating piece 70a on one side is supported in a cantilever manner at its one end by an arm 26a on the one side. The heating piece 70b on the other side is supported in a cantilever manner at its one end by an arm 26b on the other side.

Figure 14A:
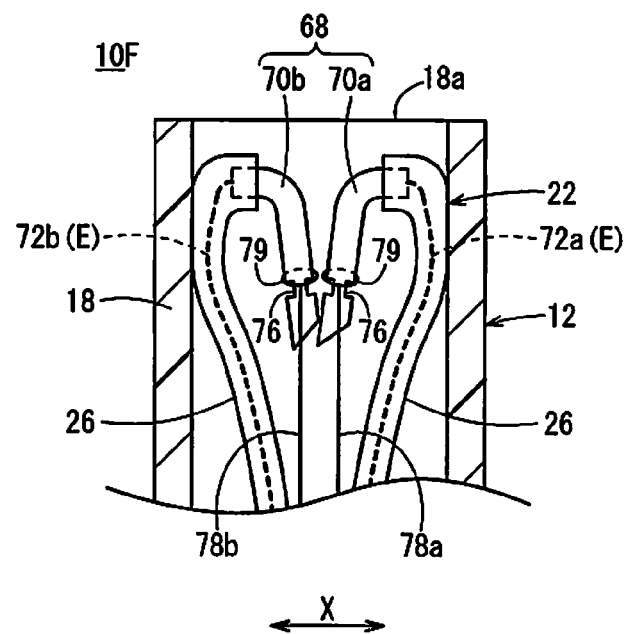
FIG. 14A is a partially sectional view showing a state where a pair of arms of the treatment device of FIG. 13 is stored in a shaft.

In FIG. 14A, the flat portion forming section 22 is stored in the shaft 18, and the pair of heating pieces 70a and 70b are so bent that their free ends are oriented toward the proximal end of the flat portion forming section 22. In this instance, the heating pieces 70a and 70b are each in an elastically deformed state.

Figure 14B:
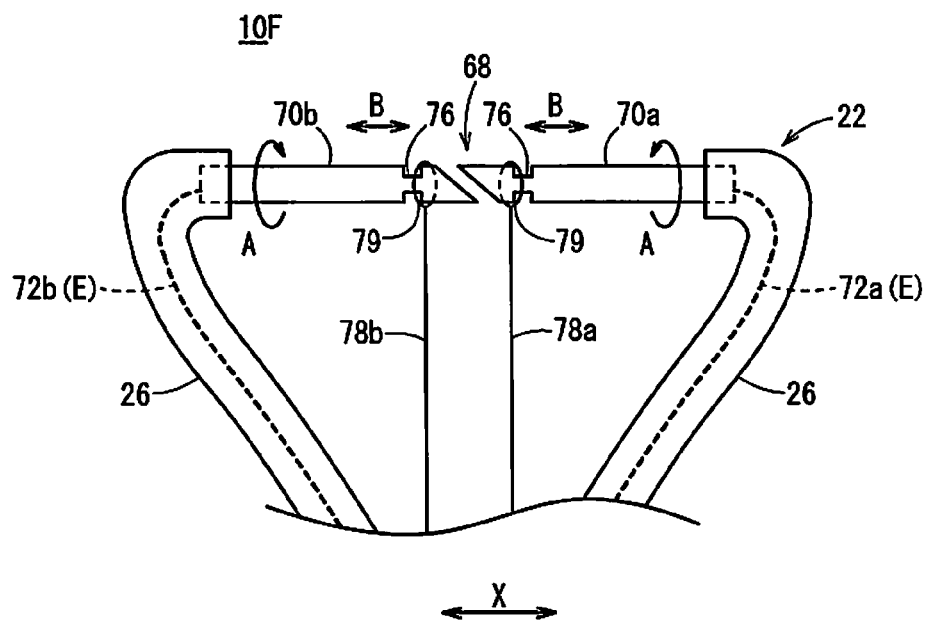
FIG. 14B is a view showing a state where the pair of arms of the treatment device of FIG. 13 is expanded.

In FIG. 14B, on the other hand, a pair of arms 26 constituting the flat portion forming section 22 protruding from a distal end opening 18a of a shaft 18 is expanded widthwise (in an X direction), and the electrode section 68 assumes a substantially rectilinear shape, as the pair of heating pieces 70a and 70b are elastically restored and are aligned in the width direction of the flat portion forming section 22. The free ends of the heating pieces 70a and 70b are each formed slant, and are partly overlapping with each other in the width direction of the flat portion forming section 22. Note that the free ends of the heating pieces 70a and 70b may be in contact with each other or may be proximate to each other, with a minute gap left therebetween.

The heating pieces 70a and 70b are each rotatable about an axis extending in the width direction of the flat portion forming section 22, relative to the arm 26 (rotatable in an A direction in FIG. 14B), or are each reciprocally movable in the width direction of the flat portion forming section 22, relative to the arm 26 (reciprocally movable in a B direction in FIG. 14B). The heating pieces 70a and 70b may each be rotatable about an axis extending in the width direction of the flat portion forming section 22 and be reciprocally movable in the width direction of the flat portion forming section 22, in relation to the arm 26.

The pair of heating pieces 70a and 70b are connected to the wires 72a and 72b, respectively, and are operated in predetermined directions in conjunction with operations of the wires 72a and 72b. The wires 72a and 72b are each slidably inserted in lumens of the arm 26 and the support 24, and each extend to the actuating section 74 (see FIG. 13) provided at the proximal end of the support 24.

The actuating section 74 is able to actuate the wires 72a and 72b to rotate about the axis thereof or is able to actuate the wires 72a and 72b to reciprocate in the axial direction thereof. Alternatively, the actuating section 74 may be able to actuate the wires 72a and 72b to rotate about the axis thereof and be able to actuate the wires 72a and 72b to reciprocate in the axial direction thereof. Though not illustrated in detail, the actuating section 74 includes one or more motors (which may be of a rotary type or of a linear type), and, if necessary, includes a power transmission mechanism (e.g., gears, pulley, belt or the like) for transmission of power between the motor and each of the wires 72a and 72b.

In the case where the actuating section 74 actuates the wires 72a and 72b to rotate about the axis thereof, a torque is transmitted from the actuating section 74 to the heating pieces 70a and 70b through the wires 72a and 72b, whereby the heating pieces 70a and 70b are rotated about the axis extending in the width direction of the flat portion forming section 22.

In the case where the actuating section 74 actuates the wires 72a and 72b to reciprocate, an axial force is transmitted from the actuating section 74 to the heating pieces 70a and 70b through the wires 72a and 72b, whereby the heating pieces 70a and 70b are reciprocated in the width direction of the flat portion forming section 22.

As depicted in FIGS. 14A and 14B, traction members 78a and 78b are connected to the heating pieces 70a and 70b. At the time of re-storing the flat portion forming section 22 and the electrode section 68 into the shaft 18, the traction members 78a and 78b are pulled proximally, whereby the heating pieces 70a and 70b can be forcibly deformed elastically so that their free ends are oriented proximally. This ensures that the flat portion forming section 22 and the electrode section 68 can be easily re-stored into the shaft 18. Note that although detailed illustration is omitted in FIG. 13, the traction members 78a and 78b are inserted in and passed through the catheter 12 (the shaft 18 and a hub 20) and are led out from the proximal end of the hub 20.

In the case of a configuration in which the heating pieces 70a and 70b are rotated about the axis extending in the width direction of the flat portion forming section 22, a connection structure between the traction member 78a or 78b and the heating piece 70a or 70b is preferably so configured as not to obstruct continuous rotation of the heating pieces 70a and 70b. For instance, there may be adopted a configuration in which, as shown in FIGS. 14A and 14B, the heating pieces 70a and 70b are provided with annular grooves 76 at their free ends, and the traction members 78a and 78b are provided at their distal ends with rings 79 for relatively rotatable fitting to the annular grooves 76. This configuration ensures that notwithstanding the traction members 78a and 78b are connected to the heating pieces 70a and 70b, rotation of the heating pieces 70a and 70b is not thereby hampered at all.

The wires 72a and 72b are formed of a conductive material, and are electrically connected to the electric cable 30 on the proximal side of the support 24. Therefore, the wires 72a and 72b each function as an electric path E, whereby a current (RF current) supplied from the RF power supply device 32 can be passed through the heating pieces 70a and 70b by way of the wires 72a and 72b.

A treatment method (body lumen occlusion method) by use of the treatment device 10F will be described below while taking up treatment of a varicose vein as an example. Note that those points which are common to this treatment method by use of the treatment device 10F and the treatment method by use of the treatment device 10A described above will be described with simplification.

Figure 15A:
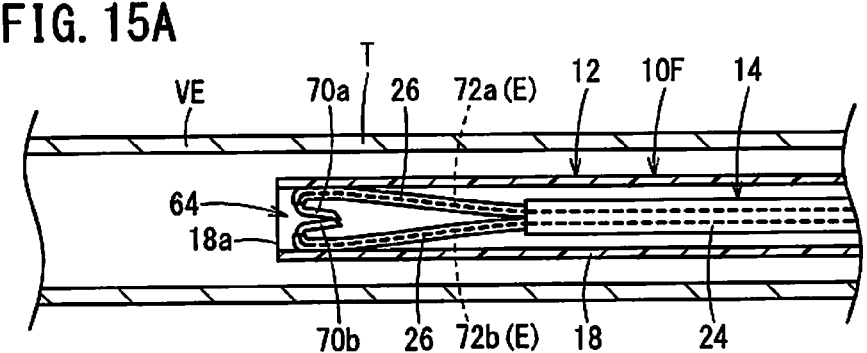
FIG. 15A is a first view for explaining a method of using the treatment device of FIG. 13.

First, the treatment device 10F with the pair of arms 26 and the electrode section 68 stored in the shaft 18 is provided (FIG. 14A). Next, an insertion step is conducted. Specifically, through an introducer sheath made to puncture a patient, the treatment device 10F is inserted into a vein VE in which an onset of a varicose vein has occurred. Then, the treatment device 10F is advanced under ultrasound guidance so as to deliver a distal portion of the treatment device 10F to a treatment site T (target site) of the vein VE, as shown in FIG. 15A.

Figure 15B:
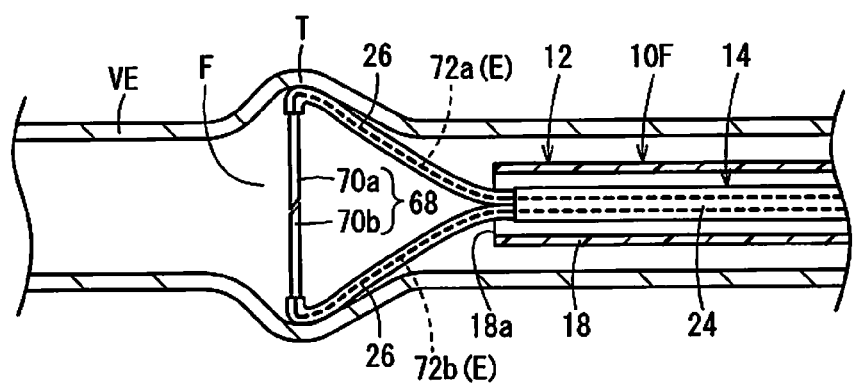
FIG. 15B is a second view for explaining the method of using the treatment device of FIG. 13.

Subsequently, a flattening step of deforming a body lumen into a form having a flat portion F is carried out. Specifically, while the position of an internal device 14 is kept fixed, the catheter 12 is moved proximally by a predetermined distance, whereby the pair of arms 26 is protruded from the distal end opening 18a of the shaft 18, as shown in FIG. 15B. By this operation, the pair of arms 26 is expanded, and the vein VE is formed with the flat portion F (see FIG. 5, as well).

On the other hand, as the pair of arms 26 is protruded from the distal end opening 18a of the shaft 18 and expanded, the heating pieces 70a and 70b constituting the electrode section 68 are each elastically restored into a rectilinear shape. As a result, the electrode section 68 is positioned inside the flat portion F.

Next, a heating step is carried out in which the flat portion F is heated by the electrode section 68 disposed inside the flat portion F, while moving the electrode section 68 relative to the flat portion forming section 22. This heating step can be said to be an administering step of administering toward the flat portion F a treatment which acts to occlude the flat portion F (in this case, electrical energy). Specifically, in the heating step, a current (RF current) generated by the RF power supply device 32 is supplied to the electrode section 68 by way of the electric cable 30 and the electric path E (wires 72a and 72b) so that the current flows through the flat portion F of the vein VE, generating heat, whereby the flat portion F is ablated.

Figure 15C:
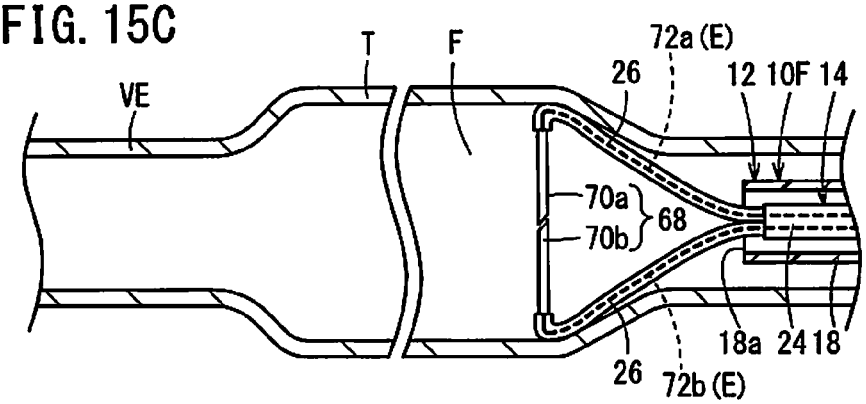
FIG. 15C is a third view for explaining the method of using the treatment device of FIG. 13.

Besides, concurrently with the heating step, a moving step is carried out in which the pair of arms 26 in the expanded state and the electrode section 68 in the heating state are moved along the body lumen. Specifically, the treatment device 10F with the pair of arms 26 expanded is as a whole gradually moved proximally while effecting ablation, as shown in FIG. 15C. This results in that the formation of the flat portion F and the ablation of the flat portion F are continuously performed along the vein VE.

In the aforementioned heating step, during the ablation of the vein VE by the electrode section 68, the electrode section 68 is moved in relation to the flat portion forming section 22, in order to restrain the electrode section 68 from sticking to the tissue of the vein VE. Specifically, the wires 72a and 72b are actuated by the actuating section 74 (see FIG. 13) to rotate or reciprocate, whereby the heating pieces 70a and 70b connected to the wires 72a and 72b are rotated about the axis extending in the width direction of the flat portion forming section 22 or reciprocally moved bit by bit in the width direction of the flat portion forming section 22. This restrains or prevents the heating pieces 70a and 70b from sticking to the tissue of the vein VE. In other words, during the heating of the flat portion F, the heating pieces 70a and 70b are moved in relation to the flat portion F at such a speed that they would not stick to the tissue of the flat portion F. Accordingly, an efficient treatment of the flat portion F can be achieved.

Figure 16A:
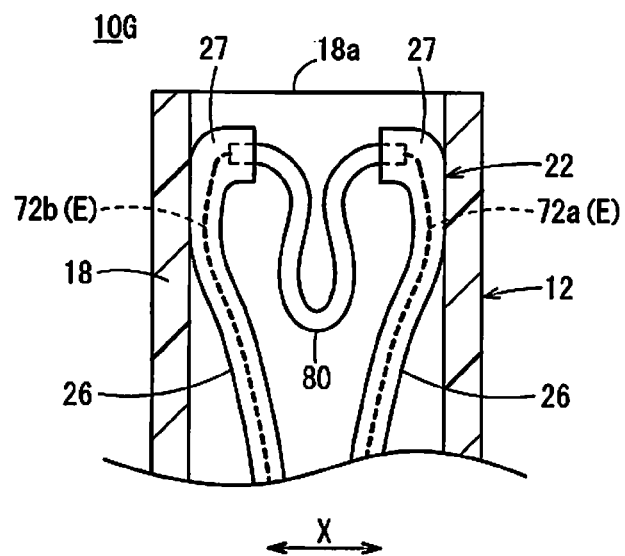
FIG. 16A is a partially sectional view showing a state where a pair of arms of a yet further treatment device is stored in a shaft.
Figure 16B:
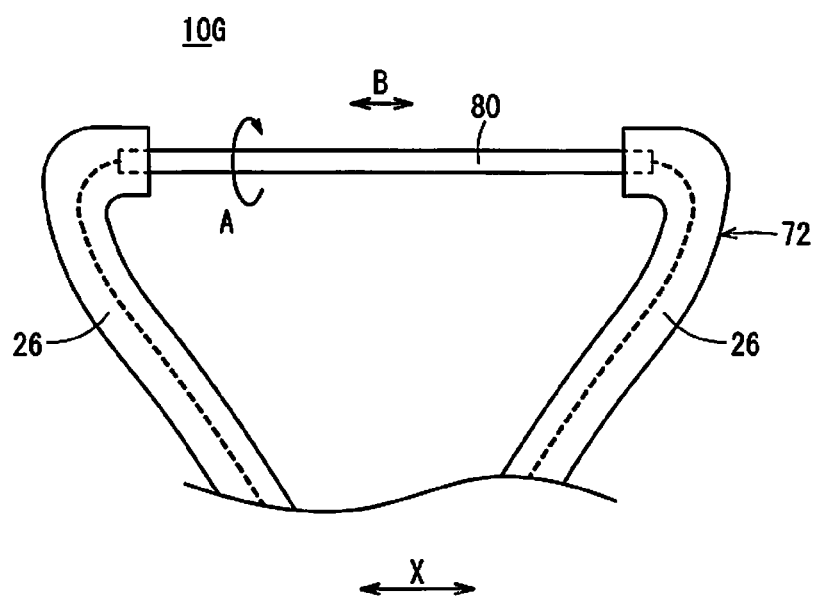
FIG. 16B is a view showing a state where the pair of arms of the treatment device of FIG. 16A is expanded widthwise.

A treatment device 10G depicted in FIGS. 16A and 16B is a modification of the treatment device 10F shown in FIG. 13. Specifically, this treatment device 10G corresponds to a configuration wherein the electrode section 68 as the heating section of the treatment device 10F is replaced by a flexible electrode section 80 arranged between a pair of arms 26. One end and the other end of the electrode section 80 are supported by respective distal end portions 27 of the pair of arms 26.

In FIG. 16A, a flat portion forming section 22 is stored in a shaft 18, and the electrode section 80 is in a bent form. In a condition where the pair of arms 26 is protruded from a distal end opening 18a of the shaft 18 and are expanded, as shown in FIG. 16B, the electrode section 80 is pulled by the pair of arms 26 (or is elastically restored in shape by itself) to assume a rectilinear shape. In other words, the electrode section 80 is extended in the width direction of the flat portion forming section 22 (in an X direction) between the distal end portions 27 of the pair of arms 26 which is in the expanded state.

The electrode section 80 is rotatable about an axis extending in the width direction of the flat portion forming section 22 (rotatable in an A direction in FIG. 16B) in relation to the arms 26 or is reciprocally movable in the width direction of the flat portion forming section 22 (reciprocally movable in a B direction in FIG. 16B) in relation to the arms 26. Alternatively, the electrode section 80 may be rotatable about the axis extending in the width direction of the flat portion forming section 22 and be reciprocally movable in the width direction of the flat portion forming section 22, in relation to the arms 26.

The electrode section 80 is connected to wires 72a and 72b at both ends thereof, and is operated in a predetermined direction in conjunction with an operation of the wires 72a and 72b.

In the case where a actuating section 74 (FIG. 13) actuates the wires 72a and 72b to rotate about their axis, a torque is transmitted from the actuating section 74 to the electrode section 80 by way of the wires 72a and 72b, whereby the electrode section 80 is rotated about the axis extending in the width direction of the flat portion forming section 22. Note that in this case the actuating section 74 actuates the wire 72a on one side and the wire 72b on the other side to rotate at the same rotational speed but in opposite directions, so as to rotate the electrode section 80 in a predetermined direction.

In the case where the actuating section 74 actuates the wires 72a and 72b to reciprocate, an axial force is transmitted from the actuating section 74 to the electrode section 80 via the wires 72a and 72b, whereby the electrode section 80 is reciprocally moved in the width direction of the flat portion forming section 22. Note that in this case the actuating section 74 actuates the wire 72a on one side and the wire 72b on the other side to reciprocate at the same speed but in opposite directions, so as to reciprocally move the electrode section 80 appropriately.

In the case of using the treatment device 10G, also, a treatment of a body lumen can be carried out by the same procedure (see FIGS. 15A to 15C) as in the method of using the treatment device 10F shown in FIG. 13, etc.

Therefore, according to the treatment device 10G, also, like in the case of the treatment device 10F (FIG. 13) including the electrode section 68, the electrode section 80 moves relative to a flat portion F upon its movement relative to the flat portion forming section 22, during the application of energy to the flat portion F, so that the electrode section 80 is restrained from sticking to the tissue of the flat portion F. In other words, while heating the flat portion F, the electrode section 80 is always moved in relation to the flat portion F at such a speed that the electrode section 80 would not stick to the tissue of the flat portion F. This ensures that an efficient treatment of the flat portion F can be achieved.

Especially in the case of the treatment device 10G, the electrode section 80 is held between the pair of arms 26, so that the electrode section 80 can be reliably disposed inside the flat portion F. In addition, the electrode section 80 is prevented from being positionally deviated from the flat portion F, so that a stable treatment can be achieved.

Note that while the heating section for performing a heating treatment of a body lumen has been configured as the electrode section (16, 36, 38a, 38b, 40, 46, 56, 60, 68, 80) adapted to heat the body lumen by passing a current through the body lumen in each of the aforementioned treatment devices 10A to 10G, such an electrode section may be replaced by a heat generating section which utilizes resistance heating. In this case, the heat generating section itself generates heat by resistance heating when a current is passed through the heat generating section, and a body lumen is heated by the thus generated heat. The heat generating section may have an extendable structure similar to those of the aforementioned electrode sections 40, 46, 56, 60, 68, and 80.

Figure 17:
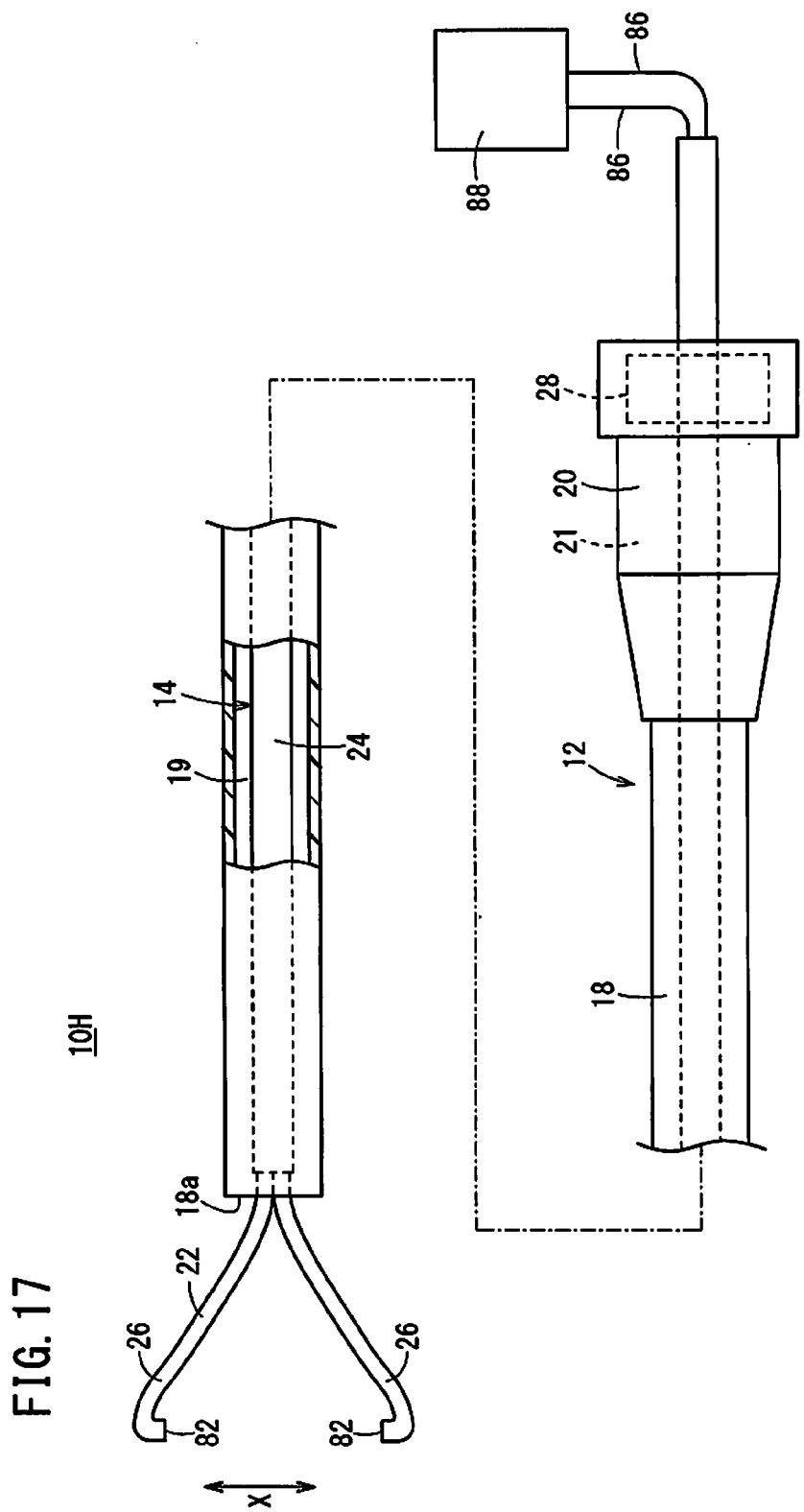
FIG. 17 is a partially omitted schematic view of still another treatment device.

FIG. 17 is a partly omitted schematic view of a yet further treatment device 10H. The treatment device 10H includes irradiation sections 82 which each apply a laser beam L (see FIG. 18A) to a flat portion F formed in a body lumen by a flat portion forming section 22. Therefore, the irradiation sections 82 function as an administering section for administering toward the flat portion F, formed by the flat portion forming section 22, a treatment which acts to occlude the flat portion F (in this case, light energy).

Figure 18A:
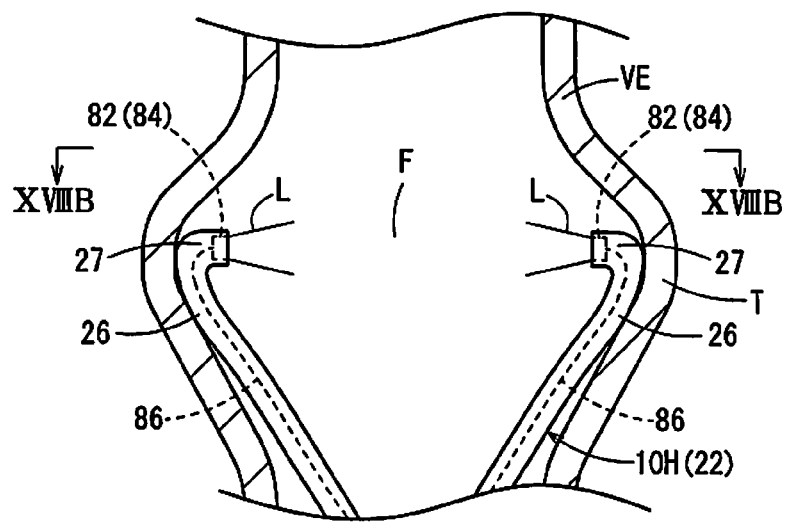
FIG. 18A is a view showing a state where a pair of arms of the treatment device of FIG. 17 is expanded within a vein.

As shown in FIG. 18A, the treatment device 10H is provided with the irradiation sections 82 inside of distal end portions 27 of a pair of arms 26. Thus, two irradiation sections 82 are provided. The irradiation sections 82 each include a lens 84, and they apply the laser beam L, which is transmitted by way of two optical fibers 86, toward the inner side of the pair of arms 26.

The optical fibers 86 are disposed inside the pair of arms 26 and inside a support 24, and each have one end connected to or disposed proximate to the lens 84. In addition, the optical fibers 86 are led out via a proximal end of the support 24, to be connected to a laser beam source 88. Note that the optical fibers 86 may be laid along outer surfaces of the pair of arms 26 and the support 24.

The laser beam L to be applied here, namely, the laser beam L generated by the laser beam source 88 may have a wavelength selected, for example, from among wavelengths of 810 nm, 940 nm, 1,064 nm, 1,320 nm, 1,470 nm and 2,000 nm.

A treatment method (body lumen occlusion method) by use of the treatment device 10H will now be described below, while taking up a varicose vein as an example.

In the method of using the treatment device 10H, first, an insertion step is conducted in the same manner as in the method of using the treatment device 10A. Specifically, the treatment device 10H with the pair of arms 26 stored in a shaft 18 is inserted into a vein VE through an introducer sheath, and a distal portion of the treatment device 10H is delivered to a treatment site T of the vein VE under ultrasound guidance.

Figure 18B:
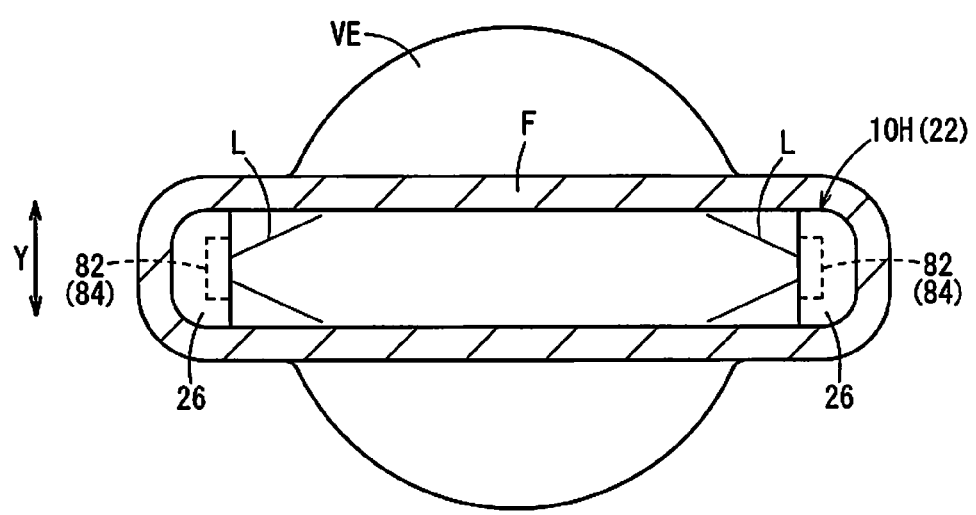
FIG. 18B is a sectional view taken along line XVIIIB-XVIIIB of FIG. 18A.

Next, a flattening step of forming the vein VE with a flat portion F by expanding the pair of arms 26 is carried out (see FIGS. 18A and 18B). Note that FIG. 18B is a sectional view taken along line XVIIIB-XVIIIB of FIG. 18A.

Subsequently, an irradiation step is conducted in which the laser beams L are radiated through the lenses 84 constituting the irradiation sections 82 toward an inner peripheral surface of the flat portion F of the vein VE so as to heat the flat portion F, thereby ablating the flat portion F. This irradiation step can be said to be an administering step of administering toward the flat portion F a treatment which acts to occlude the flat portion F (in this case, light energy). The laser beam L transmitted through the optical fibers 86 is radiated in the manner of being diffused in the thickness direction of the flat portion forming section (in a Y direction) by the lenses 84, whereby the inner peripheral surface of the flat portion F can be efficiently irradiated with the laser beams L.

Next, a moving step is performed in which the pair of arms 26 in the expanded (spread-apart) state is moved along the body lumen. Specifically, while keeping the pair of arms 26 in the expanded state and while radiating the laser beams L toward the flat portion F, the treatment device 10H as a whole is moved proximally, over a range where treatment is needed, and the treatment device 10H is stopped in a predetermined position. After the treatment of the vein VE over the desired range is carried out, the irradiation with the laser beams L is stopped.

Thereafter, the pair of arms 26 is re-stored into the shaft 18 (storing step), and the treatment device 10H is drawn out of the living body (the vein VE) (drawing-out step).

According to the treatment device 10H, the flat portion F formed in the body lumen by the flat portion forming section 22 is irradiated with the laser beams L so as to denature the tissue of the flat portion F, and, therefore, the body lumen can be occluded in a suitable manner.

Figure 19:
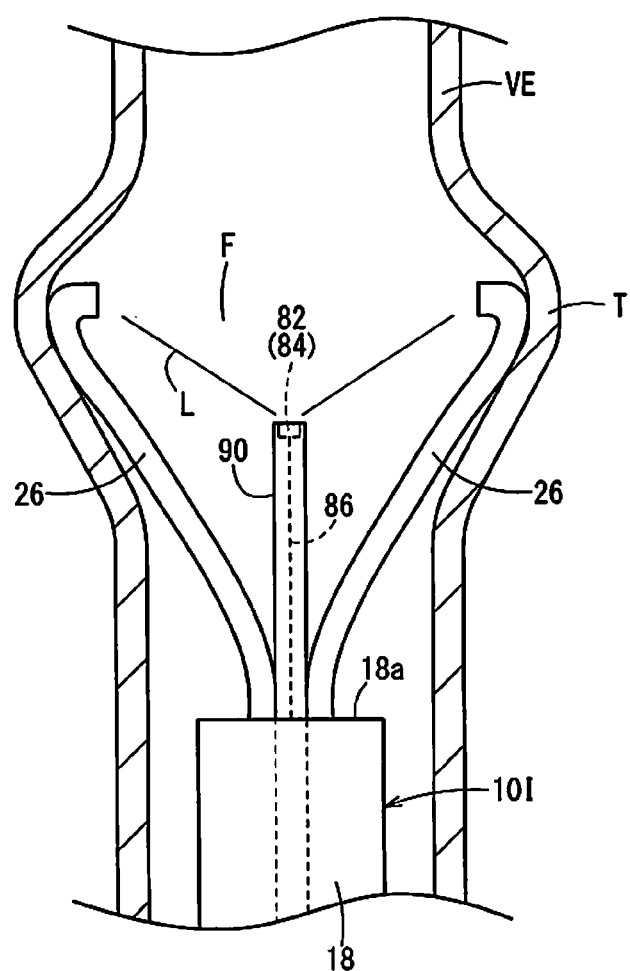
FIG. 19 is a view showing a state where a pair of arms of a still further treatment device is expanded within a vein and where a flat portion of the vein is irradiated with a laser beam.

There may be adopted such a configuration as a treatment device 10I depicted in FIG. 19 wherein an optical fiber 86 is disposed along a flexible elongated (rod-shaped) support member 90, and a lens 84 as an irradiation section 82 is mounted to a distal end of the support member 90. In this case, the optical fiber 86 may be inserted in the support member 90 or fixed to an outer surface of the support member 90. The support member 90 is inserted in a shaft 18 of a catheter 12 in the manner of being able to advance and recede, and its distal end portion with the lens 84 mounted thereto can be protruded distally from a distal end opening 18a of the shaft 18.

A method of using the treatment device 10I will now be described below, referring principally to the points in which this method differs from the method of using the treatment device 10H described above.

After a vein VE is formed with a flat portion F by expanding a pair of arms 26 in a treatment site T of the vein VE (namely, after a flattening step), an proximate-setting step is carried out in which the support member 90 is protruded from the distal end opening 18a of the shaft 18 so as to set the lens 84 proximate to the flat portion F of the vein VE.

Subsequently, an irradiation step (administering step) and a moving step are performed, like in the method of using the treatment device 10H. Note that in the case of the treatment device 10I, the laser beam L transmitted through the optical fiber 86 is radiated while being diffused in the width direction and the thickness direction of a flat portion forming section 22 by the lens 84. As a result, an inner peripheral surface of the flat portion F can be effectively irradiated with the laser beam L.

Thereafter, the pair of arms 26 and the support member 90 are re-stored into the shaft 18 (storing step), and the treatment device 10I is drawn out of the living body (the vein VE) (drawing-out step).

Figure 20:
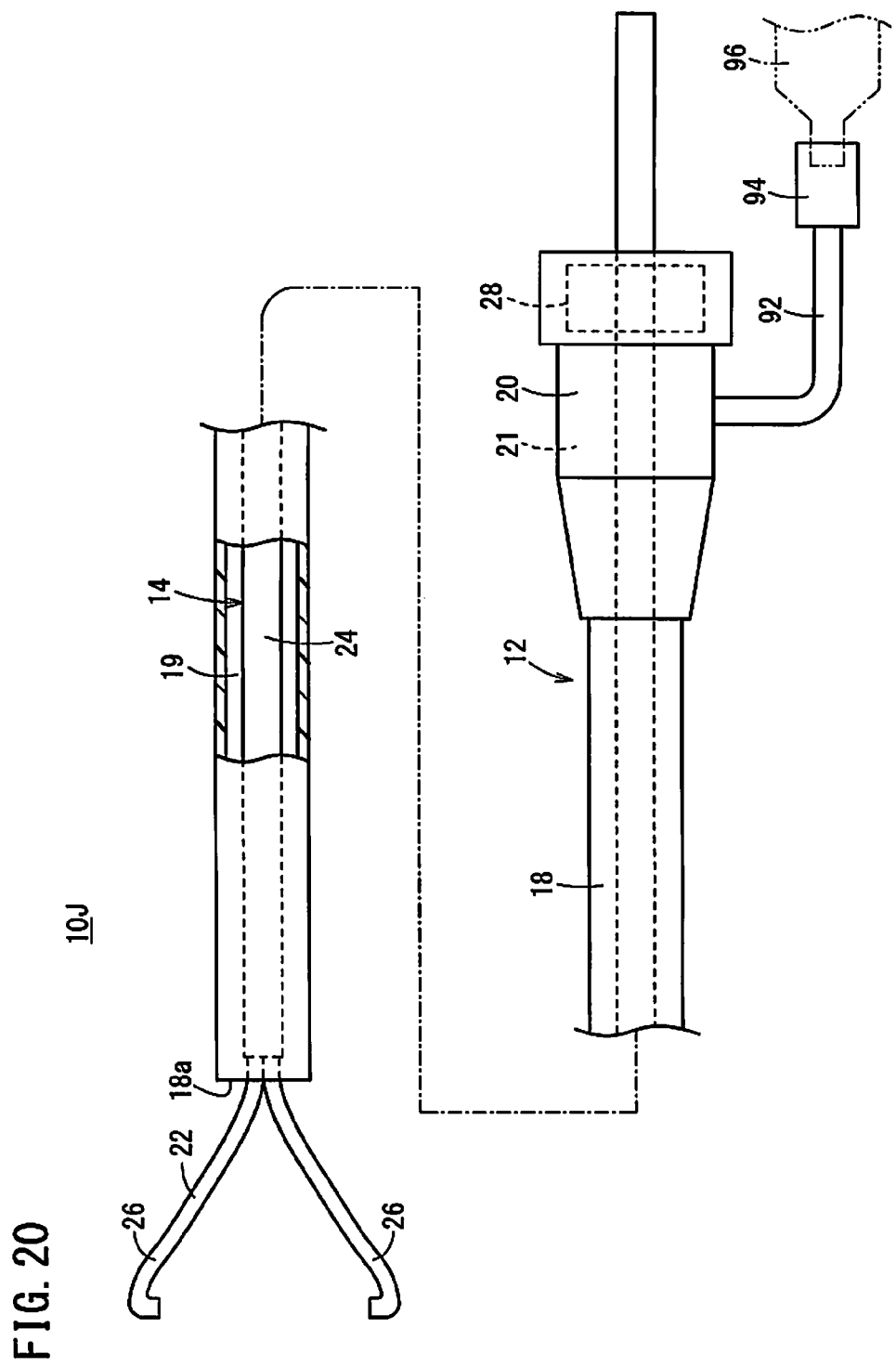
FIG. 20 is a partially omitted schematic view of yet another treatment device.

FIG. 20 is a partly omitted schematic view of still another treatment device 10J. This treatment device 10J is configured in that it does not include a component corresponding to the electrode section 16 of the treatment device 10A shown in FIG. 1, etc. and that it includes a branch tube 92 connected to a catheter 12. The branch tube 92 is connected at its one end to a hub 20 of the catheter 12, and is provided with a connector 94 at its other end. A lumen of the branch tube 92 communicates with a lumen of the catheter 12. To the connector 94 can be connected a supply device 96 (e.g., syringe) filled with a sclerosing agent M.

The sclerosing agent M is a medicinal liquid having a function of inducing a trauma in a blood vessel wall, thereby causing thrombus formation. Examples of the sclerosing agent M include polidocanol.

Now, a treatment method (body lumen occlusion method) by use of the treatment device 10J will be described below, while taking up treatment of a varicose vein as an example.

Figure 21A:
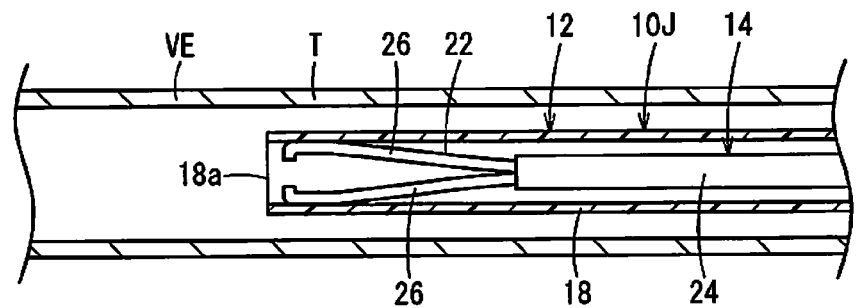
FIG. 21A is a first view for explaining a method of using the treatment device of FIG. 20.

First, the treatment device 10J with a pair of arms 26 stored in a shaft 18 is provided. Next, an insertion step is conducted in the same manner as in the case of using the treatment device 10A described above. Specifically, through an introducer sheath made to puncture a patient, the treatment device 10J is inserted into a vein VE in which an onset of a varicose vein has occurred. Then, the treatment device 10J is advanced under ultrasound guidance so as to deliver a distal portion of the treatment device 10J to a treatment site T (target site) of the vein VE, as shown in FIG. 21A.

Figure 21B:
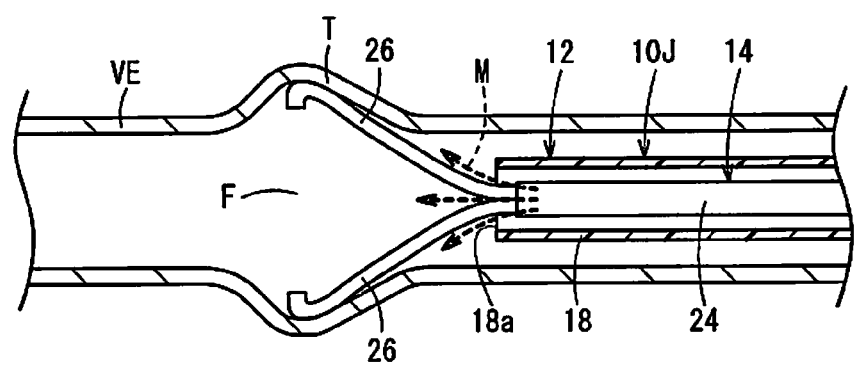
FIG. 21B is a second view for explaining the method of using the treatment device of FIG. 20.

Next, a flattening step of deforming a body lumen into a form having a flat portion F is carried out. Specifically, as shown in FIG. 21B, the pair of arms 26 is expanded, thereby forming the vein VE with the flat portion F.

Subsequently, a sclerosing agent supplying step is conducted in which a sclerosing agent M supplied from the supply device 96 connected to the connector 94 is made to flow through the branch tube 92 and the catheter 12, and then through a lumen 19 of the shaft 18, to be discharged via a distal end opening 18a of the shaft 18. The sclerosing agent supplying step can be said to be an administering step of administering toward the flat portion F a treatment which acts to occlude the flat portion F (in this case, the sclerosing agent M). By the sclerosing agent supplying step, the sclerosing agent M is supplied to the flat portion F of the vein VE. Thus, the lumen 19 and the distal end opening 18a of the shaft 18 function as a sclerosing agent supplying section for supplying the sclerosing agent M toward the flat portion F.

Figure 21C:
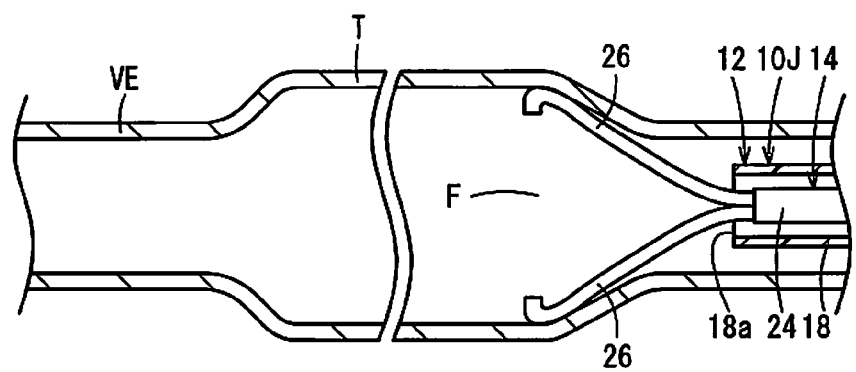
FIG. 21C is a third view for explaining the method of using the treatment device of FIG. 20.

Next, a moving step is carried out in which the pair of arms 26 in the expanded state is moved along the body lumen. Specifically, with the pair of arms 26 kept in the expanded state, as depicted in FIG. 21C, the treatment device 10J as a whole is moved proximally at a fixed speed and over a range where treatment is needed, and the treatment device 10J is stopped in a predetermined position. Note that the sclerosing agent M may be discharged only once before the treatment device 10J as a whole is moved proximally or may further be discharged once or multiple times while the treatment device 10J as a whole is being moved proximally.

Alternatively, the discharge of the sclerosing agent M may be started before the proximal movement of the treatment device 10J as a whole and is continuously performed at a predetermined flow rate during the proximal movement. In this case, the discharge of the sclerosing agent M is stopped when the movement of the treatment device 10J is stopped.

The blood vessel wall of the vein VE to which the sclerosing agent M has been applied suffers a trauma under the action of the sclerosing agent M, whereby a thrombus is formed, so that the vein VE thus treated will come to be occluded. After the vein VE is treated over the desired range, the pair of arms 26 is re-stored into the shaft 18 (storing step), and the treatment device 10J is drawn out of the living body (the vein VE) (drawing-out step).

According to the treatment device 10J, the sclerosing agent M is applied after the body lumen is formed with the flat portion F, so that the flat portion F of the body lumen can be occluded efficiently. In addition to this, other effects similar to those of the treatment device 10A shown in FIG. 1, etc. can also be obtained with the treatment device 10J.

Figure 22:
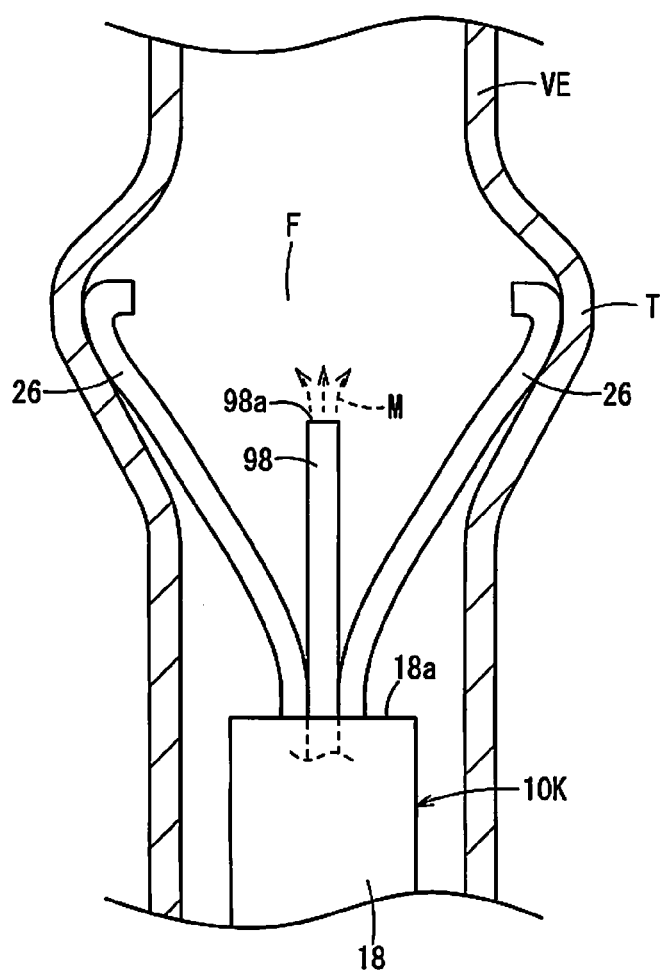
FIG. 22 is view showing a state where a pair of arms of a yet further treatment device is expanded within a vein and where a sclerosing agent is discharged toward a flat portion of the vein.

As in a case of a treatment device 10K depicted in FIG. 22, a flexible elongated tube 98 may be used to supply a sclerosing agent M to a flat portion F of a vein VE. The tube 98 is inserted in a shaft 18 of a catheter 12 in the manner of being able to advance and recede, and its distal end can be protruded distally from a distal end opening 18a of the shaft 18.

A method of using the treatment device 10K will be described below, while referring principally to the points in which this method differs from the method of using the treatment device 10J described above.

After a vein VE is formed with a flat portion F by expanding a pair of arms 26 in a treatment site T of the vein VE (namely, after a flattening step), a sclerosing agent supplying step (administering step) is conducted in which the tube 98 is protruded from the distal end opening 18a of the shaft 18, and a sclerosing agent M is discharged via a distal end opening 98a of the tube 98 toward the flat portion F of the vein VE. Thus, the tube 98 and its distal end opening 98a function as a sclerosing agent supplying section for supplying the sclerosing agent M toward the flat portion F.

In addition, like in the method of using the treatment device 10J, a moving step is carried out in which the pair of arms 26 in its expanded state is moved along a body lumen.

After the vein VE is treated over a desired range, the pair of arms 26 and the tube 98 are re-stored into the shaft 18 (storing step), and the treatment device 10K is drawn out of the living body (the vein VE) (drawing-out step).

According to the treatment device 10K, the sclerosing agent M can be discharged from a position nearer to the flat portion F of the vein VE and, therefore, the sclerosing agent M can be supplied to the flat portion F more effectively, as compared with the case of the treatment device 10J shown in FIG. 20.

Figure 23:
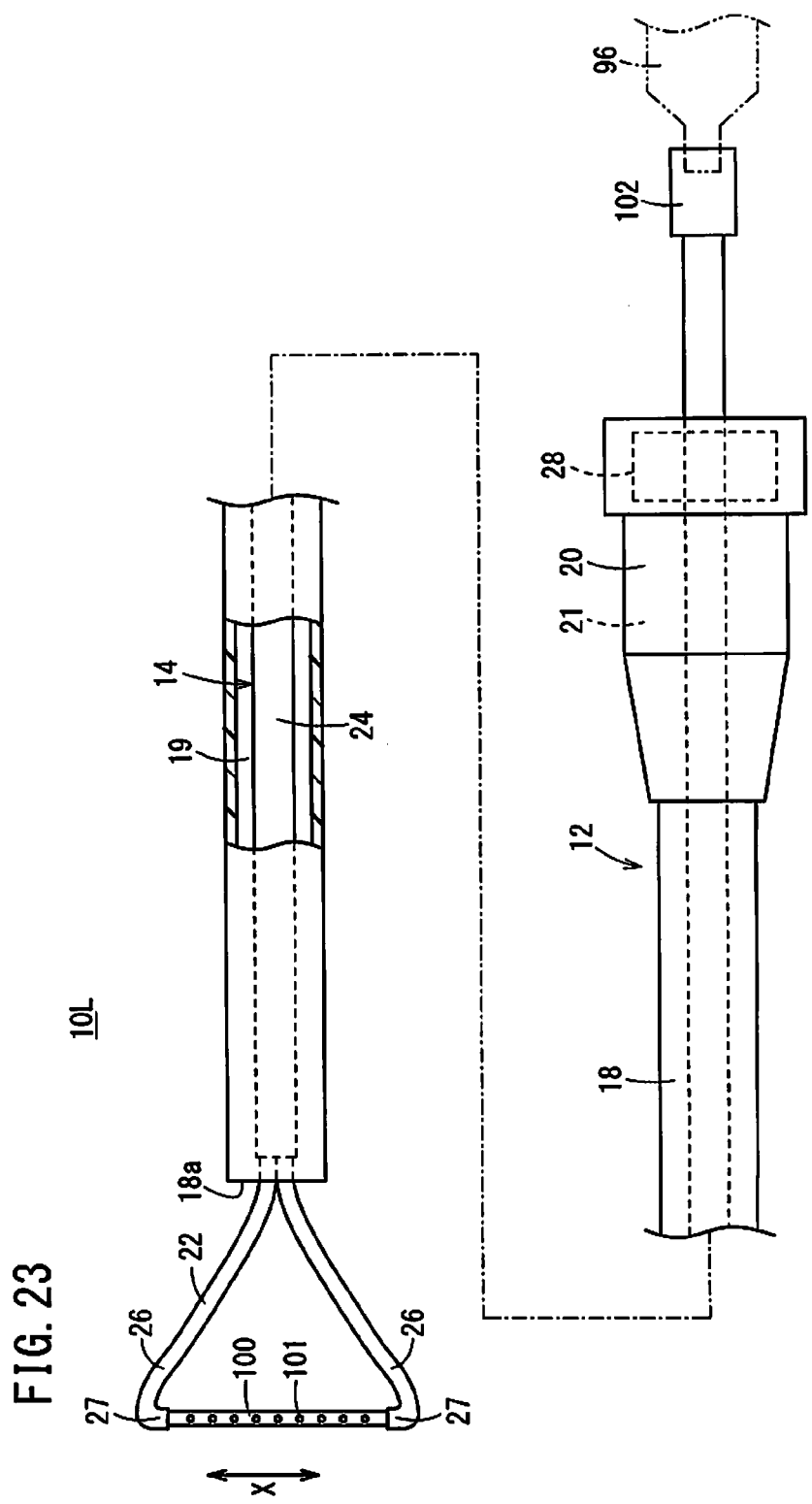
FIG. 23 is a partially omitted schematic view of still another treatment device.

FIG. 23 is a partly omitted schematic view of a still further treatment device 10L. This treatment device 10L shares with the treatment device 10J of FIG. 20 a common feature of supplying a sclerosing agent M to a flat portion F formed in a vein VE. On the other hand, this treatment device 10L differs from the treatment device 10J in that it includes a supply tube 100 supported by distal end portions 27 of a pair of arms 26, and that a support 24 is provided at its proximal end with a connector 102 to which can be connected a supply device 96 filled with the sclerosing agent M.

Figure 24A:
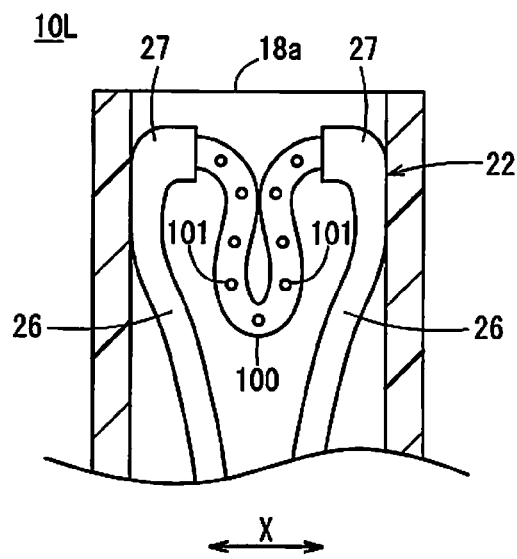
FIG. 24A is a partially sectional view showing a state where a pair of arms of the treatment device of FIG. 23 is stored in a shaft.
Figure 24B:
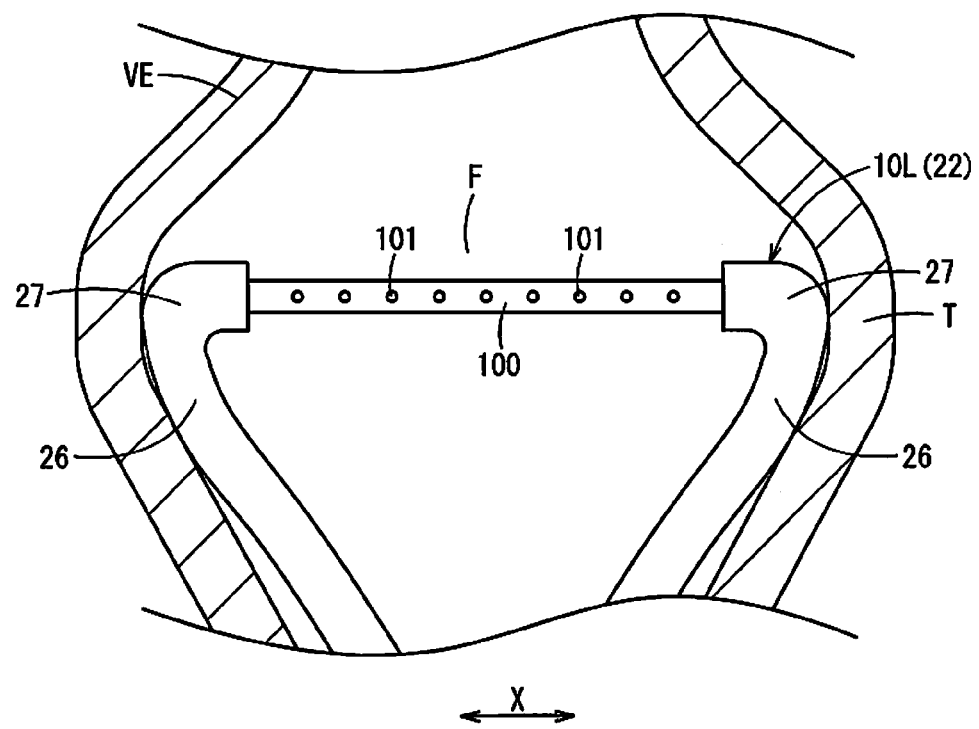
FIG. 24B is a view showing a state where the pair of arms of the treatment device of FIG. 23 is expanded within a vein.

The supply tube 100 is flexible, and is deformable following up to the degree of opening (expansion) of the pair of arms 26. When the pair of arms 26 is in its closed state inside a shaft 18 as shown in FIG. 24A, therefore, the supply tube 100 is stored in a bent state inside the shaft 18. When the pair of arms 26 is protruded from a distal end opening 18a of the shaft 18 and expanded widthwise (in an X direction) as shown in FIG. 24B, on the other hand, the supply tube 100 assumes a rectilinear shape between the distal end portions 27 of the pair of arms 26 by being pulled by the pair of arms 26 (or by its own elastic restoring force).

The supply tube 100 is provided with a plurality of blowoff ports 101 for blowing off the sclerosing agent M therethrough. The blowoff ports 101 communicate with a lumen of the supply tube 100. In the illustrated example, the plurality of blowoff ports 101 is provided along the lengthwise direction of the supply tube 100. The blowoff ports 101 are provided on both sides with respect to the thickness direction of a flat portion forming section 22.

A method of using the treatment device 10L will be described below, referring principally to the points in which this method differs from the method of using the treatment device 10J described above.

First, the treatment device 10L with the pair of arms 26 and the supply tube 100 stored in the shaft 18 is provided (see FIG. 24A). Next, a distal portion of the treatment device 10L is delivered to a treatment site T of a vein VE, in the same manner as in the insertion step in the method of using the treatment device 10J.

Subsequently, a flattening step of deforming a body lumen into a form having a flat portion F is conducted. Specifically, the pair of arms 26 is protruded from the distal end opening 18a of the shaft 18, and, upon this, the pair of arms 26 is expanded, thereby forming the vein VE with the flat portion F. In this instance, the supply tube 100 assumes a rectilinear shape between the distal end portions 27 of the pair of arms 26, and is positioned inside the flat portion F as shown in FIG. 24B.

Next, a sclerosing agent supplying step (administering step) is conducted in which the sclerosing agent M is discharged toward the flat portion F of the vein VE. Specifically, the sclerosing agent M is discharged from the supply device 96 connected to the connector 102, and is made to flow through the support 24 and the arms 26 into the supply tube 100, to be discharged via the blowoff ports 101 provided in the supply tube 100. As a result the sclerosing agent M is supplied to the flat portion F of the vein VE. Thus, the blowoff ports 101 provided in the supply tube 100 function as a sclerosing agent supplying section for supplying the sclerosing agent M to the flat portion F.

Subsequently, like in the method of using the treatment device 10J, a moving step is conducted in which the pair of arms 26 in its expanded state is moved proximally along the body lumen.

After the vein VE is treated over a desired range, the pair of arms 26 and the supply tube 100 are re-stored into the shaft 18 (storing step), and the treatment device 10L is drawn out of the living body (the vein VE) (drawing-out step).

According to the treatment device 10L configured as above, the supply tube 100 formed with the blowoff ports 101 is provided between the distal ends of the arms 26, so that the sclerosing agent M can be blown off toward the flat portion F formed in the vein VE from within the flat portion F. Therefore, the flat portion F can be occluded effectively.

Particularly in the case of the treatment device 10L, both ends of the supply tube 100 are connected to the respective distal end portions 27 of the pair of arms 26, so that the supply tube 100 is reliably positioned inside the flat portion F, upon the expansion of the pair of arms 26 inside the body lumen. Accordingly, both the expansion of the pair of arms 26 and the positioning of the supply tube 100 inside the flat portion F can be carried out by a single operation.

Note that while the treatment device 10K (FIG. 22) and the treatment device 10L (FIG. 23) have been described above while taking as an example a case where the sclerosing agent M is used as an occluding material for occluding a body lumen, an adhesive (embolizing agent) may be used in place of the sclerosing agent M. In this case, in the treatment device 10K (or the treatment device 10L), the adhesive is discharged via the distal end opening 98a of the tube 98 (or the blowoff ports 101 of the supply tube 100). The adhesive is liquid before the discharge, and becomes solid (or semi-solid) by curing after the discharge.

The adhesive may be of polymerization type or of precipitation type. Examples of the adhesive which can be used here include cyanoacrylate adhesives, polyvinyl alcohol adhesives, polyurethane adhesives, gelatin adhesives, and fibrin adhesives (fibrin glue). Among these adhesives, particularly preferable are cyanoacrylate adhesives because they exhibit an embolizing effect immediately upon discharge from the shaft 18. Examples of the cyanoacrylate adhesives include NBCA (N-butyl-2-cyanoacrylate) and Onyx (registered trademark).

Methods of using the treatment device 10K (FIG. 22) and the treatment device 10L (FIG. 23) in the case where an adhesive is applied are substantially the same as the aforementioned methods of using the treatment device 10K and the treatment device 10L. It is to be noted here, however, that in the case of applying an adhesive, it is preferable for the adhesive to be continuously discharged via the distal end opening 98a of the tube 98 (or via the blowoff ports 101 of the supply tube 100) at a predetermined flow rate during when the treatment device 10K as a whole (or the treatment device 10L as a whole) is moved proximally at a fixed speed, with the pair of arms 26 kept in the expanded state inside a body lumen.

Figure 25:
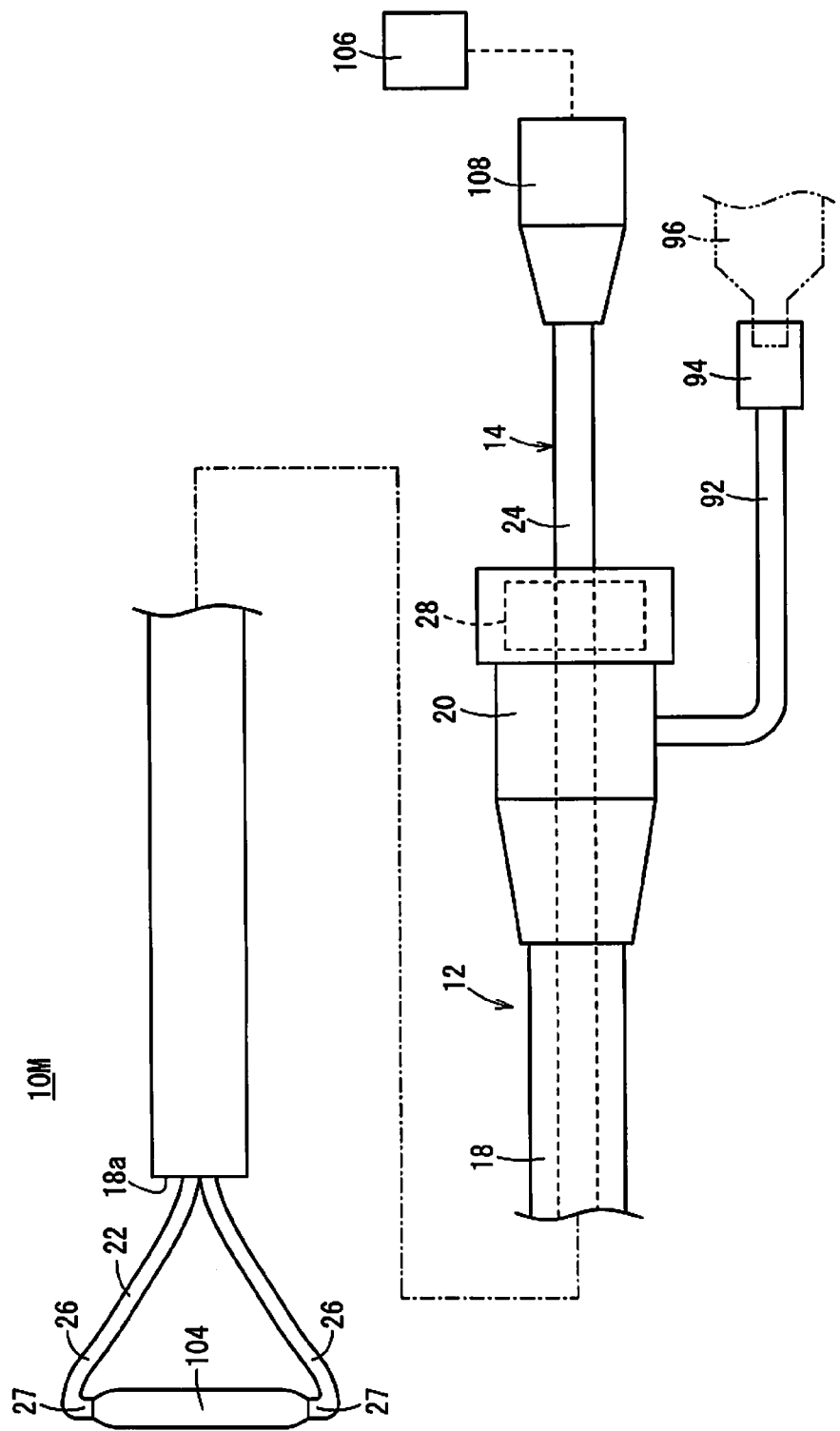
FIG. 25 is a partially omitted schematic view of still another treatment device.
Figure 26:
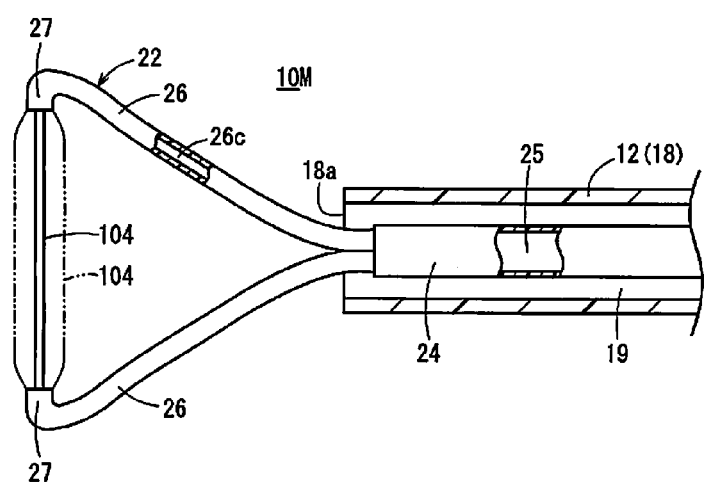
FIG. 26 is a partially sectional view of a distal portion of the treatment device of FIG. 25.
Figure 27:
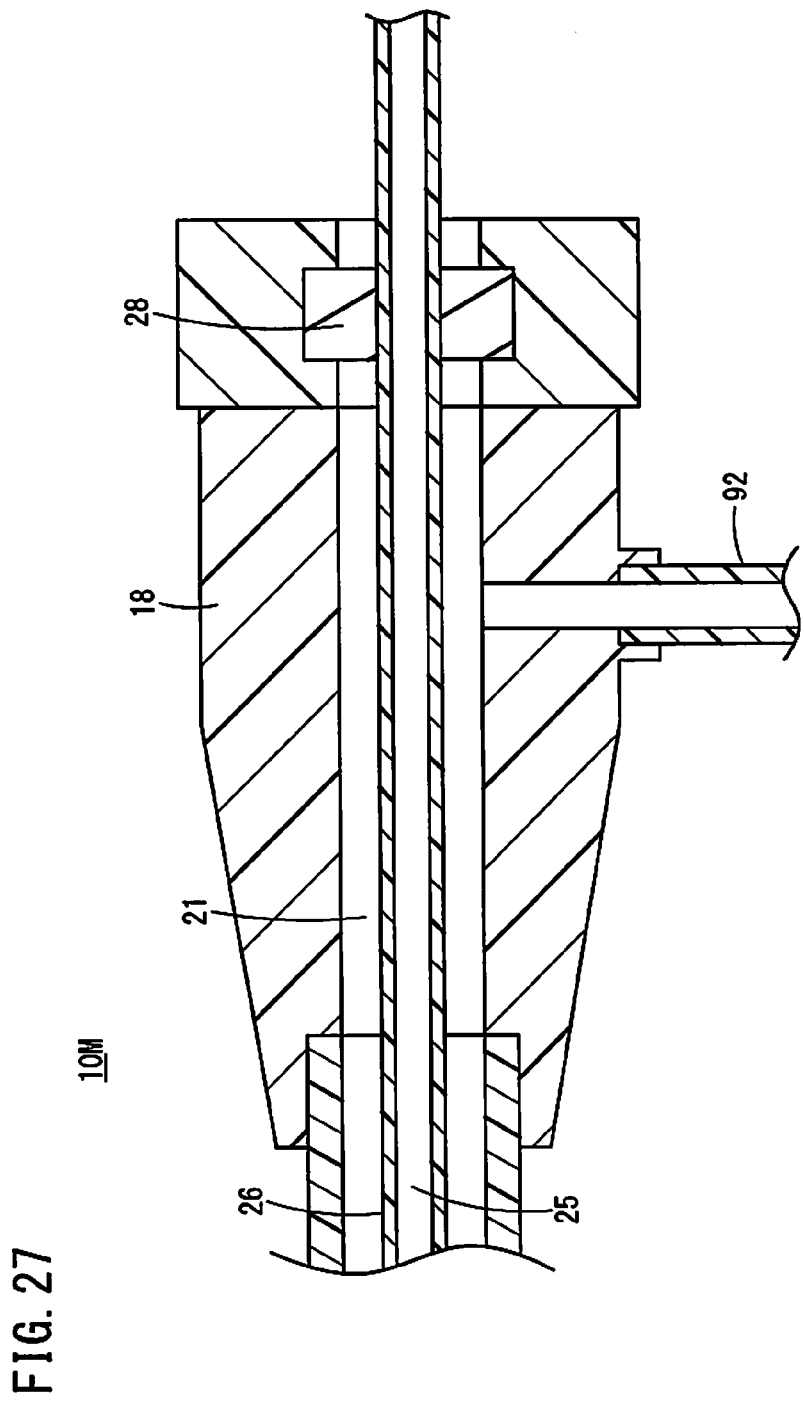
FIG. 27 is a sectional view of a proximal portion of the treatment device of FIG. 25.

FIG. 25 is a partly omitted schematic view of another treatment device 10M. FIG. 26 is a partially sectional view of a distal portion of the treatment device 10M, and FIG. 27 is a sectional view of a proximal portion of the treatment device 10M.

As illustrated in FIG. 25, this treatment device 10M is a modification of the treatment device 10J shown in FIG. 20, and includes a balloon 104 supported by distal end portions 27 of a pair of arms 26. The balloon 104 functions as an occluding section which is inflatable and, upon inflation, can temporarily occlude a lumen of a flat portion F formed in a body lumen. In FIG. 25, the balloon 104 is depicted in its inflated state.

The balloon 104 is deflated (non-inflated) in an initial state, and can be inflated as an inflating fluid is introduced therein. The inflating fluid to be supplied into the balloon 104 may be either liquid or gas. Examples of the inflating fluid include physiological saline solution and air. One end and the other end of the balloon 104 are connected to the respective distal end portions 27 of the pair of arms 26. As depicted in FIG. 26, a lumen 26c of the arm 26 communicates with a lumen of the balloon 104 and a lumen 25 of a support 24.

As shown in FIG. 25, the support 24 is provided at its proximal end with a hub 108 (connector) to which can be connected an inflation/deflation operating device 106. The inflation/deflation operating device 106 is a device for supplying the inflating fluid into the balloon 104 or discharging the inflating fluid out of the balloon 104, through the lumen 25 of the support 24 and the lumens 26c of the arms 26.

The inflation/deflation operating device 106 may be composed, for example, of a syringe, an indeflator or the like. In the case where the inflation/deflation operating device 106 is a syringe, an operator causes the inflating fluid to flow out of the syringe by pushing a plunger (not shown) forward, and sucks out the inflating fluid by letting a hand off the plunger (or by pulling the plunger).

As the inflating fluid is introduced into the balloon 104, the balloon 104 is inflated as depicted in imaginary lines in FIG. 26. When the inflating fluid is discharged from within the balloon 104, the balloon 104 is deflated as depicted in solid lines in FIG. 26.

The balloon 104 is preferably formed of an elastic (expandable and contractible) material. Examples of the elastic material include various rubber materials such as natural rubber, butyl rubber, isoprene rubber, butadiene rubber, styrene-butadiene rubber, silicone rubber, etc., various thermoplastic elastomers based on polyurethane, polyester, polyamide, olefin, styrene or the like, and mixtures of them. Note that the balloon 104 may be formed of a material which is not elastic.

Now, a body lumen treatment method by use of the treatment device 10M (a body lumen occlusion method according to a first embodiment) will be described below, while taking up treatment of a varicose vein as an example.

Figure 28A:
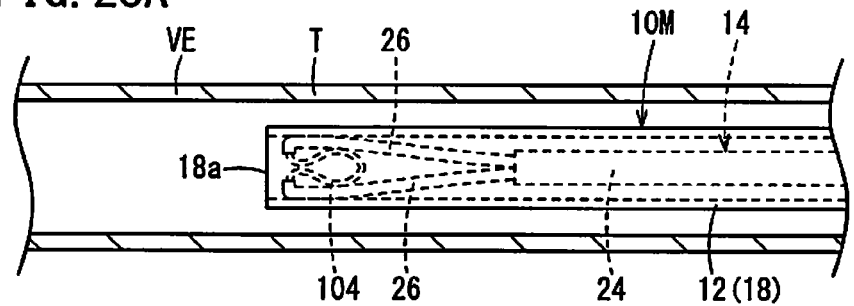
FIG. 28A is a first view for explaining a method of using the treatment device of FIG. 25.

First, an insertion step is conducted in which the treatment device 10M is inserted into a body lumen so that a distal portion of the treatment device 10M reaches a treatment site T (target site). Specifically, the treatment device 10M with a flat portion forming section 22 (the pair of arms 26) and the balloon 104 stored in a shaft 18 is inserted into a vein VE through an introducer sheath. Then, the distal portion of the treatment device 10M is delivered to the treatment site T of the vein VE under ultrasound guidance (see FIG. 28A). In this case, in the shaft 18, the balloon 104 is present in a bent state, together with the pair of arms 26 which is in a closed state.

Figure 28B:
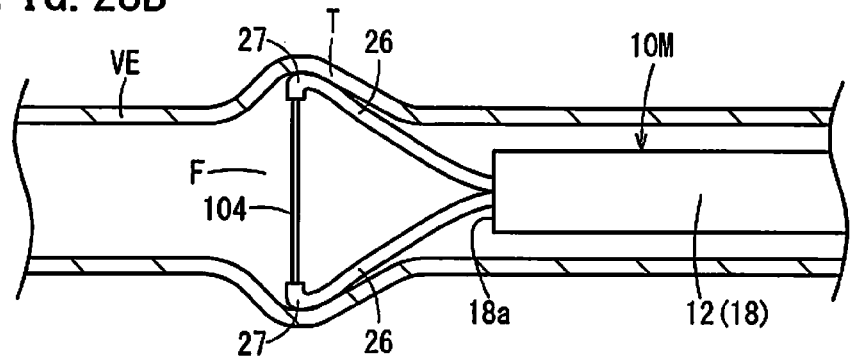
FIG. 28B is a second view for explaining the method of using the treatment device of FIG. 25.

Next, a flattening step of deforming the body lumen into a form having a flat portion F is conducted. Specifically, as shown in FIG. 28B, the pair of arms 26 is protruded from a distal end opening 18a of the shaft 18 and, upon this, the arms 26 are expanded, thereby forming the vein VE with the flat portion F. In this instance, the balloon 104 assumes a rectilinear shape between the distal end portions 27 of the arms 26, and is disposed inside of the flat portion F. Note that at the time of forming the vein VE with the flat portion F, the degree of flattening of the vein VE may be checked by use of ultrasonic means.

Figure 28C:
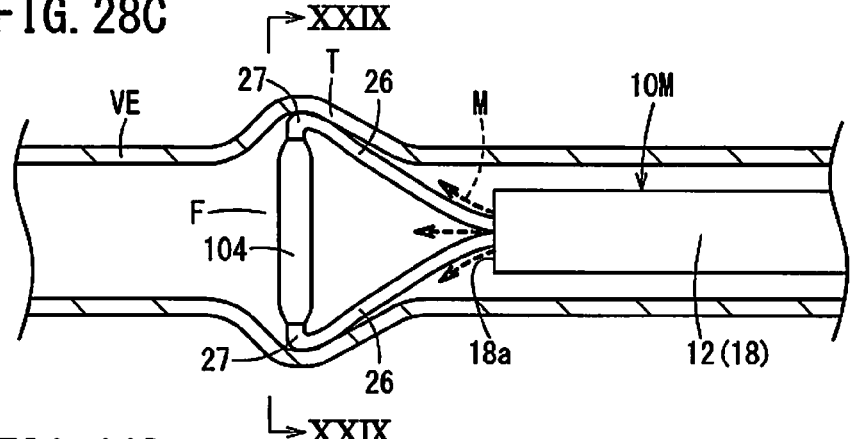
FIG. 28C is a third view for explaining the method of using the treatment device of FIG. 25.

Subsequently, an occluding step of temporarily occluding the lumen of the flat portion F is carried out. Specifically, under an operation of the inflation/deflation operating device 106 connected to the hub 108, the inflating fluid is supplied into the balloon 104, thereby inflating the balloon 104 at a predetermined pressure, as depicted in FIG. 28C. By this operation, a flow path formed inside the lumen of the flat portion F is temporarily put in an occluded (closed) state.

In this case, it is preferable to control the pressure so that the balloon 104 is inflated to a thickness (diametral size) comparable to the thickness (dimension in a Y direction) of the arms 26. In the case where the balloon 104 is formed from an elastic (expandable and contractible) material, it is easy for the balloon 104 in the inflated state and an inner surface of the flat portion F to make secure contact with each other, so that a blood flow at the flat portion F can be blocked easily and effectively.

In addition, in the case where the balloon 104 is formed from a material having a sufficiently elastic material, it is ensured that, even when the inflating fluid is supplied into the balloon 104 in an amount in excess of the amount for inflating the balloon 104 to the thickness of the lumen of the flat portion F formed by the expansion of the pair of arms 26, the balloon 104 will be inflated not in the thickness direction of the flat portion F but in the extending direction of the vein VE. Therefore, the thickness of the flat portion F can be maintained at the value attained upon the expansion of the pair of arms 26. Accordingly, such a supply of an excess of the inflating fluid as just-mentioned does not hinder the occlusion performed later by application of the sclerosing agent M.

Note that the occlusion by the balloon 104 is not restricted to a state in which the lumen of the flat portion F is perfectly closed with the balloon 104 without leaving any gap (100% occlusion), but includes a state in which most of the lumen of the flat portion F (for example, not less than 70% to 90% or not less than 95% of the cross-sectional area of the flow path in the flat portion F in the case where the occlusion by the balloon 104 is not applied) is closed.

Next, a sclerosing agent supplying step of supplying the sclerosing agent M toward the flat portion F is performed. Specifically, the sclerosing agent M is discharged from a supply device 96 connected to a connector 94, and is made to flow through the support 24, to be discharged via the distal end opening 18a of the shaft 18. As a result, the sclerosing agent M is supplied to the flat portion F of the vein VE. In this case, the sclerosing agent M may be discharged at least once or may be continuously discharged at a fixed flow rate.

Figure 28D:
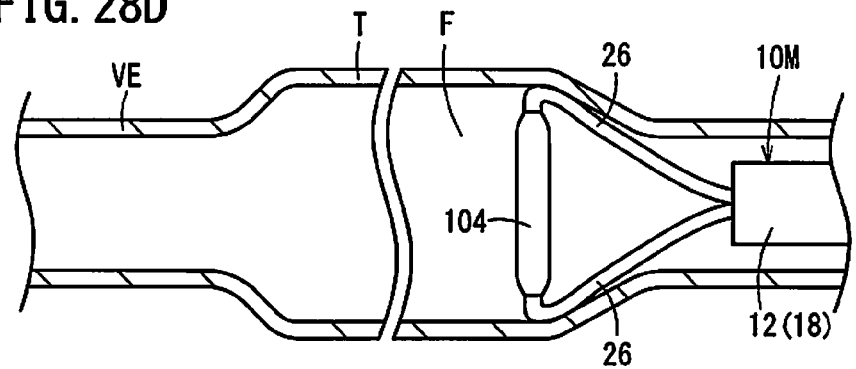
FIG. 28D is a fourth view for explaining the method of using the treatment device of FIG. 25.

After the sclerosing agent supplying step or concurrently with the sclerosing agent supplying step, a moving step is conducted in which the pair of arms 26 is moved proximally while being kept in the expanded state. Specifically, with the pair of arms 26 kept in the expanded state, as depicted in FIG. 28D, the treatment device 10M as a whole is moved proximally at a fixed speed and over a range where treatment is needed, and the treatment device 10M is stopped in a predetermined position. Note that the sclerosing agent M may be discharged multiple times during a period after the expansion of the balloon 104 and until the treatment device 10M is stopped in the predetermined position. In the case of a procedure pattern in which the sclerosing agent M is continuously discharged at a fixed flow rate, the discharge of the sclerosing agent M is also stopped when the movement of the treatment device 10M is stopped.

After the vein VE is treated over a desired range, the balloon 104 is deflated by discharging the inflating fluid out of the balloon 104 (contraction step). Thereafter, the pair of arms 26 and the balloon 104 are re-stored into the shaft 18 (storing step), and the treatment device 10M is drawn out of the living body (the vein VE) (drawing-out step).

According to the treatment device 10M configured as above, the balloon 104 functioning as an occluding section is disposed in the lumen of the flat portion F, whereby the flow path defined by the lumen of the flat portion F can be closed temporarily. This ensures that dilution of the sclerosing agent M is restrained, and the sclerosing agent M in a suitable concentration can be supplied to the flat portion F efficiently. Consequently, the occluding effect of the sclerosing agent M can be exhibited favorably, and the amount of the sclerosing agent M to be used can be reduced.

Besides, in the case of this treatment device 10M, it is possible to suitably close the lumen of the flat portion F, by controlling the inflation of the balloon 104.

Figure 30:
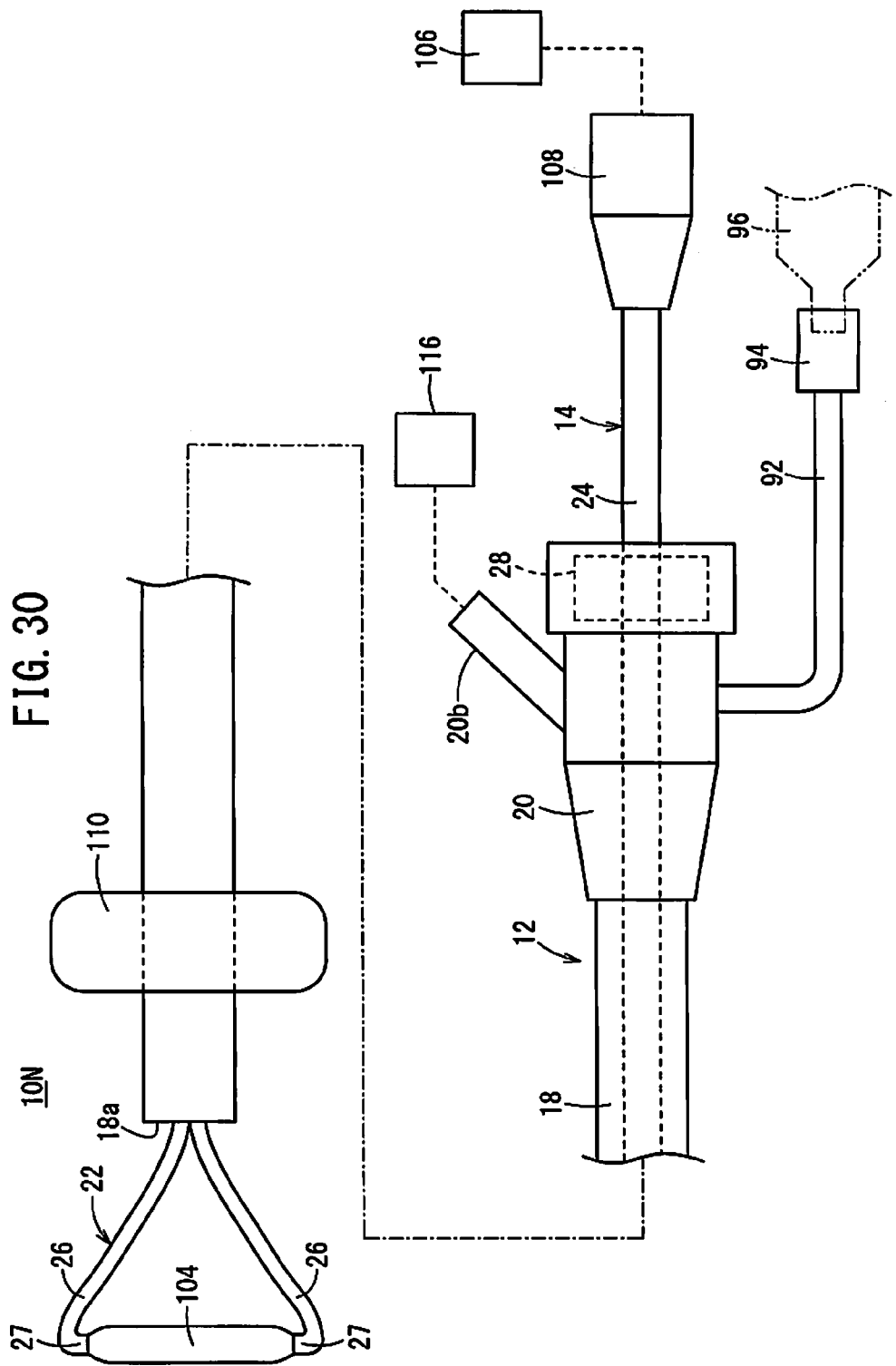
FIG. 30 is a partially omitted schematic view of a still further treatment device.
Figure 31:
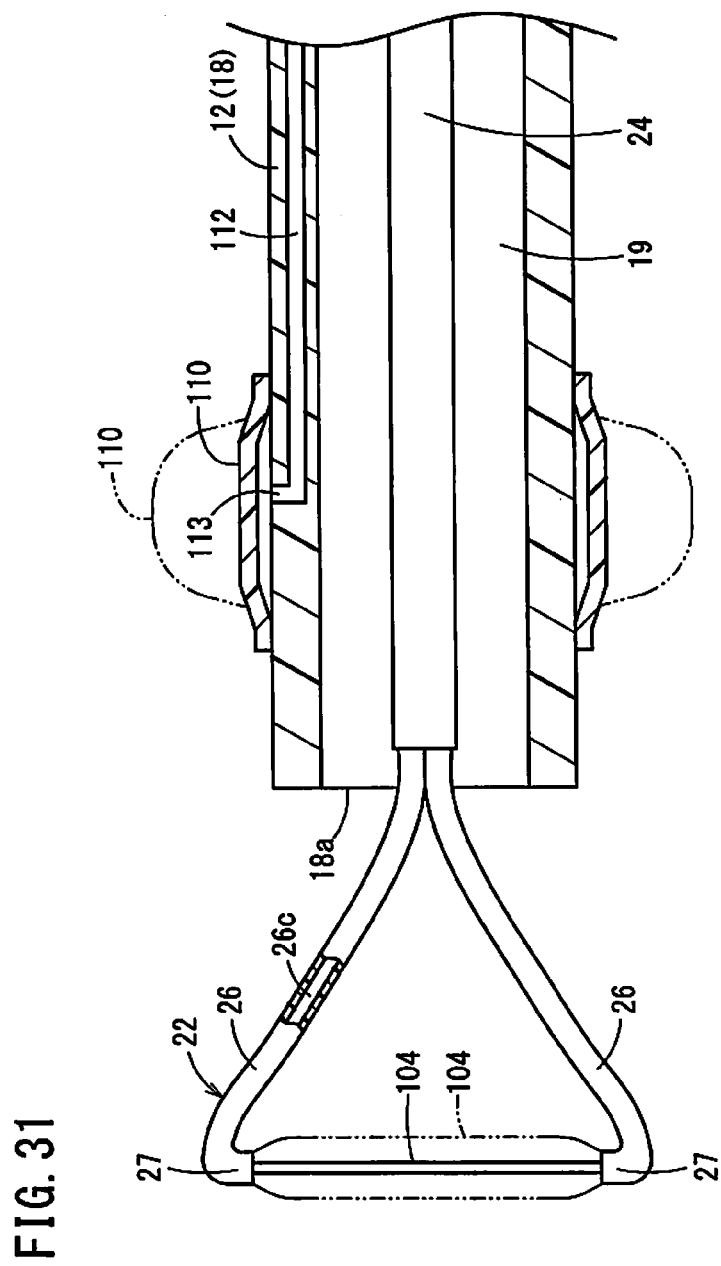
FIG. 31 is a partially sectional view of a distal portion of the treatment device of FIG. 30.
Figure 32:
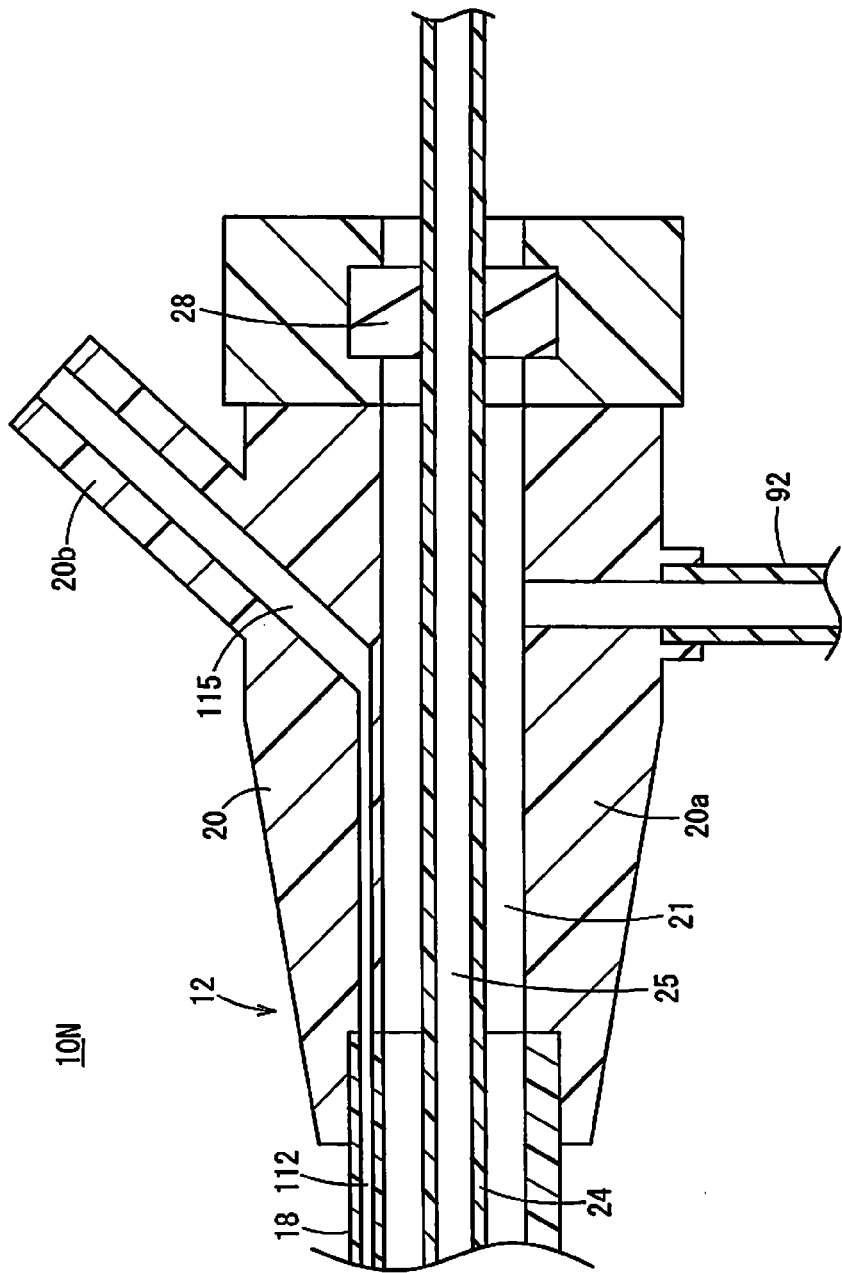
FIG. 32 is a sectional view of a proximal portion of the treatment device of FIG. 30.

FIG. 30 is a partially omitted schematic view of a treatment device 10N having a further configuration. FIG. 31 is a partially sectional view of a distal portion of the treatment device 10N, and FIG. 32 is a sectional view of a proximal portion of the treatment device 10N.

This treatment device 10N is a modification of the treatment device 10M shown in FIG. 25, and includes an inflatable balloon 110 around a peripheral portion of a shaft 18, in addition to a balloon 104 provided at a distal end of a flat portion forming section 22.

Hereinafter, the balloon 104 provided at the distal end of the flat portion forming section 22 will be referred to as the "first balloon 104," and the balloon 110 provided around the peripheral portion of the shaft 18 will be referred to as the "second balloon 110." The second balloon 110 functions as a second occluding section capable of temporarily occluding a gap between the shaft 18 and a body lumen.

The second balloon 110 is deflated (non-inflated) in an initial state, and can be inflated as an inflating fluid is introduced thereinto. The inflating fluid to be supplied into the second balloon 110 may be of the same kind as or of a different kind from an inflating fluid to be supplied into the first balloon 104.

The second balloon 110 is preferably provided at or in the vicinity of a distal portion of the shaft 18. The second balloon 110 extends circumferentially in an annular form along the peripheral portion of the shaft 18. A passage 112 permitting the inflating fluid to flow therethrough is defined inside the shaft 18, and the passage 112 communicates with a lumen of the second balloon 110. The passage 112 is provided at its distal end with a side hole 113 exposed to the lumen of the second balloon 110.

Note that while the passage 112 is formed in a wall surrounding a lumen 19 of the shaft 18 in FIG. 31, such a configuration as this may be replaced by a configuration wherein the shaft 18 is composed of an inner tube and an outer tube and wherein the passage 112 is defined between the inner tube and the outer tube.

In FIG. 31, the second balloon 110 in its deflated state is depicted in solid lines. As the inflating fluid is supplied through the passage 112 into the second balloon 110, the second balloon 110 is inflated radially outward as shown in imaginary lines in FIG. 31.

As illustrated in FIG. 32, the passage 112 extends along the axial direction of the shaft 18, and reaches a proximal end plane of the shaft 18. A hub 20 of a catheter 12 is provided with a branching section 20b branching from a hub main body 20a, and is formed therein with a passage 115 communicating with the passage 112 in the shaft 18. The passage 115 is formed in the hub main body 20a and in the branching section 20b, and is open at a free end of the branching section 20b. Note that the branching section 20b, which is formed integral with the hub main body 20a, may be replaced by a flexible tube (a tube similar to a branch tube 92) connected to the hub 20.

As depicted in FIG. 30, to the branching section 20b can be connected an inflation/deflation operating device 116 for inflating and deflating the second balloon 110. Hereinafter, an inflation/deflation operating device 106 for inflating and deflating the first balloon 104 will be referred to as the "first inflation/deflation operating device 106," and the inflation/deflation operating device 116 will be referred to as the "second inflation/deflation operating device 116." The second inflation/deflation operating device 116 is a device for supplying the inflating fluid into the second balloon 110 and discharging the inflating fluid out of the second balloon 110, through the hub 20 (the passage 115 provided inside the hub 20) and the shaft 18 (the passage 112 provided inside the shaft 18). Like the first inflation/deflation operating device 106, the second inflation/deflation operating device 116 may be composed, for example, of a syringe, an indeflator or the like.

The material forming the second balloon 110 can be selected from among the materials mentioned above as examples of the material forming the first balloon 104. The second balloon 110 may be formed from an elastic (expandable and contractible) material, or may be formed from a material which does not have elasticity.

Now, a body lumen treatment method by use of the treatment device 10N (a body lumen occlusion method according to a second embodiment) will be described below, while taking up treatment of a varicose vein as an example.

First, an insertion step is conducted in which the treatment device 10N is inserted into a body lumen so as to deliver a distal portion of the treatment device 10N to a treatment site T. Specifically, the treatment device 10N with the flat portion forming section 22 (a pair of arms 26) and the balloon 104 stored in the shaft 18 and with the first balloon 104 and the second balloon 110 being in their deflated state is inserted into a vein VE through an introducer sheath.

Figure 33A:
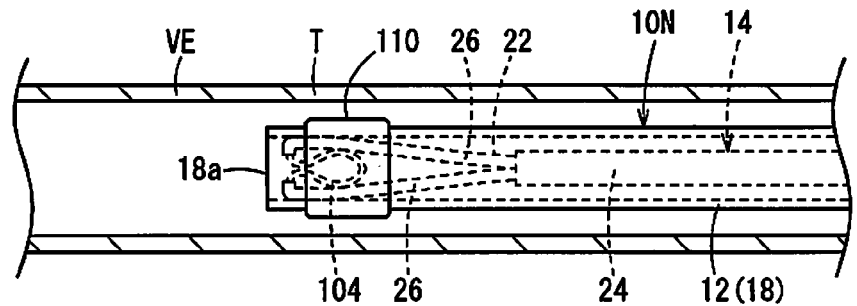
FIG. 33A is a first view for explaining a method of using the treatment device of FIG. 30.

Then, the distal portion of the treatment device 10N is delivered to a target site of the vein VE under ultrasound guidance (see FIG. 33A). In this case, in the shaft 18, the first balloon 104 is present in a bent state, together with the pair of arms 26 which is in its closed state. In addition, the first balloon 104 and the second balloon 110 are both in a deflated state.

Figure 33B:
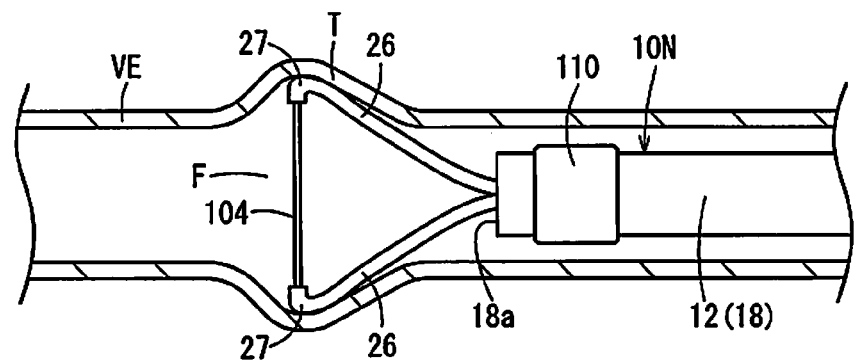
FIG. 33B is a second view for explaining the method of using the treatment device of FIG. 30.

Next, a flattening step of deforming the body lumen into a form having a flat portion F is conducted. Specifically, as shown in FIG. 33B, the pair of arms 26 is protruded from a distal end opening 18a of the shaft 18, and, upon this, the pair of arms 26 is expanded, whereby the vein VE is formed with the flat portion F. In this instance, the first balloon 104 assumes a rectilinear shape between distal ends of the pair of arms 26, and is positioned inside the flat portion F. Note that in forming the vein VE with the flat portion F, the degree of flattening of the vein VE may be checked by ultrasonic means.

Figure 33C:
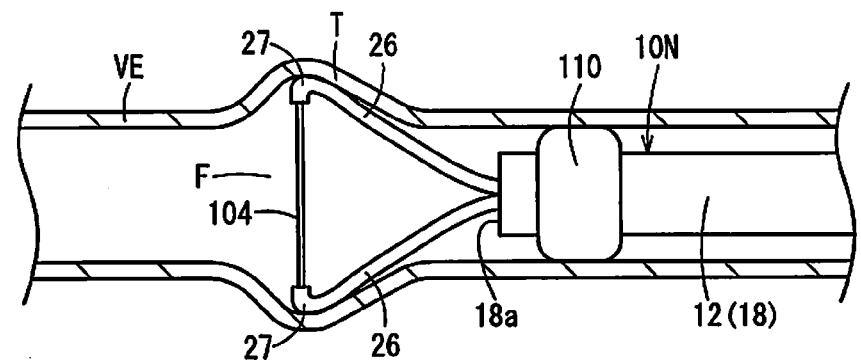
FIG. 33C is a third view for explaining the method of using the treatment device of FIG. 30.

Subsequently, a shaft-side occlusion step is conducted in which a gap between the shaft 18 and the body lumen is temporarily occluded. Specifically, under an operation of the second inflation/deflation operating device 116, the inflating fluid is supplied into the second balloon 110, whereby the second balloon 110 is inflated at a predetermined pressure, as depicted in FIG. 33C. This results in a state in which a blood flow in the vein VE is temporarily blocked.

Next, an arm-side occlusion step is conducted in which the lumen of the flat portion F is temporarily occluded.

Figure 29:
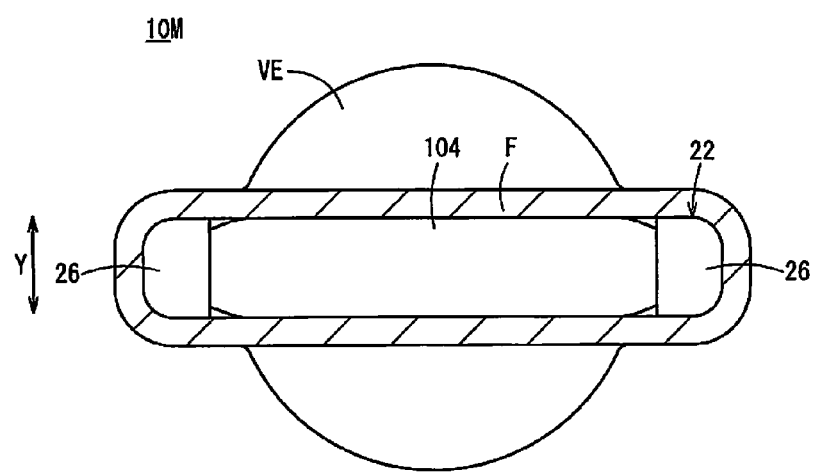
FIG. 29 is a sectional view taken along line XXIX-XXIX of FIG. 28C.
Figure 34A:
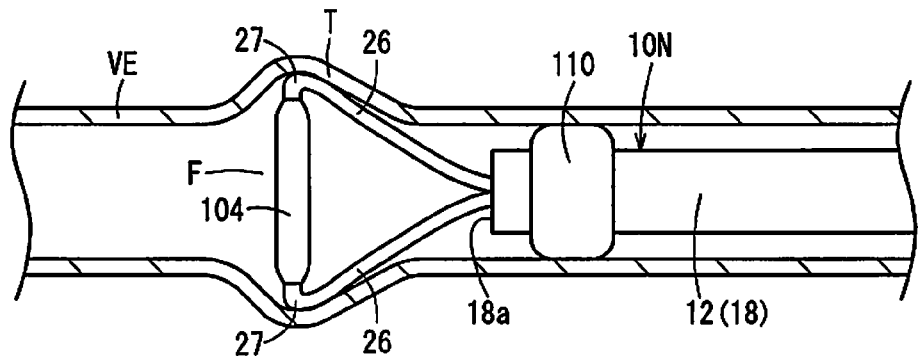
FIG. 34A is a fourth view for explaining the method of using the treatment device of FIG. 30.

Specifically, under an operation of the first inflation/deflation operating device 106, the inflating fluid is supplied into the first balloon 104, whereby the first balloon 104 is inflated at a predetermined pressure, as shown in FIG. 34A. This results in a state in which a flow path defined by the lumen of the flat portion F is temporarily closed (see, also, FIG. 29 relating to the treatment device 10M).

In the case where the first balloon 104 is inflated after the inflation of the second balloon 110 as above, the blood flow in the vein VE is cut off by the second balloon 110 prior to the occlusion of the flat portion F. Therefore, the blood pressure acting on the flat portion F is lowered, which makes it easy to keep the flat portion F in a flat state. Note that the second balloon 110 may be inflated after the inflation of the first balloon 104, reversely to the above procedure.

Figure 34B:
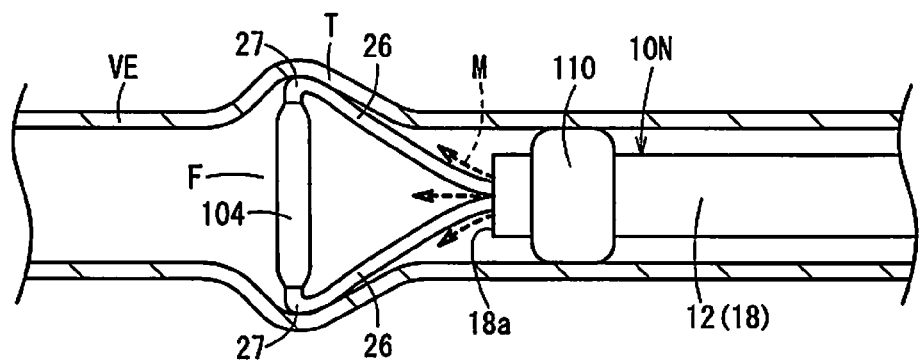
FIG. 34B is a fifth view for explaining the method of using the treatment device of FIG. 30.

Subsequently, a supplying step is carried out in which a sclerosing agent M is supplied to a region between a first occluding section (first balloon 104) and a second occluding section (second balloon 110). Specifically, as shown in FIG. 34B, with the first balloon 104 and the second balloon 110 kept in the inflated state, the sclerosing agent M is discharged from a supply device 96 connected to a connector 94 (see FIG. 30), and is made to flow through a lumen 25 of a support 24, to be discharged via the distal end opening 18a of the shaft 18. As a result, the sclerosing agent M is supplied to the flat portion F of the vein VE. In this case, the sclerosing agent M may be discharged at least once or may be continuously discharged at a fixed flow rate.

Figure 34C:
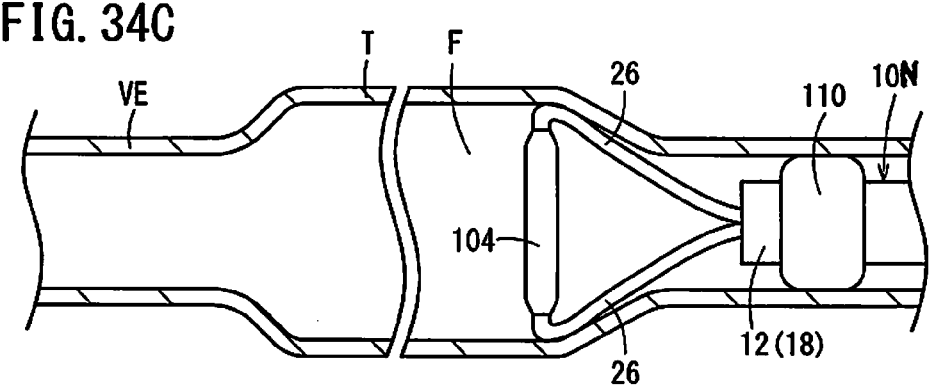
FIG. 34C is a sixth view for explaining the method of using the treatment device of FIG. 30.

Next, a moving step is conducted in which the pair of arms 26 in the expanded state, the first occluding section in the inflated state, the second occluding section in the inflated state and the shaft 18 are moved proximally. Specifically, as depicted in FIG. 34C, with the pair of arms 26, the first balloon 104 and the second balloon 110 kept in their expanded or inflated states, the treatment device 10N as a whole is moved proximally at a fixed speed and over a range where treatment is needed, and the treatment device 10N is stopped in a predetermined position.

Note that the sclerosing agent M may be discharged multiple times during a period after the first balloon 104 is inflated and until the treatment device 10N is stopped in the predetermined position. Besides, in the case of a procedure pattern in which the sclerosing agent M is continuously discharged at a fixed flow rate, the discharge of the sclerosing agent M is also stopped when the movement of the treatment device 10N is stopped.

After the vein VE is treated over a desired range, the first balloon 104 and the second balloon 110 are deflated by discharging the inflating fluid or fluids out of the first balloon 104 and the second balloon 110 (deflation step). In this case, the deflation of the first balloon 104 may be before or after the deflation of the second balloon 110. Alternatively, the deflation of the first balloon 104 and the deflation of the second balloon 110 may be carried out concurrently.

After the deflation of the first balloon 104 and the second balloon 110, the pair of arms 26 and the first balloon 104 are re-stored into the shaft 18 (storing step), and the treatment device 10N is drawn out of the living body (the vein VE) (drawing-out step).

According to the treatment device 10N configured as above, the supplied sclerosing agent M is sealed in between the first occluding section (first balloon 104) and the second occluding section (second balloon 110), so that the sclerosing agent M in a suitable concentration can be supplied to the flat portion F more efficiently. In addition to this, other effects similar to those of the treatment device 10M depicted in FIG. 25 can be obtained with the treatment device 10N.

In the aforementioned treatment device 10N and treatment device 10M, the balloon 104 (first balloon 104) as the occluding section (first occluding section) may be replaced with other configuration that can temporarily occlude the lumen of the flat portion.

Thus, as another configuration of the occluding section (first occluding section) than the aforementioned, there may be adopted, for example, a membrane-shaped member which is expanded (unfolded) like a sail by receiving a blood flow when disposed inside the flat portion F. In this case, both ends of the membrane-shaped member are fixed (connected) to the respective distal end portions 27 of the pair of arms 26.

In a state where the pair of arms 26 is stored in a closed state inside the shaft 18, the membrane-shaped member is stored in a folded state inside the shaft 18. As the pair of arms 26 is protruded from the distal end opening 18a of the shaft 18 and expanded widthwise, the membrane-shaped member is pulled by the distal ends of the pair of arms 26, to be unfolded so as to extend between the distal end portions 27 of the pair of arms 26. When the treatment device 10M as a whole (or the treatment device 10N as a whole) is moved proximally within the body lumen, the membrane-shaped member is spread by receiving a blood flow, resulting in a state where the flat portion F is temporarily occluded.

Alternatively, as a further configuration of the occluding section (first occluding section), there may be adopted a flexible spongy member which is elastically deformable. In this case, the spongy member is fixed (connected) between the distal end portions 27 of the pair of arms 26.

In a state where the pair of arms 26 is stored in a closed state inside the shaft 18, the spongy member is stored in a folded state (or in a compressed state) inside the shaft 18. As the pair of arms 26 is protruded from the distal end opening 18a of the shaft 18 and expanded widthwise, the spongy member is unfolded (spread) so as to extend between the distal ends of the pair of arms 26 by being pulled by the distal end portions 27 of the pair of arms 26 (or by its own elastic restoring force). This results in a state where the flat portion F is temporarily occluded by the spongy member.

Note that the occlusion by the membrane-shaped member or spongy member provided at the pair of arms 26 is not restricted to the state in which the lumen of the flat portion F is perfectly closed with the membrane-shaped member or spongy member without leaving any gap (100% occlusion), but includes a state in which most of the lumen of the flat portion F (for example, not less than 70% to 90% or not less than 95% of the cross-sectional area of the flow path in the flat portion F in the case where the occlusion by the membrane-shaped member or the spongy member is not applied) is closed.

In the aforementioned treatment device 10N, the second balloon 110 as the second occluding section may be replaced by other configuration that can temporarily occlude a gap between the shaft 18 and the body lumen.

Thus, as another configuration of the second occluding section, there may be adopted, for example, a membrane-shaped member which is expanded (spread or unfolded) like a sail by receiving a blood flow in the periphery of the shaft 18. In this case, the membrane-shaped member is fixed (connected) to a peripheral portion of the shaft 18, and extends circumferentially in an annular shape around the shaft 18. When the treatment device 10M as a whole (or the treatment device 10N as a whole) is moved proximally within the body lumen, the membrane-shaped member is expanded (spread or unfolded) in the periphery of the shaft 18 by receiving the blood flow, resulting in that the gap between the shaft 18 and the body lumen is temporarily occluded.

Note that when there is provided a sheath which covers the periphery of the shaft 18 and is slidable in the axial direction relative to the shaft 18, it is possible to control the expansion of the membrane-shaped member at an arbitrary timing. Specifically, the membrane-shaped member can be maintained in a contracted state (folded state) in a condition where the membrane-shaped member is covered with the sheath, and the membrane-shaped member can be put into an expandable state in a condition where the membrane-shaped member is freed from the coverage with the sheath.

Alternatively, as a further configuration of the second occluding section, there can be adopted a flexible spongy member that is elastically deformable. In this case, the spongy member is fixed (connected) to a peripheral portion of the shaft 18, and extends circumferentially in an annular shape around the shaft 18. Inside the body lumen, a gap between the shaft 18 and the body lumen is temporarily occluded by the spongy member.

Note that when there is provided a sheath which covers the periphery of the shaft 18 and is slidable in the axial direction relative to the shaft 18, it is possible to control the expansion of the spongy member at an arbitrary timing. Specifically, the spongy member can be kept in a contracted state in a condition where the spongy member is covered with the sheath, and the spongy member can be expanded in a condition where the spongy member is freed from the coverage with the sheath.

The occlusion by the membrane-shaped member or spongy member provided around the peripheral portion of the shaft 18 is not restricted to the state where the gap between the shaft 18 and the body lumen is perfectly closed with the membrane-shaped member or spongy member without leaving any gap (100% occlusion), but includes a state where most of the gap between the shaft 18 and the body lumen (for example, not less than 70% to 90% or not less than 95% of the cross-sectional area of the flow path in the gap in a case where the occlusion by the membrane-shaped member or spongy member is not applied) is closed.

In the treatment device 10M or treatment device 10N, the configuration in which the sclerosing agent M is supplied toward the flat portion F through the lumen 19 and the distal end opening 18a of the shaft 18 may be replaced by a configuration wherein the sclerosing agent M is supplied toward the flat portion F via the distal end opening 98a of the tube 98, like in FIG. 22.

Figure 35:
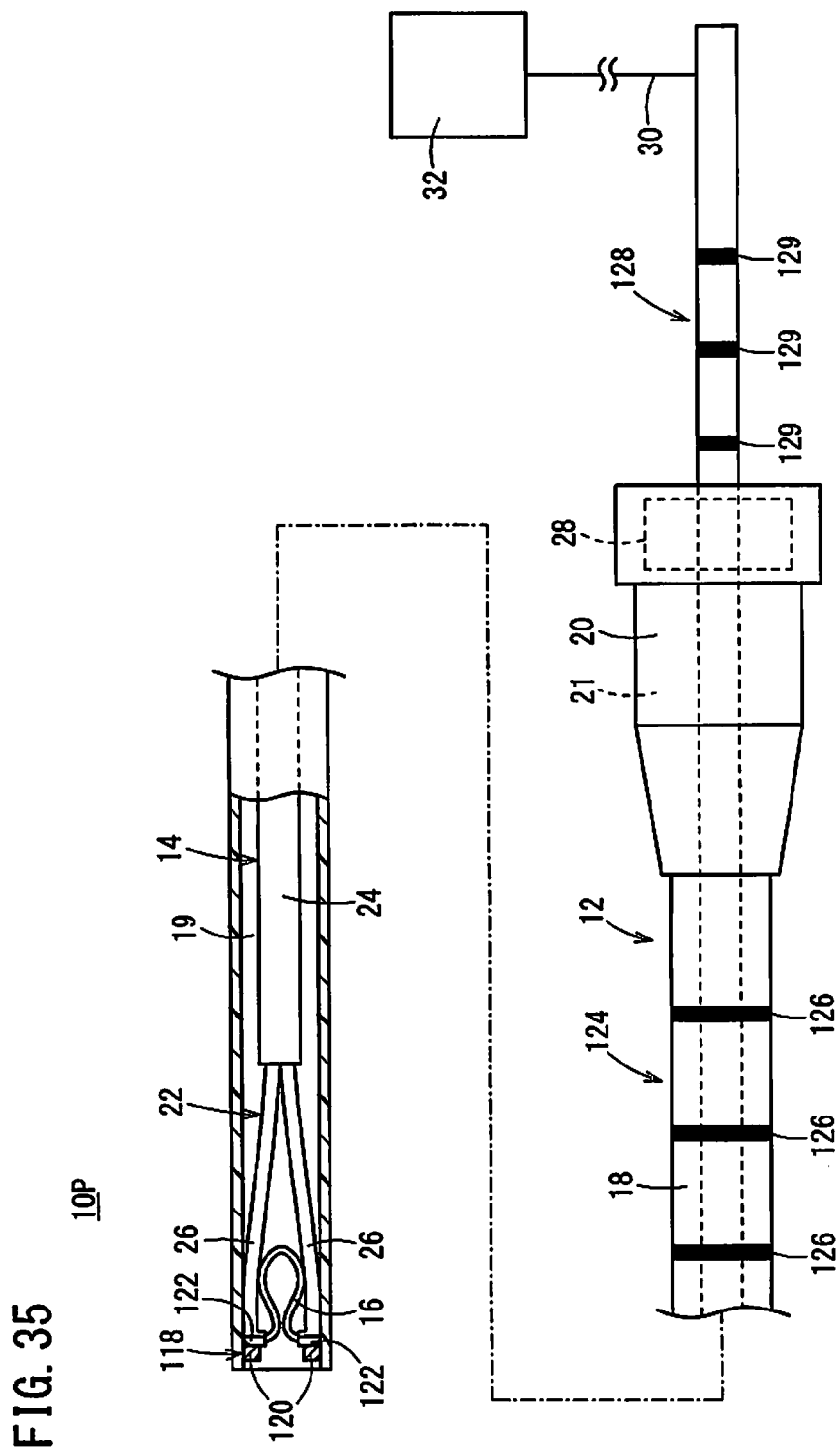
FIG. 35 is a partially omitted schematic view of yet another treatment device.
Figure 36A:
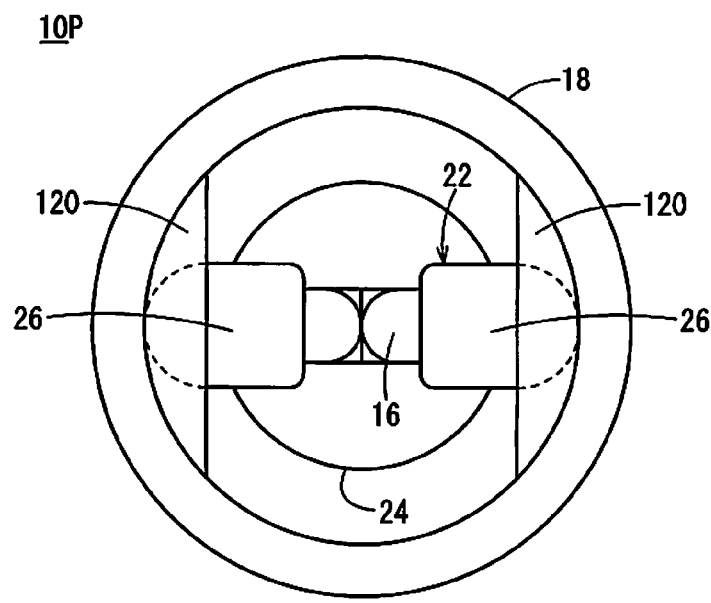
FIG. 36A is a view of the treatment device (in a locked state) of FIG. 35, as viewed from the side of a distal end opening.
Figure 36B:
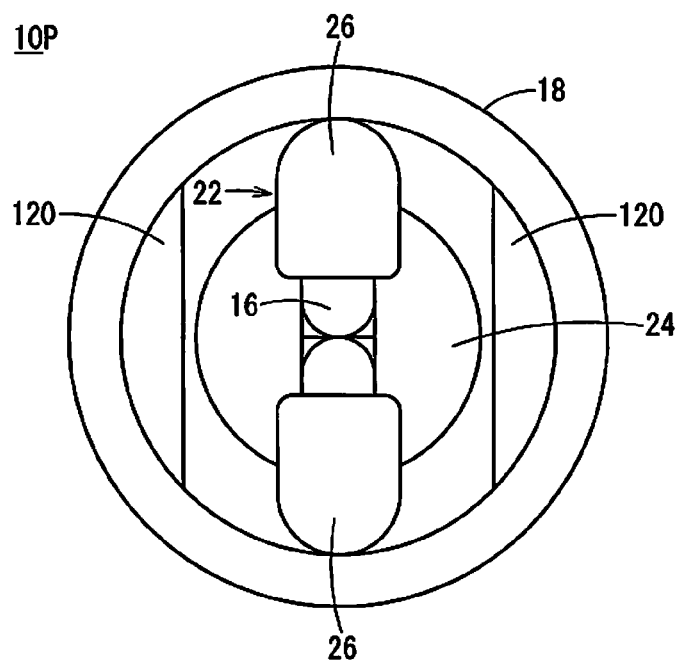
FIG. 36B is a view of the treatment device (in an unlocked state) of FIG. 35, as viewed from the side of the distal end opening.

FIG. 35 is a partially omitted schematic view of a treatment device 10P of yet another configuration. In FIG. 35, a pair of arms 26 is stored in a shaft 18. FIG. 36A is a view of the treatment device 10P (in a locked state) as viewed from the side of a distal end opening 18a, and FIG. 36B is a view of the treatment device 10P (in an unlocked state) as viewed from the side of the distal end opening 18a.

While the treatment device 10P is configured based on the configuration of the treatment device 10A depicted in FIG. 1, etc., it may be configured based on any of the other treatment devices 10B to 10N described above.

The treatment device 10P includes a stopper 118 adapted to retain the pair of arms 26 within the shaft 18 until a distal portion of the treatment device 10P is delivered to a target site. The stopper 118 is provided at or in the vicinity of a distal portion of the shaft 18. According to the relative positions of the shaft 18 and the pair of arms 26 in the circumferential direction, the stopper 118 is put into either one of a state of permitting protrusion of the pair of arms 26 from the shaft 18 and a state of inhibiting the protrusion of the pair of arms 26 from the shaft 18.

The stopper 118 includes, for example, locking pieces 120 projecting inward from an inner peripheral surface of the shaft 18 in opposite positions with respect to the circumferential direction, as shown in FIG. 35. In a state where the relative positions of the arms 26 and the locking pieces 120 in the circumferential direction are so set that they are overlapped, as depicted in FIG. 35 and FIG. 36A, the arms 26 are inhibited by the locking pieces 120 from advancing within the shaft 18. Accordingly, an unintended protrusion of the pair of arms 26 from the distal end opening 18a of the shaft 18 can be favorably prevented, and the prevention can be favorably maintained until the distal portion of the treatment device 10P is delivered to the target site in a living body.

When the distal portion of the treatment device 10P is delivered to the target site in the living body, an internal device 14 is rotated relative to a catheter 12 by 90 degrees circumferentially. This causes the arms 26 and the locking pieces 120 to get out of the overlapping state in the circumferential direction, as depicted in FIG. 36B. In other words, the arms 26 are moved into positions displaced from the locking pieces 120 along the circumferential direction. Then, the internal device 14 is advanced relative to the catheter 12, whereon the pair of arms 26 passes between the locking pieces 120 (which constitute the stopper 118) and protrude from the distal end opening 18a of the shaft 18.

Besides, in the treatment device 10P, the arms 26 are provided at their distal end portion with markers 122 (e.g., X-ray imaging markers, or ultrasonic markers) which are discernible on a radioscopic or ultrasonic-imaging basis. When the pair of arms 26 is protruded from the distal end opening 18a of the shaft 18 and expanded widthwise inside a body lumen (blood vessel), the spacing between the markers 122 provided at the distal end portions of the pair of arms 26 is enlarged. This enables easy confirmation of the widthwise expansion of the pair of arms 26 under radioscopy or ultrasonic imaging, and permits the user to find a starting position of flattening of the blood vessel.

In addition, in the treatment device 10P, the shaft 18 is provided, over a predetermined axial range of a proximal portion thereof, with a scale section 124 for indicating the length of a part treated by use of the treatment device 10P. In a condition where the distal portion of the treatment device 10P has reached the target position (the position of an affected part) in the living body, at least a part of the scale section 124 is present inside the living body. The scale section 124 includes a plurality of marks 126 (graduations) arranged at intervals along the axial direction. The marks 126 are arranged at regular intervals, which can be 1 cm to 10 cm, for example.

In the use of the treatment device 10P, when the catheter 12 and the internal device 14 are together moved proximally with the pair of arms 26 in a widthwise expanded state within a blood vessel, the marks 126 of the scale section 124 come to appear outside of the living body according to the moving amount. The length of the affected part needing a treatment is preliminarily grasped from a radioscopic or ultrasonic image or the like. In order to move the pair of arms 26 proximally by a distance corresponding to the length of the affected part, the user can operate the treatment device 10P proximally while looking at the scale section 124. Note that the length of the affected part is, for example, about 5 cm to 50 cm and, therefore, the distance between the mark 126 at the most distal side and the mark 126 at the most proximal side is set to be about 5 cm to 50 cm, for example.

Further, in the treatment device 10P, a support 24 is provided, over a predetermined axial range of a proximal portion thereof, with a position indication section 128 including a plurality of marks 129 arranged at intervals along the axial direction. The position indication section 128 indicates the extent of protrusion of the pair of arms 26 from the shaft 18. The position indication section 128 is so configured that in a condition where the axial position of the mark 129 at the most proximal side coincides with a proximal end plane of the catheter 12 (a proximal end plane of a hub 20), the pair of arms 26 is protruded sufficiently from the distal end opening 18a of the shaft 18 and are expanded widthwise. Accordingly, a control of the position of the pair of arms 26 (the length of protrusion of the pair of arms 26 from the distal end opening 18a of the shaft 18) can be easily carried out.

Figure 37:
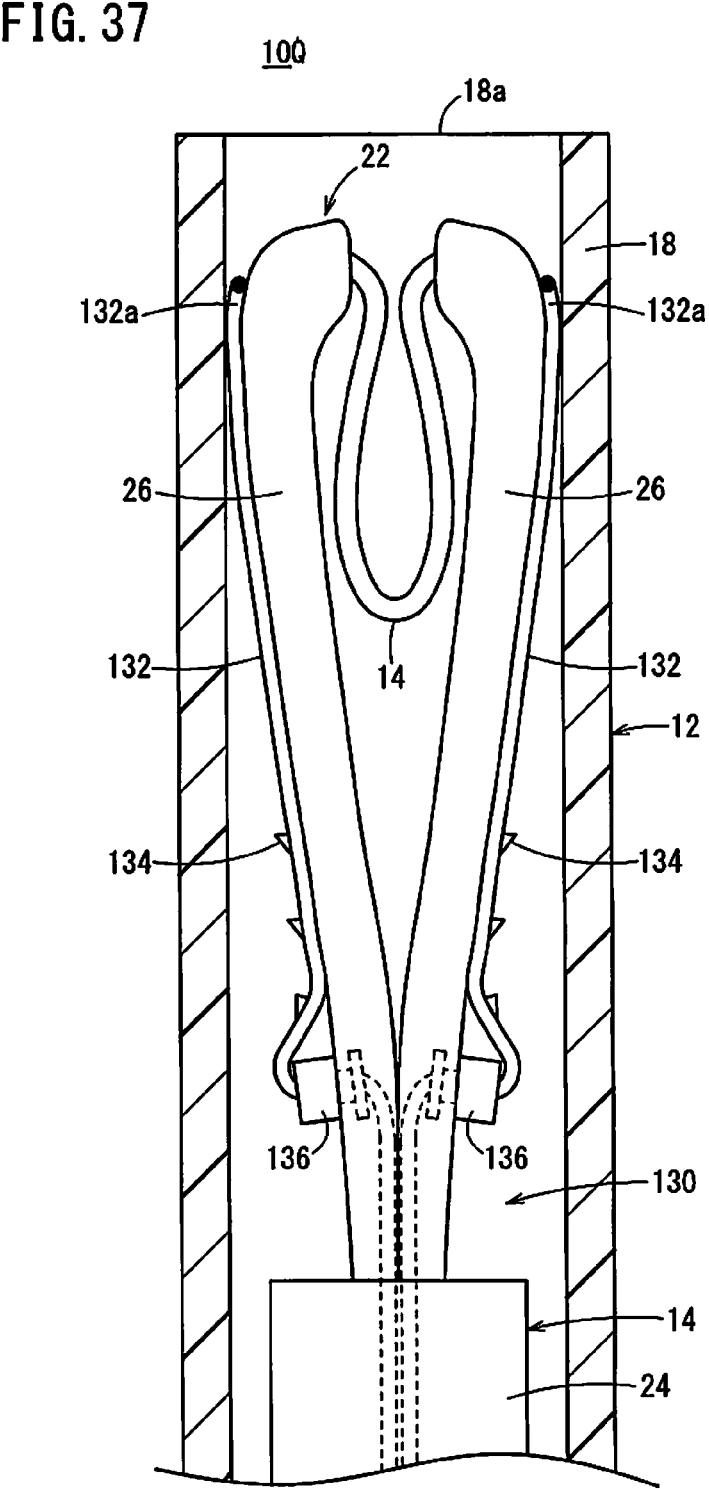
FIG. 37 is a partially sectional view of a distal portion of a yet further treatment device.

A structure (reinforcement structure 130) for reinforcing the expansion of a pair of arms 26 may be provided, as in a treatment device 10Q depicted in FIG. 37. The reinforcement structure 130 includes traction members 132 for pulling distal end portions of the pair of arms 26 proximally, locking claws 134 provided on the traction members 132, and constraint members 136 provided slidably on the arms 26.

The traction members 132 are each a flexible linear member, which can be composed of a wire, for example. A distal end portion 132a of the traction member 132 is fixed to a distal end portion of the arm 26. The traction member 132 is laid along the arm 26, over a range from one end to an intermediate portion thereof, and extends to a proximal portion of a support 24.

As shown in FIG. 37, the traction member 132 enters the arm 26 in the vicinity of a proximal end portion of the arm 26, for example, and extends through the inside of the support 24 to the proximal portion of the support 24. A proximal portion of the traction member 132 is led out to the exterior at the proximal portion of the support 24 or is connected to an operating section provided separately at the proximal portion of the support 24, in such a manner that the traction member 132 can be pulled proximally by an operation on the side of the proximal end of the support 24.

The locking claw 134 can pass through the constraint member 136 upon a proximal movement of the traction member 132, but is caught on the constraint member 136 after passing through the constraint member 136, thereby preventing the traction member 132 from returning distally. As depicted in FIG. 37, each traction member 132 may be provided with a plurality of the locking claws 134 arranged at intervals along the traction member 132. With locking claws 134 thus provided in plurality on each traction member 132, it is possible to reinforce the expansion of the pair of arms 26 according to the thickness (diametral size) of a blood vessel to be treated.

Figure 38A:
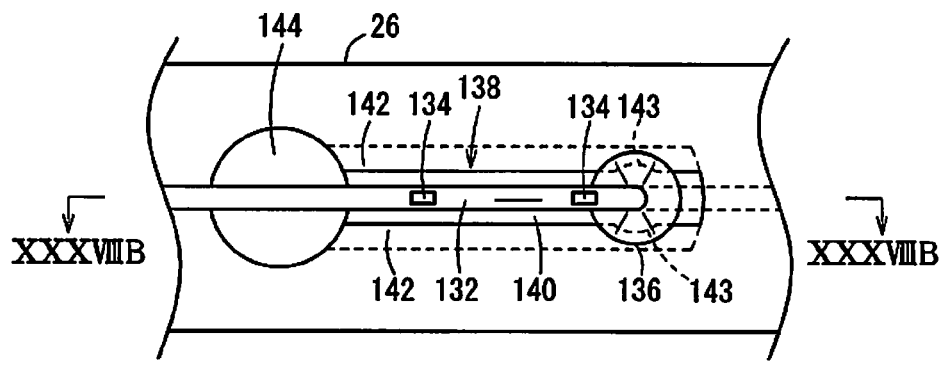
FIG. 38A is a side view of a restriction member of the treatment device shown in FIG. 37 and its surroundings.

The constraint member 136 is formed from an elastically deformable material. FIG. 38A is a side view of the constraint member 136 and its surroundings, and FIG. 38B is a sectional view taken along line XXXVIIIB-XXXVIIIB of FIG. 38A.

Figure 38B:
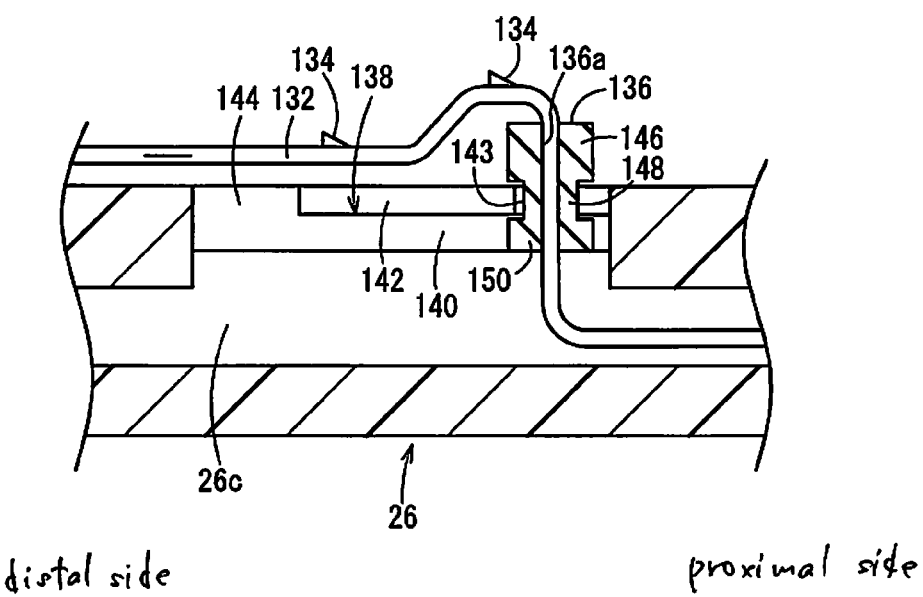
FIG. 38B is a sectional view taken along line XXXVIIIB-XXXVIIIB of FIG. 38A.

As shown in FIGS. 38A and 38B, the constraint member 136 is mounted to a groove-shaped guide rail 138 provided at a proximal-side outer surface of the arm 26. The constraint member 136 includes, for example, a head portion 146, a shaft portion 148 which is thinner (smaller in diametral size) than the head portion 146, and an engaging flange portion 150 which is thicker (larger in diametral size) than the shaft portion 148, with the head portion 146 and the engaging flange portion 150 being formed at both ends of the shaft portion 148.

In an initial state, the head portion 146 is located outside of the arm 26, and the shaft portion 148 and the engaging flange portion 150 are disposed inside the guide rail 138. The traction member 132 is passed through an insertion section 136a formed to penetrate the constraint member 136, and is inserted in and passed through the lumen formed inside the arm 26. The insertion section 136a is formed, for example, in the shape of a slit or a hole.

The guide rail 138 provided in the arm 26 extends in the extending direction of the arm 26. The guide rail 138 includes: a passage 140 permitting the constraint member 136 to move along the extending direction of the arm 26; restriction guides 142 provided on both sides of the passage 140 so as to inhibit disengagement of the constraint member 136 from the passage 140; and a release port 144 provided on the distal side of the restriction guides 142 so as to permit disengagement of the constraint member 136 from the passage 140.

The opening width (diameter) between the restriction guides 142 is smaller than the width (diameter) of the engaging flange portion 150 of the constraint member 136. This prevents disengagement of the constraint member 136 from the passage 140.

In addition, on the proximal side of the restriction guides 142 is provided a recessed engaging section 143, in which the shaft portion 148 of the constraint member 136 is disengageably engaged in the initial state. The opening width between the restriction guides 142 is set to be smaller than the width (diameter) of the shaft portion 148 of the constraint member 136. This ensures that the constraint member 136 is held in the engaging section 143 unless a force equal to or greater than a predetermined value and directed toward the side of the release port 144 (the distal side) is exerted on the constraint member 136.

The release port 144 is greater (in diameter) than the engaging flange portion 150 of the constraint member 136. This ensures that when the constraint member 136 reaches the position of the release port 144, disengagement of the constraint member 136 from the passage 140 (from the guide rail 138) becomes possible.

An operation of the reinforcement structure 130 configured as above will be described below. With the pair of arms 26 stored in a shaft 18 (with the pair of arms 26 in its contracted state), as shown in FIG. 37, the treatment device 10Q is inserted into a patient's blood vessel. When a distal portion of the treatment device 10Q has reached a target position (treatment site) in the blood vessel, the pair of arms 26 is protruded from the shaft 18, thereby expanding the pair of arms 26 widthwise.

Figure 39:
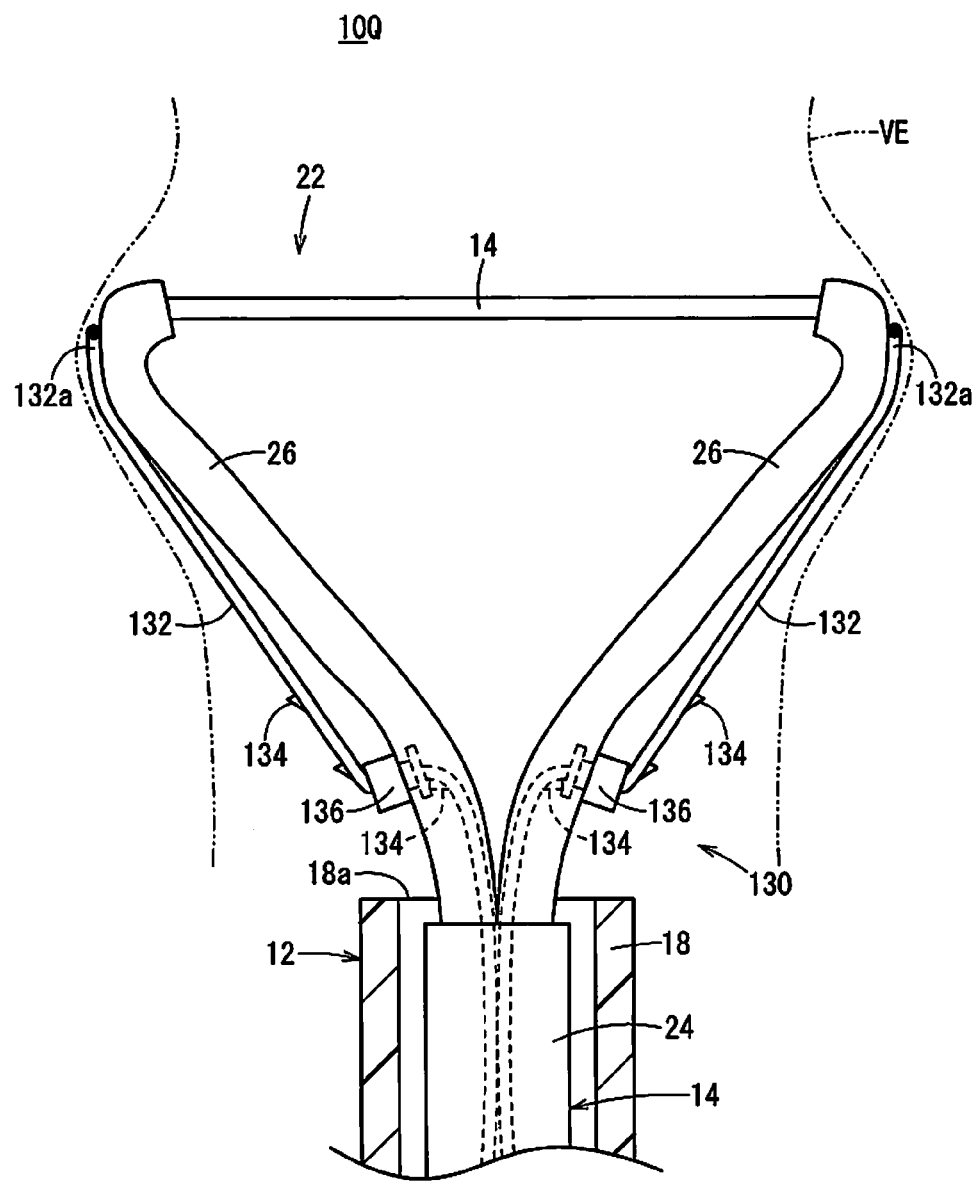
FIG. 39 is a partially sectional view of the treatment device shown in FIG. 37, in its state when arms are expanded.

In this instance, if the expansion of the arms 26 depends only on the expanding forces of the arms 26 themselves, sufficient expansion of the arms 26 may be hampered by a reaction force exerted from the wall of the blood vessel. In view of this, the traction members 132 are pulled proximally by an operation on the side of the proximal end of the treatment device 10Q (on the hand side). This results in that as shown in FIG. 39, the traction members 132 are each stretched between the distal end portion of the arm 26 and the constraint member 136, so that the traction members 132 having their distal end portions 132a fixed to the arms 26 generate forces in directions for expanding the arms 26 (expansion-assisting forces). In this instance, besides, the movement of each traction member 132 is attended by passage of the locking claw or claws 134 (provided on the traction member 132) through the constraint member 136, with the locking claw 134 being then caught on the constraint member 136 inside of the arm 26. Even when the operating force exerted on the traction members 132 by the user is released, the expansion-assisting forces applied to the arms 26 by the traction members 132 are maintained.

After an affected part is treated, the shaft 18 is moved distally in relation to the pair of arms 26, in order to re-store the pair of arms 26 into the shaft 18. In this instance, the distal end of the shaft 18 contacts the constraint members 136, and pushes the constraint members 136 toward the distal ends of the arms 26. When a force equal to or greater than a predetermined value and directed distally is exerted on each constraint member 136, the constraint member 136 is disengaged from the engaging section 143, and advances along the passage 140, to reach the release port 144.

Then, the engaging flange portion 150 being smaller than the release port 144 is permitted to pass through the release port 144, resulting in that the constraint member 136 is disengaged from the guide rail 138. This ensures that the traction members 132 are slackened, and, consequently, the expansion-assisting forces applied to the arms 26 by the traction members 132 are released. Accordingly, the re-storing of the pair of arms 26 into the shaft 18 can be performed without any hindrance.

Note that while the treatment device 10Q depicted in FIG. 37 is the same as the treatment device 10A shown in FIG. 1, etc. in the other points of configuration than the reinforcement structure 130, the other treatment devices 10B to 10N and 10P described above may similarly be provided with the reinforcement structure 130.

Figure 40:
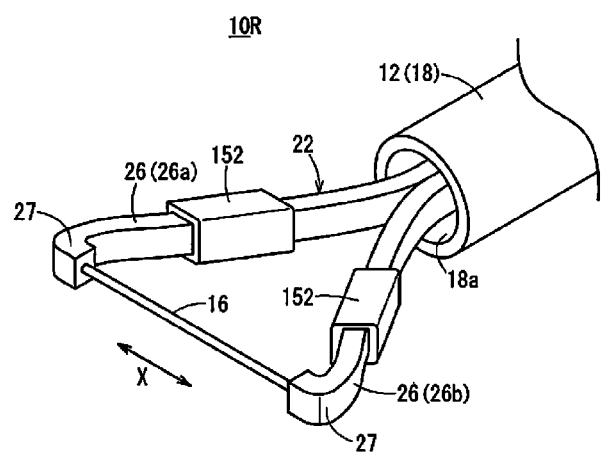
FIG. 40 is a perspective view of a pair of arms with reinforcement sections added thereto.

In order to prevent the expansion of a pair of arms 26 inside a body lumen (a vein VE or the like) from becoming insufficient due to a reaction force exerted from the wall of the body lumen, reinforcement sections 152 may be added to the arms 26, as in a treatment device 10R depicted in FIG. 40. As shown in FIG. 40, the reinforcement section 152 may be configured, for example, in the form of a cover surrounding a part in the longitudinal direction of the arm 26. The reinforcement sections 152 may be formed of the same material as the material of the arms 26, or may be formed of a material more rigid than the material of the arms 26. The reinforcement section 152 may be fixed to a part in the circumferential direction of the arm 26, for example, to the outer side or inner side of the arm 26.

Where each arm 26 is provided with the reinforcement section configured as above, the expanding force of the pair of arms 26 is augmented. Therefore, when the pair of arms 26 is protruded from a distal end opening 18a of a shaft 18 inside of a body lumen, the pair of arms 26 is sufficiently expanded widthwise, without being defeated by the reaction force exerted from the wall of the body lumen, so that a flat portion F can be effectively formed in the body lumen.

Note that while the treatment device 10R depicted in FIG. 40 is the same as the treatment device 10A shown in FIG. 1, etc. in the other points of configuration than the reinforcement sections 152, the other treatment devices 10B to 10N and 10P described above may similarly have the arms 26 provided with the reinforcement sections 152.

Figure 41A:
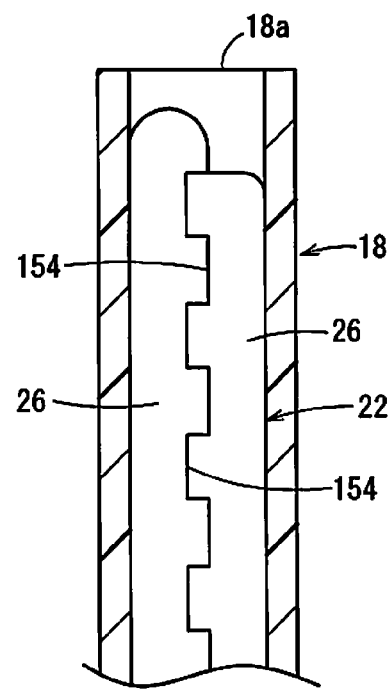
FIG. 41A is a partially sectional view showing a pair of arms according to another configuration example.
Figure 41B:
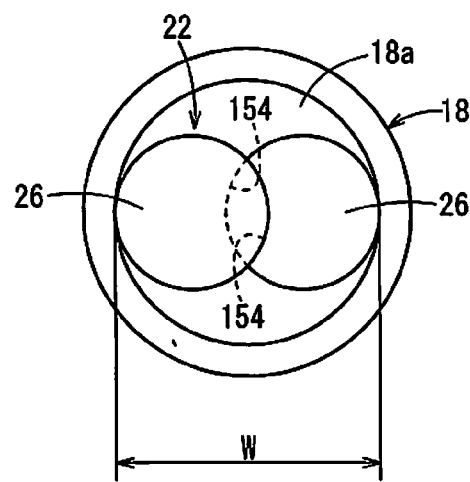
FIG. 41B is a view of the pair of arms of FIG. 41A as viewed from the side of a distal end opening of a shaft.

As illustrated in FIGS. 41A and 41B, the pair of arms 26 may be so configured that projected and recessed shapes 154 provided on the inner sides of the arms 26 along the longitudinal direction of the arms 26 mesh with each other in a state where the pair of arms 26 is stored in the shaft 18. Note that FIG. 41B is a view of the pair of arms 26 of FIG. 41A, as viewed from the side of the distal end opening 18a of the shaft 18. In the configuration wherein the projected and recessed shapes 154 thus mesh with each other, a reduction in the width W of the pair of arms 26 in the contracted state (stored state) is achieved. A reduction in the width W (diametral size) of the pair of arms 26 in the contracted state permits a corresponding reduction in the outside diameter of the shaft 18. Therefore, it becomes possible to reduce the size of a hole to be opened in the patient for insertion of a catheter 12. Accordingly, the treatment is made to be less invasive, and the burden on the patient can be alleviated.

Figure 42A:
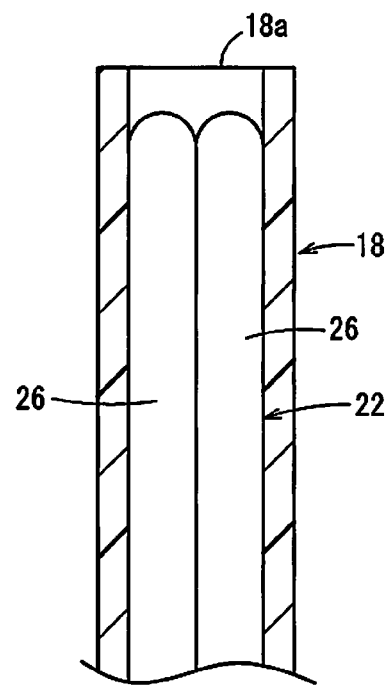
FIG. 42A is a partially sectional view showing a pair of arms according to a further configuration example.
Figure 42B:
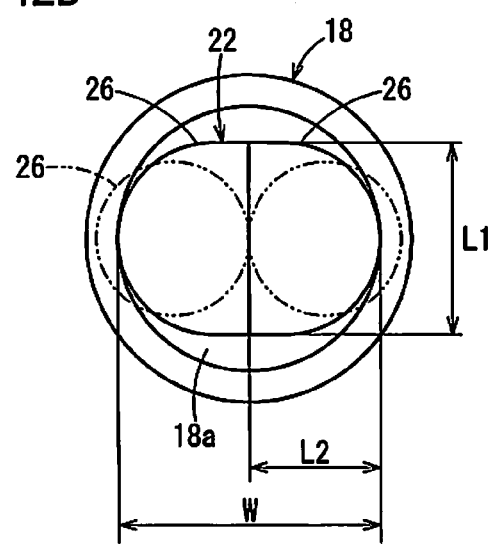
FIG. 42B is a view of the pair of arms of FIG. 42A as viewed from the side of a distal end opening of a shaft.

As depicted in FIGS. 42A and 42B, a configuration may be adopted wherein the profile of each of inside surfaces (mutually facing side surfaces) in cross section of the pair of arms 26 is a straight line extending in the thickness direction of the arms 26, whereas the profile of each of outside surfaces in cross section of the arms 26 is a circular arc, and the dimension L1 of each arm 26 along the thickness direction of the arms 26 is greater than the dimension L2 of each arm 26 along the width direction of the arms 26. As compared with the arm 26 whose cross section is circular as shown in imaginary line in FIG. 42B, the arm 26 whose cross section is shown in solid line in FIG. 42B ensures a reduction in the width W of the pair of arms 26 in the contracted state (stored state). This makes it possible to reduce the thickness (diametral size) of the shaft 18, and to mitigate the burden on the patient.

Besides, the pair of arms 26 having the solid-line cross-sectional shape is advantageous to the pair of arms 26 having the imaginary-line circular cross-sectional shape in the following points. Since the area of contact between the arm 26 and the blood vessel can be enlarged, a hole is less likely to be bored in the blood vessel, the blood vessel is less likely to be damaged, and the arm 26 is less likely to enter a collateral of the blood vessel. Moreover, since a larger cross-sectional area of the arm 26 can be gained, the arm 26 can be enhanced in strength.

Note that each of the aforementioned treatment devices 10A to 10N, and 10P to 10R can be configured as a device for various treatments requiring occlusion of a body lumen, other than the treatment of varicose veins. Therefore, each of the treatment devices is applicable also to treatments of various body lumens such as, for example, arteries, lymphatic vessels, bile duct, trachea, esophagus, urethra, nasal cavity, etc.

The detailed description above describes a treatment device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment device for occluding a body lumen, comprising:
   a hollow shaft which can be inserted into the body lumen;
   a flat portion forming section which has a pair of arms inserted in the shaft, the arms capable of being protruded from and retracted into a distal end opening of the shaft and expandable widthwise from a width smaller than a width of the hollow shaft to a width greater than the width of the hollow shaft and greater than a width of the body lumen to thereby deform the body lumen into a form having a flat portion as the pair of arms is expanded within the body lumen; and a heating section which is extendable and contractible in a width direction of the flat portion forming section, is extended as the pair of arms is expanded within the body lumen, and is configured to heat the flat portion, wherein the heating section includes a plurality of component members which are capable of relative displacement in the width direction of the flat portion forming section, and wherein the plurality of component members are stacked in a direction perpendicular to the width direction.

2. The treatment device according to claim 1, wherein the flat portion forming section is expandable widthwise on a more distal side than the shaft, and is configured to deform the body lumen into the form having the flat portion at a distal portion of the flat portion forming section upon an expansion of the flat portion forming section within the body lumen, and the heating section is supported by the distal portion of the flat portion forming section.

3. The treatment device according to claim 2, wherein each arm of the pair of arms is elastically deformable, the pair of arms is expanded widthwise by an elastic restoring force upon protrusion thereof from the distal end opening of the shaft, and the heating section is configured to be positioned inside the flat portion of the body lumen as the pair of arms is expanded.

4. The treatment device according to claim 1, wherein the plurality of component members are equal in width and in length.

5. A treatment device for occluding a body lumen, comprising:

a hollow shaft which can be inserted into the body lumen;

a flat portion forming section which has a pair of arms inserted in the shaft, the arms capable of being protruded from and retracted into a distal end opening of the shaft and expandable widthwise from a width smaller than a width of the hollow shaft to a width greater than the width of the hollow shaft and greater than a width of the body lumen to thereby deform the body lumen into a form having a flat portion as the pair of arms is expanded within the body lumen; and a heating section which is extendable and contractible in a width direction of the flat portion forming section, is extended as the pair of arms is expanded within the body lumen, and is configured to heat the flat portion, wherein the heating section includes a plurality of component members connected by bendable or foldable, electrically conductive interlock portions, and wherein the plurality of component members are stacked in a direction perpendicular to the width direction.

6. The treatment device according to claim 5, wherein the plurality of component members are equal in width and in length.

7. A method of occluding a body lumen, comprising:

inserting a hollow shaft into the body lumen;

protruding a flat portion forming section from a distal end opening of the shaft, said flat portion forming section having an expandable pair of arms;

expanding the pair of arms within the body lumen from a width smaller than a width of the hollow shaft to a width greater than the width of the hollow shaft and greater than a width of the body lumen to thereby deform the body lumen into a form having a flat portion;

extending a heating section within the body lumen in a width direction of the flat portion as the pair of arms is expanded within the body lumen; and heating the flat portion with the heating section, wherein the heating section includes a plurality of component members which are 1) capable of relative displacement in a width direction of the flat portion forming section or 2) connected by bendable or foldable, electrically conductive interlock portions, and the plurality of component members are stacked in a direction perpendicular to the width direction of the flat portion forming section.

8. The method according to claim 7, wherein the flat portion forming section is expandable on a more distal side than the shaft, and deforms the body lumen into the form having the flat portion at a distal portion of the flat portion forming section upon the expansion of the flat portion forming section within the body lumen, and the heating section is supported by the distal portion of the flat portion forming section.

9. The method according to claim 8, wherein each arm of the pair of arms is elastically deformable, and the pair of arms is expanded by an elastic restoring force upon protrusion thereof from the distal end opening of the shaft.

* * * * *